(12) United States Patent
Ogawa et al.

(10) Patent No.: US 9,944,970 B2
(45) Date of Patent: Apr. 17, 2018

(54) GLYCATED HEXAPEPTIDE OXIDASE AND USE THEREOF

(71) Applicants: KYOWA MEDEX Co., Ltd., Tokyo (JP); Kyoto University, Kyoto (JP)

(72) Inventors: Noriyuki Ogawa, Shizuoka (JP); Fumi Umehara, Shizuoka (JP); Takehide Kimura, Tokyo (JP); Kousaku Murata, Kyoto (JP); Wataru Hashimoto, Kyoto (JP)

(73) Assignees: KYOWA MEDEX CO., LTD., Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/898,022

(22) PCT Filed: Jul. 7, 2014

(86) PCT No.: PCT/JP2014/068011
§ 371 (c)(1),
(2) Date: Dec. 11, 2015

(87) PCT Pub. No.: WO2015/005258
PCT Pub. Date: Jan. 15, 2015

(65) Prior Publication Data
US 2016/0138073 A1 May 19, 2016

(30) Foreign Application Priority Data
Jul. 9, 2013 (JP) .................... 2013-143277

(51) Int. Cl.
| | | |
|---|---|---|
| C12P 19/02 | (2006.01) | |
| C12Q 1/26 | (2006.01) | |
| G01N 33/72 | (2006.01) | |
| C12N 9/04 | (2006.01) | |
| C12N 9/06 | (2006.01) | |
| C12Q 1/37 | (2006.01) | |

(52) U.S. Cl.
CPC ............ *C12Q 1/26* (2013.01); *C12N 9/0006* (2013.01); *C12N 9/0032* (2013.01); *C12Q 1/37* (2013.01); *G01N 33/723* (2013.01); *G01N 33/725* (2013.01); *C12Y 105/03* (2013.01); *G01N 2333/805* (2013.01); *G01N 2333/90672* (2013.01); *G01N 2333/952* (2013.01)

(58) Field of Classification Search
None
See application file for complete search history.

(56) References Cited

U.S. PATENT DOCUMENTS

| | | | | |
|---|---|---|---|---|
| 8,304,249 | B2 * | 11/2012 | Aisaka ............... | C07K 14/805 435/190 |
| 8,790,905 | B2 | 7/2014 | Aisaka et al. | |
| 8,883,142 | B2 | 11/2014 | Aisaka et al. | |
| 2012/0003678 | A1 | 1/2012 | Aisaka et al. | |
| 2014/0057333 | A1 | 2/2014 | Aisaka et al. | |
| 2014/0234886 | A1 | 8/2014 | Aisaka et al. | |
| 2015/0118700 | A1 | 4/2015 | Ichiyanagi et al. | |
| 2016/0274129 | A1 | 9/2016 | Ichiyanagi | |

FOREIGN PATENT DOCUMENTS

| | | |
|---|---|---|
| CN | 102232111 A | 11/2011 |
| EP | 1223224 A1 | 7/2002 |
| EP | 1291416 A1 | 3/2003 |
| EP | 1555324 A1 | 7/2005 |
| EP | 1555325 A1 | 7/2005 |
| EP | 1626088 A1 | 2/2006 |
| EP | 2843050 A1 | 3/2015 |
| EP | 3061829 A1 | 8/2016 |
| JP | 2001-095598 A | 4/2001 |
| JP | 2003-235585 A | 8/2003 |
| JP | 2010-035469 A | 2/2010 |
| JP | 2010-115189 A | 5/2010 |
| JP | 2010-233502 A | 10/2010 |
| WO | WO-2004/038033 A1 | 5/2004 |
| WO | WO 2004/038034 A1 | 5/2004 |
| WO | WO-2004/104203 A1 | 12/2004 |
| WO | WO-2008/108385 A1 | 9/2008 |
| WO | WO-2010/041715 A1 | 4/2010 |
| WO | WO-2013/162035 A1 | 10/2013 |
| WO | WO-2015/060431 A1 | 4/2015 |

OTHER PUBLICATIONS

Davis et al., "A high-performance liquid chromatography method for hemoglobin A1$_c$," Diabetes. 27(2):102-7 (1978).
Ferri et al., "Engineering fructosyl peptide oxidase to improve activity toward the fructosyl hexapeptide standard for HbA1c measurement," Mol Biotechnol. 54(3):939-43 (2013).
Finke et al., "Preparation of a candidate primary reference material for the international standardisation of HbA1c determinations," Clin Chem Lab Med. 36(5):299-308 (1998).
Hirokawa et al., "Enhancement of thermostability of fungal deglycating enzymes by directed evolution," Appl Microbiol Biotechnol. 78(5):775-81 (2008).
Ichiyanagi et al., "Development of fructosyl peptide oxidase suitable for diabetes diagnosis," Japan Society for Bioscience, Biotechnology, and Agrochemistry Taikai Koen Yoshishu, Mar. 2013, vol. 2013, 3C15A06 (English translation provided).

(Continued)

*Primary Examiner* — Hope Robinson
(74) *Attorney, Agent, or Firm* — Clark & Elbing LLP

(57) ABSTRACT

The present invention provides a protein comprising an amino acid sequence in which arginine at position 61 of a protein comprising the amino acid sequence represented by SEQ ID NO: 1 is substituted to an amino acid selected from the group consisting of glycine, alanine, valine, leucine, serine, threonine, proline, cysteine, methionine, asparagine, glutamine, and aspartic acid; and a method for measuring a glycated hemoglobin in a sample, wherein the method comprises reacting a glycated hemoglobin in a sample with a protease to produce a glycated hexapeptide, then reacting the produced glycated hexapeptide with the aforementioned protein, and measuring a substance produced or consumed by the reaction.

8 Claims, 7 Drawing Sheets

(56) References Cited

OTHER PUBLICATIONS

Ichiyanagi et al., "Improvement of substrate specificity of fructosyl peptide oxidase from *coniochaeta* sp. NISL9330," Japan Society for Bioscience, Biotechnology, and Agrochemistry Taikai Koen Yoshishu, Mar. 2012, vol. 2012, 4C09A04 (English translation provided).
Jeppsson et al., "Approved IFCC reference method for the measurement of HbA1c in human blood," Clin Chem Lab Med. 40(1):78-89 (2002).
Katayama et al., "Tina-quant HbA1c, a homogenous immunoturbidimetric method for hemoglobin A1c," The Journal of the Japan Society for Clinical Laboratory Automation 18(4):620 (1993) (English language translation provided).
Kim et al., "Construction of engineered fructosyl peptidyl oxidase for enzyme sensor applications under normal atmospheric conditions," Biotechnol Lett. 34(3):491-7 (2012).
International Search Report for International Patent Application No. PCT/JP2014/068011, dated Aug. 5, 2014 (English language translation provided; 6 pages).
Written Opinion of the International Searching Authority for International Patent Application No. PCT/JP2014/068011, dated Aug. 5, 2014 (English language translation provided; 18 pages).
International Preliminary Report on Patentability for International Patent Application No. PCT/JP2014/068011, dated Jan. 12, 2016 (English language translation provided; 20 pages).
Sambrook et al., Molecular Cloning, A Laboratory Manual, 3rd. Ed., vol. 2, 10.47-10.48 (2001).
Extended European Search Report for European Patent Application No. 14823525.2, dated Jan. 25, 2017 (7 pages).

\* cited by examiner

GLYCATED HEXAPEPTIDE OXIDASE AND USE THEREOF

TECHNICAL FIELD

The present invention relates to proteins having glycated hexapeptide oxidase activity, DNAs encoding the proteins, methods for producing the proteins, methods for measuring glycated hemoglobin using the proteins, and reagents for measuring glycated hemoglobin.

BACKGROUND ART

Glycated proteins are contained in biological samples such as body fluid and hair, and body fluid includes blood in a living body, and such. The concentration of glycated proteins present in the blood depends on the concentration of sugars such as glucose dissolved in the serum, and in the field of clinical diagnosis, measurement of the concentration of hemoglobin A1c (herein after, HbA1c; Non-Patent Document 1), which is a glycated protein in the blood, is being used to diagnose and monitor diabetes mellitus. Hemoglobin is a heme protein consisting of two of each of the two types of subunits, the α-chain and the β-chain, and has a molecular weight of 64,000. HbA1c is defined as hemoglobin in which particularly the N-terminal valine residue of the β-chain is glycated. As a method for measuring this HbA1c, instrumental analytical methods using high performance liquid chromatography (HPLC) (Non-Patent Document 2), immunoassays using antigen-antibody reactions (for example, Non-Patent Document 3), and such had been known, but in recent years, enzymatic assays have been developed, and for example, a method using a protease and a glycated peptide oxidase (Patent Document 1) has been developed. Enzymatic assays can be applied to versatile automated analyzers, and since the operations are also simple, they are being developed actively.

The glycated peptide oxidase used in enzymatic assays is an enzyme that catalyzes the reaction which produces a sugar osone (an α-keto aldehyde), a peptide, and hydrogen peroxide by oxidatively cleaving, in the presence of oxygen molecules, the C—N bond in the ketose derivative produced by Amadori rearrangement of glucosylamine produced by the reaction between the hemiacetal of glucose and the N-terminal amino group of a peptide.

In the case of enzymatic assays, a method is known in which HbA1c is first degraded with a protease, and α-glycated valyl histidine (hereinafter, denoted as α-FVH) is produced from the N terminus of the β-chain of hemoglobin; next, glycated peptide oxidase is made to act on the produced α-FVH to produce hydrogen peroxide, a quinone dye is produced in the presence of peroxidase by the produced hydrogen peroxide, and the produced amount is determined by colorimetry using a spectrophotometer (Patent Document 1).

However, ε-glycated lysine (herein after denoted as ε-FK), in which a sugar is bound to the ε-amino group of lysine, and glycated peptides containing the ε-FK are produced as byproducts by the protease treatment, and it has been pointed out that there is a risk that, in case glycated peptide oxidase acts on them, the measured values of HbA1c may be higher than the true values (Patent Document 2).

Glycated peptide oxidase has been found from bacteria, fungi, and plants. For example, glycated peptide oxidase derived from the genus *Achaetomiella*, the genus *Chaetomium* (Patent Document 3), the genus *Curvularia* (Patent Document 2), the Rosaceae family, the Vitaceae family, the Apiaceae family (Patent Document 5), and such are known.

However, glycated peptide oxidases reported so far had drawbacks, such as:

(1) activity towards α-glycated valyl histidine (hereinafter denoted as α-FVH) which is an HbA1c-derived α-glycated dipeptide, in comparison to an α-glycated amino acid (for example, α-glycated valine (hereinafter denoted as α-FV)), is not necessarily high;

(2) as described above, in addition to the N-terminal α-glycated dipeptide, it also acts on ε-FK, and increases the measured values in HbA1c measurements; and (3) in the case of measurement methods using enzymes, the enzymes become unstable during measurement or storage.

To overcome these drawbacks, enzymes with decreased reactivity towards ε-FK (Patent Document 4), enzymes with increased thermostability (Non-Patent Document 4), and such, as a result of artificial introduction of mutations into glycated peptide oxidase have been reported. Furthermore, enzymes that have simultaneously overcome the above-mentioned drawbacks of (1) to (3) have been reported (Patent Document 6).

Conventionally, as an HbA1c measurement method set forth by the International Federation of Clinical Chemistry and Laboratory Medicine (IFCC), a known method for determining HbA1c concentration is the method, in which HbA1c β-chain is digested using Glu-C protease to dissociate a peptide fragment consisting of six amino acids including the glycated N-terminal amino acid [α-glycated hexapeptide: Fru-Val-His-Leu-Thr-Pro-Glu (SEQ ID NO: 134) (hereinafter denoted as α-F6P)], and this is measured using HPLC-capillary electrophoresis (HPLC-CE) or HPLC-mass spectrometry (HPLC-MS) (Non-Patent Document 5). This method is widely used to date as a practical standard method with excellent specificity, but it requires a special apparatus for detection, and has a problem that it requires complicated operations.

In comparison of the above-described practical standard method in the HbA1c measurement (which uses HPLC-CE or HPLC-MS) with an enzymatic assay, the subject of measurement of the former is a glycated hexapeptide, whereas the subject of measurement of the latter is mainly a glycated dipeptide. This is because most known glycated peptide oxidases are highly reactive towards relatively short glycated peptides. Development of an enzymatic assay based on the same principles as the practical standard method, in which α-F6P, a glycated hexapeptide derived from HbA1c, is measured and thereby HbA1c is measured, is believed to be very meaningful in industry also from the viewpoint of increasing the correlation between the two methods.

Known glycated hexapeptide oxidases that act on the glycated hexapeptide α-F6P corresponding to the N terminus of the β-chain of HbA1c are glycated peptide oxidases derived from Zingiberaceae plants (Patent Document 7), glycated peptide oxidases derived from Rosaceae, Vitaceae, and Apiaceae plants (Patent Document 5), glycated peptide oxidases derived from microorganisms (Patent Document 8), and chimeric enzymes consisting of two types of microorganism-derived glycated peptide oxidase sequences (Non-Patent Document 6); however, they have problems such as requiring a long time for reaction with glycated hexapeptides or insufficient reactivity with glycated hexapeptides.

Furthermore, as described above, conventional glycated peptide oxidases can only act on peptides with up to six amino acids, and enzymes having oxidase activity on longer peptide chains and glycated hemoglobin are not known. Therefore, in case measuring glycated hemoglobin by an enzymatic assay, peptide fragments have to be dissociated by a protease as described above, and then the glycated peptide oxidase is made to act on the fragments; however, in case other measurements besides the glycated hemoglobin measurements are taken simultaneously using an automatic analyzer or such, the protease in the reagent for measuring glycated hemoglobin may act on other reagents and may affect the measured values.

PRIOR ART DOCUMENTS

Patent Documents

[Patent Document 1] Japanese Patent Application Kokai Publication No. (JP-A) 2001-95598 (unexamined, published Japanese patent application).
[Patent Document 2] International Publication No. WO 2004/104203 pamphlet.
[Patent Document 3] JP-A (Kokai) 2003-235585.
[Patent Document 4] JP-A (Kokai) 2010-233502.
[Patent Document 5] International Publication No. WO 2004/038033 pamphlet.
[Patent Document 6] International Publication No. WO 2010/041715 pamphlet.
[Patent Document 7] International Publication No. WO 2004/038034 pamphlet.
[Patent Document 8] International Publication No. WO 2008/108385 pamphlet.

Non-Patent Documents

[Non-Patent Document 1] Clin Chem Lab Med, Vol. 36, p. 299-308 (1998).
[Non-Patent Document 2] Diabetes, Vol. 27(2), p. 102-107 (1978).
[Non-Patent Document 3] Nihon Rinsho Kensa Jidoka Gakkai Kaishi (Journal of the Japan Society for Clinical Laboratory Automation), Vol. 18, No. 4, p. 620 (1993).
[Non-Patent Document 4] Appl Microbiol Biotechnol, Vol. 78, No. 5, p. 775-781 (2008).
[Non-Patent Document 5] Clin Chem Lab Med, 40, 78-89, (2002)
[Non-Patent Document 6] Mol Biotechnol, 54 (3) p. 939-943 (2013)

SUMMARY OF THE INVENTION

Problems to be Solved by the Invention

The present invention was achieved in view of the above-mentioned problems. An objective of the present invention is to provide proteins having an activity of oxidizing glycated hexapeptides derived from glycated hemoglobin and producing hydrogen peroxide (hereinafter referred to as glycated hexapeptide oxidase activity). Another objective of the present invention is to provide DNAs encoding the proteins, recombinant DNAs comprising the DNAs, transformants transformed with the recombinant DNAs, methods for producing the proteins having glycated hexapeptide oxidase activity using the transformants and such, methods for measuring glycated hemoglobin using the proteins, and reagents for measuring glycated hemoglobin comprising the proteins. Furthermore, another objective of the present invention is to provide proteins having an activity of directly oxidizing glycated hemoglobin, methods for measuring glycated hemoglobin using the proteins, and reagents for measuring glycated hemoglobin comprising the proteins.

Means for Solving the Problems

The present invention relates to the following (1) to (29).
(1) A protein comprising an amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid.
(2) A protein comprising an amino acid sequence in which one or more amino acids other than the amino acid at position 61 are deleted, substituted, or added in the amino acid sequence of the protein of (1), and having glycated hexapeptide oxidase activity.
(3) A protein comprising an amino acid sequence having a homology of 90% or more to the amino acid sequence of the protein of (1), and having glycated hexapeptide oxidase activity.
(4) A protein in which an amino acid residue of the protein of (1) is modified by at least one mutation selected from the following [1] to [15]:
[1] mutation where arginine at position 63 is substituted with an amino acid selected from the group consisting of glycine, proline, and alanine;
[2] mutation where leucine at position 62 is substituted with glycine;
[3] mutation where glutamine at position 93 is substituted with glutamic acid;
[4] mutation where phenylalanine at position 267 is substituted with tyrosine;
[5] mutation where tyrosine at position 71 is substituted with serine or cysteine;
[6] mutation where aspartic acid at position 115 is substituted with an amino acid selected from the group consisting of asparagine and arginine;
[7] mutation where methionine at position 108 is substituted with an amino acid selected from the group consisting of lysine and arginine;
[8] mutation where leucine at position 75 is substituted with an amino acid selected from the group consisting of alanine and phenylalanine;
[9] mutation where serine at position 34 is substituted with threonine;
[10] mutation where tyrosine at position 52 is substituted with histidine;
[11] mutation where isoleucine at position 57 is substituted with valine;
[12] mutation where proline at position 66 is substituted with histidine;
[13] mutation where aspartic acid at position 95 is substituted with glutamic acid;
[14] mutation where lysine at position 105 is substituted with arginine; and
[15] mutation where alanine at position 355 is substituted with serine.
(5) A protein comprising an amino acid sequence in which at least one amino acid other than the amino acid at positions 34, 52, 57, 61, 62, 63, 66, 71, 75, 93, 95, 105, 108, 115, 267, and 355 is deleted, substituted, or added in the amino acid sequence of the protein of (4), and having glycated hexapeptide oxidase activity.
(6) A protein comprising the amino acid sequence represented by any one of SEQ ID NOs: 3 to 37.

(7) A protein comprising an amino acid sequence having a homology of 90% or more to the amino acid sequence represented by any one of SEQ ID NOs: 3 to 37, and having glycated hexapeptide oxidase activity.
(8) A protein comprising the amino acid sequence represented by any one of SEQ ID NOs: 6 to 37.
(9) A protein comprising an amino acid sequence having a homology of 90% or more to the amino acid sequence represented by any one of SEQ ID NOs: 6 to 37, and having an activity of directly oxidizing glycated hemoglobin.
(10) The protein of (9), wherein the glycated hemoglobin is HbA1c.
(11) A DNA encoding the protein of any one of (1) to (10).
(12) A DNA comprising the nucleotide sequence represented by any one of SEQ ID NOs: 41 to 75.
(13) A DNA that hybridizes under stringent conditions with a DNA having a nucleotide sequence complementary to the nucleotide sequence encoding the protein of (6), wherein the DNA encodes a protein having glycated hexapeptide oxidase activity.
(14) A DNA that hybridizes under stringent conditions with a DNA having a nucleotide sequence complementary to the nucleotide sequence represented by any one of SEQ ID NOs: 41 to 75, wherein the DNA encodes a protein having glycated hexapeptide oxidase activity.
(15) A DNA comprising the nucleotide sequence represented by any one of SEQ ID NOs: 44 to 75.
(16) A DNA that hybridizes under stringent conditions with a DNA having a nucleotide sequence complementary to the nucleotide sequence encoding the protein of (8), wherein the DNA encodes a protein having an activity of directly oxidizing glycated hemoglobin.
(17) A DNA that hybridizes under stringent conditions with a DNA having a nucleotide sequence complementary to the nucleotide sequence represented by any one of SEQ ID NOs: 44 to 75, wherein the DNA encodes a protein having an activity of directly oxidizing glycated hemoglobin.
(18) The DNA of (16) or (17), wherein the glycated hemoglobin is HbA1c.
(19) A recombinant DNA comprising the DNA of any one of (11) to (18).
(20) A transformant harboring the recombinant DNA of (19).
(21) A method for producing the protein of any one of (1) to (10), wherein the method comprises culturing the transformant of (20), producing and accumulating the protein of any one of (1) to (10) in the culture, and collecting the protein from the culture.
(22) A method for measuring glycated hemoglobin in a sample, wherein the method comprises producing a glycated hexapeptide by reacting the glycated hemoglobin in the sample with a protease, reacting the produced glycated hexapeptide with the protein of any one of (1) to (10), and measuring a substance produced or consumed by the reaction.
(23) A method for measuring glycated hemoglobin in a sample, wherein the method comprises reacting the glycated hemoglobin in the sample with the protein of any one of (8) to (10), and measuring a substance produced or consumed by the reaction.
(24) The measurement method of (22) or (23), wherein the glycated hemoglobin is HbA1c.
(25) The measurement method of any one of (22) to (24), wherein the substance produced by the reaction is hydrogen peroxide.
(26) A reagent for measuring glycated hemoglobin, wherein the reagent comprises a protease and the protein of any one of (1) to (10).
(27) A reagent for measuring glycated hemoglobin, wherein the reagent comprises the protein of any one of (8) to (10).
(28) The reagent of (26) or (27), which further comprises a reagent for measuring hydrogen peroxide.
(29) The reagent of any one of (26) to (28), wherein the glycated hemoglobin is HbA1c.

Effects of the Invention

The present invention provides proteins having glycated hexapeptide oxidase activity, DNAs encoding the proteins, recombinant DNAs comprising the DNAs, transformants transformed with the recombinant DNAs, methods for producing proteins having glycated hexapeptide oxidase activity using the transformants and such, methods for measuring glycated hemoglobin using the proteins, reagents for measuring glycated hexapeptides comprising the proteins, proteins having an activity of directly oxidizing glycated hemoglobin, methods for measuring glycated hemoglobin using the proteins, and reagents for measuring glycated hemoglobin comprising the proteins.

MODE FOR CARRYING OUT THE INVENTION

1. Proteins of the Present Invention

Figure 1:
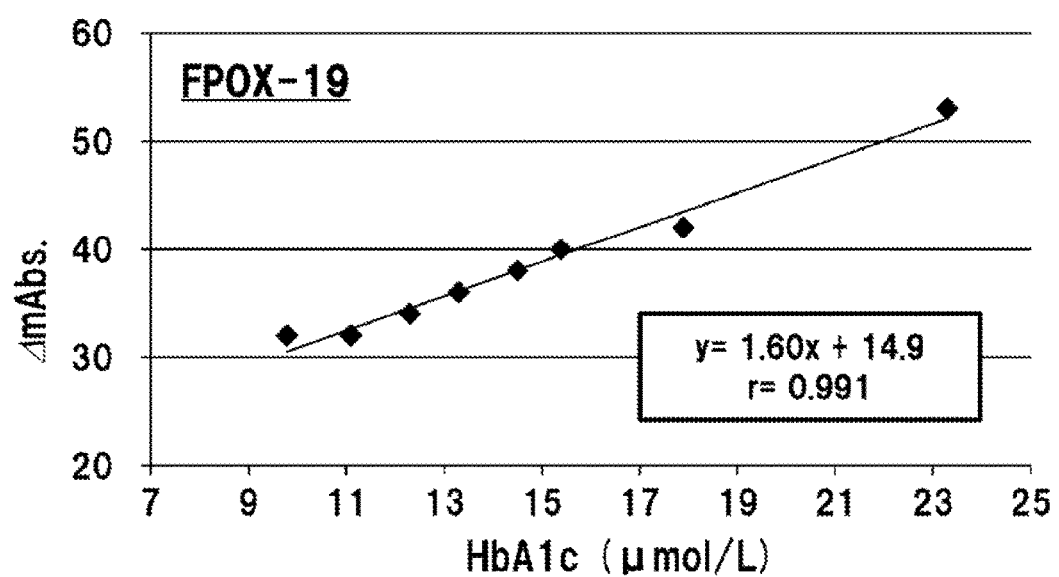
FIG. 1 shows a graph indicating the correlation between the method for measuring glycated hemoglobin of the present invention using V8 protease and FPOX-19, and the method for measuring glycated hemoglobin using both of the HPLC method (KO500 method) and the hemoglobin-SLS method.

Proteins of the present invention include:

[1] a protein comprising an amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid;

[2] a protein comprising an amino acid sequence in which one or more amino acids other than the amino acid at position 61 are deleted, substituted, or added in the amino acid sequence of the protein of [1], and having glycated hexapeptide oxidase activity;

[3] a protein comprising an amino acid sequence having a homology of 90% or more to the amino acid sequence of the protein of [1], and having glycated hexapeptide oxidase activity;

[4] a protein in which an amino acid residue of the protein of [1] is modified by at least one mutation selected from the following (1) to (15):

(1) mutation where arginine at position 63 is substituted with an amino acid selected from the group consisting of glycine, proline, and alanine;

(2) mutation where leucine at position 62 is substituted with glycine;

(3) mutation where glutamine at position 93 is substituted with glutamic acid;

(4) mutation where phenylalanine at position 267 is substituted with tyrosine;

(5) mutation where tyrosine at position 71 is substituted with serine or cysteine;

(6) mutation where aspartic acid at position 115 is substituted with an amino acid selected from the group consisting of asparagine and arginine;

(7) mutation where methionine at position 108 is substituted with an amino acid selected from the group consisting of lysine and arginine;

(8) mutation where leucine at position 75 is substituted with an amino acid selected from the group consisting of alanine and phenylalanine;

(9) mutation where serine at position 34 is substituted with threonine;

(10) mutation where tyrosine at position 52 is substituted with histidine;

(11) mutation where isoleucine at position 57 is substituted with valine;

(12) mutation where proline at position 66 is substituted with histidine;

(13) mutation where aspartic acid at position 95 is substituted with glutamic acid;

(14) mutation where lysine at position 105 is substituted with arginine; and

(15) mutation where alanine at position 355 is substituted with serine;

[5] a protein comprising an amino acid sequence in which at least one amino acid other than the amino acid at positions 34, 52, 57, 61, 62, 63, 66, 71, 75, 93, 95, 105, 108, 115, 267, and 355 is deleted, substituted, or added in the amino acid sequence of the protein of [4], and having glycated hexapeptide oxidase activity;

[6] a protein comprising the amino acid sequence represented by any one of SEQ ID NOs: 3 to 37;

[7] a protein comprising an amino acid sequence having a homology of 90% or more to the amino acid sequence represented by any one of SEQ ID NOs: 3 to 37, and having glycated hexapeptide oxidase activity;

[8] a protein comprising the amino acid sequence represented by any one of SEQ ID NOs: 6 to 37;

[9] a protein comprising an amino acid sequence having a homology of 90% or more to the amino acid sequence represented by any one of SEQ ID NOs: 6 to 37, and having an activity of directly oxidizing glycated hemoglobin; and

[10] the protein of [9], wherein the glycated hemoglobin is HbA1c.

In the above, a protein comprising an amino acid sequence with one or more amino acid deletions, substitutions, or additions, and having glycated hexapeptide oxidase activity can be obtained, for example, by introducing site-specific mutations to a DNA encoding a protein comprising the amino acid sequence represented by SEQ ID NO: 1 using site-specific mutagenesis methods described in Molecular Cloning, A Laboratory Manual, Second Edition, Cold Spring Harbor Laboratory Press (1989) (hereinafter, abbreviated as Molecular Cloning, Second Edition); Current Protocols in Molecular Biology, John Wiley & Sons (1987-1997) (hereinafter, abbreviated as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); and Proc. Natl. Acad. Sci. USA, 82, 488 (1985); and such.

While the number of amino acids that are deleted, substituted, or added is not particularly limited, it is a number that can be deleted, substituted, or added by known methods such as the above-mentioned site-specific mutagenesis methods, and the number is one to dozens, preferably one to 20, more preferably one to ten, and even more preferably one to five.

In an amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid, in case one or more amino acids other than the amino acid at position 61 are deleted, substituted, or added, one or more (for example, two to several) amino acids may be deleted, substituted, or added at any positions other than at amino acid position 61 in the same sequence.

Examples of amino acid positions where amino acid deletions or additions are possible include one to several amino acids at the N-terminal or C-terminal side of the amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid.

Deletions, substitutions, or additions may occur simultaneously, and the substituted or added amino acids may be naturally-occurring type or non-naturally-occurring type amino acids. Examples of naturally-occurring type amino acids include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Hereinafter, examples of mutually substitutable amino acids are shown. Amino acids included in the same group are mutually substitutable.

Group A: leucine, isoleucine, norleucine, valine, norvaline, alanine, 2-aminobutanoic acid, methionine, O-methylserine, t-butyl glycine, t-butyl alanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine Furthermore, in order for the proteins of the present invention to have glycated hexapeptide oxidase activity, desirably, the proteins have a homology of 90% or more, for example, 94% or more, preferably 95% or more, more preferably 96% or more, even more preferably 97% or more, yet even more preferably 98% or more, and particularly preferably 99% or more to the amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid.

Homology of amino acid sequences and nucleotide sequences can be determined using the BLAST algorithm by Karlin and Altshul [Pro. Natl. Acad. Sci. USA, 90, 5873 (1993)] or FASTA [Methods Enzymol., 183, 63 (1990)]. Programs called BLASTN and BLASTX have been developed based on this BLAST algorithm [J. Mol. Biol., 215, 403 (1990)]. In case nucleotide sequences are analyzed by BLASTN based on BLAST, parameters are set, for example, at score=100 and wordlength=12. In case amino acid sequences are analyzed by BLASTX based on BLAST, parameters are set, for example, at score=50 and wordlength=3. In case using the BLAST and Gapped BLAST programs, the default parameters of each program are used.

A protein comprising an amino acid sequence having a homology of 90% or more, for example, 94% or more, preferably 95% or more, more preferably 96% or more, even more preferably 97% or more, yet even more preferably 98% or more, and particularly preferably 99% or more to the amino acid sequence in which arginine at position 61 of a protein comprising the amino acid sequence represented by SEQ ID NO: 1 is substituted with an amino acid selected from the group consisting of glycine, alanine, valine, leucine, serine, threonine, proline, cysteine, methionine, asparagine, glutamine, and aspartic acid, and having glycated hexapeptide oxidase activity is also a protein of the present invention.

A protein of the present invention is, for example, a protein comprising the amino acid sequence represented by any one of SEQ ID NOs: 3 to 37 (which are called FPOX-16, FPOX-17, FPOX-18, FPOX-18A, FPOX-18B, FPOX-18C, FPOX-18D, FPOX-19, FPOX-20, FPOX-21, FPOX-22, FPOX-23, FPOX-24, FPOX-25, FPOX-26, FPOX-27, FPOX-28, FPOX-29, FPOX-30, FPOX-31, FPOX-32, FPOX-33, FPOX-34, FPOX-35, FPOX-36, FPOX-37, FPOX-38, FPOX-39, FPOX-40, FPOX-41, FPOX-42, FPOX-43, FPOX-44, FPOX-45, and FPOX-46, respectively).

As a means for confirming that the proteins of the present invention have glycated hexapeptide oxidase activity, for example, one may confirm by producing a transformant that expresses the proteins of the present invention by a DNA recombination method, producing the proteins of the present invention using the transformant, and then using α-F6P as a substrate, measuring the substance produced or consumed by the reaction with the substrate. Here, the substance produced by the reaction with the substrate is, for example, hydrogen peroxide.

The proteins of the present invention oxidize glycated hemoglobin-derived glycated hexapeptide or HbA1c, which is a kind of glycated hemoglobin, using molecular oxygen to produce a sugar osone (an α-keto aldehyde), a hexapeptide or hemoglobin, and hydrogen peroxide.

The optimal pH and the range of stable pH of the glycated hexapeptide oxidase activity of the proteins of the present invention are not particularly limited, and the optimal pH is preferably around 6.0 to 8.0, and the stable pH for treatment at 40° C. for ten minutes is preferably pH6.0 to 9.0.

The range of the optimal temperature for activity is not particularly limited, and is preferably around 20° C. to 50° C. Higher the thermostability of the protein is, more preferred the protein is, and, for example, the protein with residual activity of 25% or more after treatment at 50° C. for 15 minutes is used favorably.

(Methods for Measuring Glycated Hexapeptide Oxidase Activity)

Measurement of glycated hexapeptide oxidase activity can be carried out by the following method, and the amount of enzyme that produces 1 μmol of hydrogen peroxide in one minute from α-F6P is defined as one unit (U).

(Reagents for Activity Measurements)

Solution A: 50 mmol/L phosphate buffer solution (pH7.0)

Solution B: Coloring agent 24 mmol/L solution of 10-(carboxymethylaminocarbonyl)-3,7-bis(dimethylamino) phenothiazine sodium salt (DA-67) in dimethylformamide (DMF)

Solution C: Peroxidase solution 1 kU/L solution of peroxidase in 10 mmol/L phosphate buffer solution (pH7.0)

Solution D: Substrate solution 1 mmol/L aqueous solution of α-F6P

Solution E: Purified enzyme solution 0.1 to 10 mg/mL aqueous solution of glycated hexapeptide oxidase (Measurement Procedure)

To 10 mL of solution A, 12.6 μL of solution B and 35 μL of solution C are added, and the obtained solution is dispensed into each well of a 96-well microplate at 190 μL per sample. 20 μL of solution D and 10 μL of solution E were added and mixed, and the absorbance of the solution before reaction and the absorbance of the solution after reaction at 30° C. or 37° C. for 30 to 120 minutes are measured at 660 nm (main wavelength)/750 nm (sub-wavelength) using a fully automated microplate ETA analyzer, and the absorbance changes are calculated. The measurement values are calculated by subtracting the blank value, obtained by carrying out measurements using distilled water instead of the substrate solution (solution D).

Subsequently, various amounts of hydrogen peroxide are added to the above measurement system, the absorbance at 660 nm (main wavelength)/750 nm (sub-wavelength) is measured, and a calibration curve that shows the relationship between the amount of hydrogen peroxide and absorbance is prepared. The amount of hydrogen peroxide produced during a unit time is calculated from the change in signal due to each purified enzyme sample.

2. DNAs of the Present Invention

DNAs of the present invention include:

[a] a DNA encoding the protein of any one of the above [1] to [10];

[b] a DNA comprising the nucleotide sequence represented by any one of SEQ ID NOs: 41 to 75;

[c] a DNA that hybridizes under stringent conditions with a DNA having a nucleotide sequence complementary to the nucleotide sequence encoding the protein of the above [6], wherein the DNA encodes a protein having glycated hexapeptide oxidase activity;

[d] a DNA that hybridizes under stringent conditions with a DNA having a nucleotide sequence complementary to the nucleotide sequence represented by any one of SEQ ID NOs: 41 to 75, wherein the DNA encodes a protein having glycated hexapeptide oxidase activity;

[e] a DNA comprising the nucleotide sequence represented by any one of SEQ ID NOs: 44 to 75;

[f] a DNA that hybridizes under stringent conditions with a DNA having a nucleotide sequence complementary to the nucleotide sequence encoding the protein of the above [8], wherein the DNA encodes a protein having an activity of directly oxidizing glycated hemoglobin;

[g] a DNA that hybridizes under stringent conditions with a DNA having a nucleotide sequence complementary to the nucleotide sequence represented by any one of SEQ ID NOs: 44 to 75, wherein the DNA encodes a protein having an activity of directly oxidizing glycated hemoglobin; and

[h] the DNA of [f] or [g], wherein the glycated hemoglobin is HbA1c.

Herein, "to hybridize" means that a DNA of interest hybridizes with a DNA having a specific nucleotide sequence or with a part of this DNA. Therefore, the nucleotide sequence of the DNA having a specific nucleotide sequence or the part of this DNA may be a DNA with a length which is useful as a probe for Northern or Southern blot analyses, or which can be used as an oligonucleotide primer for PCR analyses. DNAs used as a probe include DNAs of at least 100 nucleotides or more, preferably 200 nucleotides or more, or more preferably 500 nucleotides or more; and, they can also be DNAs of at least 10 nucleotides or more, or preferably 15 nucleotides or more.

Methods for hybridization experiments of DNAs are well known. The conditions for hybridization can be determined and experiments can be carried out, for example, according to the descriptions in Molecular Cloning, Second Edition, Third Edition (2001); Methods for General and Molecular Bacteriology, ASM Press (1994); Immunology methods manual, Academic press (Molecular), and many other standard textbooks.

Examples of the above-mentioned stringent conditions include high stringency conditions in which a filter, on which DNA is immobilized, and a probe DNA are incubated in a solution containing 50% formamide, 5×SSC (750 mmol/L sodium chloride and 75 mmol/L sodium citrate), 50 mmol/L sodium phosphate (pH 7.6), 5×Denhardt's solution, 10% dextran sulfate, and 20 µg/L denatured salmon sperm DNA at 42° C. overnight, and after incubation, the filter is washed, for example, in 0.2×SSC solution at approximately 65° C.; and, conditions with lower stringency can also be used. The stringent conditions can be modified by adjusting the concentration of formamide (the conditions become less stringent as the concentration of formamide is lowered) or by changing the salt concentrations and temperature conditions. Examples of low stringency conditions include conditions in which incubation is carried out in a solution containing 6×SSCE (20×SSCE: 3 mol/L sodium chloride, 0.2 mol/L sodium dihydrogenphosphate and 0.02 mol/L EDTA, pH 7.4), 0.5% SDS, 30% formamide, and 100 µg/L denatured salmon sperm DNA at 37° C. overnight, and then washing using a 1×SSC, 0.1% SDS solution at 50° C. Examples of still less stringent conditions include conditions in which hybridization is carried out under the above-mentioned low stringency conditions using a solution with a high salt concentration (for example, 5×SSC) followed by washing.

The various conditions described above can also be set by adding or changing a blocking reagent used to suppress the background of the hybridization experiments. In case the above-mentioned blocking reagent is added, the hybridization conditions may be changed to make the conditions compatible.

DNAs capable of hybridizing under stringent conditions described above include DNAs comprising a nucleotide sequence having a homology of at least 90% or more, for example, 94% or more, preferably 95% or more, more preferably 96% or more, even more preferably 97% or more, yet even more preferably 98% or more, and particularly preferably 99% or more to the nucleotide sequence represented by any one of SEQ ID NOs: 41 to 75, when calculated for example using programs such as BLAST and FASTA described above based on the above-mentioned parameters.

Confirmation that a DNA which hybridizes under stringent conditions with the above-mentioned DNA is a DNA encoding a protein having glycated hexapeptide oxidase activity can be carried out by preparing a recombinant DNA expressing the DNA, introducing the recombinant DNA into host cells, culturing the obtained microorganisms, purifying the protein obtained from the culture, and measuring hydrogen peroxide produced by reaction of the purified protein as an enzyme source with α-F6P as a substrate.

Examples of the DNAs of the present invention include DNAs encoding a protein comprising the amino acid sequence represented by any one of SEQ ID NOs: 3-37, and DNAs comprising the nucleotide sequence represented by any one of SEQ ID NOs: 41-75.

3. Transformants of the Present Invention

Examples of the transformants of the present invention include transformants obtained by transforming host cells by a known method using a recombinant DNA comprising the DNA of the present invention described in the above 2. Examples of host cells include bacteria, yeast, animal cells, insect cells, and plant cells, and are preferably bacteria, more preferably prokaryotic cells, and even more preferably microorganisms belonging to the genus *Escherichia*.

4. Preparation of the DNAs of the Present Invention

The DNAs of the present invention can be obtained, for example, from a microorganism such as filamentous fungus, preferably from a microorganism belonging to the genus *Aspergillus* or the genus *Emericella*, or particularly preferably from a microorganism belonging to *Emericella nidulans* and such, using probes that can be designed based on the nucleotide sequence represented by any one of SEQ ID NOs: 41-75.

Alternatively, based on various genetic sequence databases, one can search for sequences having a homology of 90% or more, for example, 94% or more, preferably 95% or more, more preferably 96% or more, even more preferably 97% or more, yet even more preferably 98% or more, and particularly preferably 99% or more to the nucleotide sequences of DNAs encoding proteins comprising the amino acid sequences represented by SEQ ID NOs: 3 to 37, and based on the nucleotide sequences obtained by the search, the DNAs of the present invention or DNAs used in the production methods of the present invention can also be obtained according to the above-described methods from a chromosomal DNA, cDNA library, or such of an organism having the nucleotide sequences.

The nucleotide sequence of the DNA can be determined by using the obtained DNA as is or by cleaving it with appropriate restriction enzymes, inserting it into a vector by a conventional method, introducing the obtained recombinant DNA into host cells, then analyzing using a conventionally used nucleotide sequence analysis method such as the dideoxy method [Proc. Natl. Acad. Sci., USA, 74, 5463 (1977)] or a nucleotide sequence analyzer such as the 373A DNA Sequencer (manufactured by Perkin Elmer).

Examples of vectors for inserting the DNA of the present invention include pBluescript II KS(+) (manufactured by Stratagene), pDIRECT [Nucleic Acids Res., 18, 6069 (1990)], pCR-Script Amp SK(+) (manufactured by Stratagene), pT7Blue (manufactured by Novagen, Inc.), pCR II (manufactured by Invitrogen Corp.) and pCR-TRAP (manufactured by GenHunter Corp.).

As a host cell, microorganisms belonging to the genus *Escherichia* and such can be used.

Examples of microorganisms belonging to the genus *Escherichia* include *Escherichia coli* XL1-Blue, *Escherichia coli* XL2-Blue, *Escherichia coli* DH1, *Escherichia coli* MC1000, *Escherichia coli* ATCC 12435, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, and *Escherichia coli* ME8415.

As a method for introducing recombinant DNA, any method for introducing DNA into the above host cells can be used, and examples include the methods using calcium ion [Proc. Natl. Acad. Sci. USA, 69, 2110 (1972)], the protoplast method (JP-A (Kokai) S63-248394), and the electroporation method [Nucleic Acids Res., 16, 6127 (1988)].

In case that the obtained DNA was a partial DNA as a result of nucleotide sequence determination, the full length DNA can be obtained by Southern hybridization or such to a chromosomal DNA library using the partial DNA as a probe.

Further, it is also possible to prepare the desired DNA by chemical synthesis using a Model 8905 DNA synthesizer manufactured by PerSeptive Biosystems or the like, based on the determined nucleotide sequence of the DNA.

An example of the DNA obtained as described above is a DNA comprising the nucleotide sequence represented by any one of SEQ ID NOs: 41-75.

5. Methods for Producing Transformants Used for the Production Methods of the Present Invention Based on the DNAs of the present invention, a DNA fragment of an appropriate length containing a DNA encoding a protein of the present invention is prepared as necessary. A transformant with improved protein production rate can be obtained by modifying the nucleotide sequence of the DNA encoding the protein, and by substituting nucleotides in the nucleotide sequence so as to obtain codons that are optimal for expression in a host.

A recombinant DNA is produced by inserting the DNA fragment downstream of a promoter in an appropriate expression vector. A transformant which produces the protein of the present invention can be obtained by introducing the recombinant DNA into a host cell appropriate for the expression vector.

As a host cell, any host cell such as bacterial cell, yeast cell, animal cell, insect cell, and plant cell can be used, so long as it enables to express the gene of interest.

The expression vectors that are employed are those capable of autonomous replication or integration into the chromosome in the above-mentioned host cells, and comprising a promoter at a position that enables transcription of the DNA of the present invention.

In case of using a prokaryote such as a bacterium as a host cell, the recombinant DNA comprising the DNA of the present invention is preferably a recombinant DNA which is capable of autonomous replication in the prokaryote and, at the same time, is composed of a promoter, a ribosome binding sequence, a DNA of the present invention, and a transcription termination sequence. A gene regulating the promoter may also be included.

Examples of expression vectors are pCold I (manufactured by TAKARA BIO Inc.), pCDF-1b and pRSF-1b (both manufactured by Novagen Inc.), pMAL-c2x (manufactured by New England Biolabs Inc.), pGEX-4T-1 (manufactured by GE Healthcare Biosciences), pTrcHis (manufactured by Invitrogen Corp.), pSE280 (manufactured by Invitrogen Corp.), pGEMEX-1 (manufactured by Promega Corp.), pQE-30 (manufactured by Qiagen Inc.), pET-3 (manufactured by Novagen Inc.), pKYP10 (JP-A (Kokai) S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO 98/12343), pUC19 [Gene, 33, 103 (1985)], pSTV28 (manufactured by TAKARA BIO Inc.), pUC118 (manufactured by TAKARA BIO Inc.), pPA1 (JP-A (Kokai) S63-233798), and pTrc99a vector (4,176-bp, manufactured by GE Healthcare Biosciences).

Any promoter can be used so long as it can function in host cells such as *Escherichia coli*. Examples include promoters derived from *Escherichia coli*, phages, or the like, such as the trp promoter ($P_{trp}$), lac promoter ($P_{lac}$), $P_L$ promoter, $P_R$ promoter, and $P_{SE}$ promoter, as well as the SPO1 promoter, SPO2 promoter, and penP promoter. Promoters with artificial design changes can also be used, such as a promoter in which two $P_{trp}$ are arranged in tandem, the tac promoter, lacT7 promoter, and let I promoter.

Furthermore, the xylA promoter for expression in microorganisms belonging to the genus *Bacillus* [Appl. Microbiol. Biotechnol., 35, 594-599 (1991)], the P54-6 promoter for expression in microorganisms belonging to the genus *Corynebacterium* [Appl. Microbiol. Biotechnol., 53, 674-679 (2000)], and such can also be used.

It is preferable to use a plasmid in which the distance between the Shine-Dalgarno sequence, which is a ribosome binding sequence, and the initiation codon is appropriately adjusted (for example, 6 to 18 nucleotides).

In a recombinant DNA in which the DNA of the present invention has been ligated to an expression vector, a transcription termination sequence is not always necessary; however, a transcription termination sequence is preferably placed immediately downstream of a structural gene.

An example of such recombinant DNA is pET21-plu1440.

Examples of prokaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis,*

*Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. For example, they are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, *Bacillus subtilis* ATCC 33712, *Bacillus megaterium, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 14297, *Corynebacterium acetoacidophilum* ATCC 13870, *Microbacterium ammoniaphilum* ATCC 15354, *Serratia ficaria, Serratia fonticola, Serratia liquefaciens, Serratia marcescens, Pseudomonas* sp. D-0110, *Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globiformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC 29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus*, and *Zymomonas mobilis*.

As a method for introducing a recombinant DNA into a prokaryote, any method can be used so long as it introduces the DNA into the above-mentioned host cells, and examples include the method using calcium ion [Proc. Natl. Acad. Sci. USA, 69, 2110 (1972)], the protoplast method (JP-A (Kokai) S63-248394), and the electroporation method [Nucleic Acids Res., 16, 6127 (1988)].

In case of using an yeast strain as a host cell, YEp13 (ATCC 37115), YEp24 (ATCC 37051), YCp50 (ATCC 37419), pHS19, and pHS15 can be used as an expression vector.

As a promoter, any promoter can be used so long as it functions in an yeast strain, and examples include promoters such as the PHO5 promoter, the PGK promoter, the GAP promoter, the ADH promoter, the gal 1 promoter, the gal 10 promoter, the heat shock polypeptide promoter, the MFα1 promoter, and the CUP 1 promoter.

Examples of the host cells include yeast strains belonging to the genera *Saccharomyces, Schizosaccharomyces, Kluyveromyces, Trichosporon, Schwanniomyces, Pichia*, and *Candida*, and specific examples include *Saccharomyces cerevisiae, Schizosaccharomyces pombe, Kluyveromyces lactis, Trichosporon pullulans, Schwanniomyces alluvius, Pichia pastoris*, and *Candida utilis*.

As a method for introducing the recombinant DNA into yeast, any method can be used so long as it introduces the DNA into yeast, and examples include the electroporation method [Methods Enzymol., 194, 182 (1990)], the spheroplast method [Proc. Natl. Acad. Sci. USA, 81, 4889 (1984)], and the lithium acetate method [J. Bacteriol., 153, 163 (1983)].

In case of using an animal cell as a host, pcDNAI, pcDM8 (commercially available from Funakoshi Co., Ltd.), pAGE107 (JP-A (Kokai) H03-22979), pAS3-3 (JP-A (Kokai) H02-227075), pCDM8 [Nature, 329, 840 (1987)], pcDNAI/Amp (manufactured by Invitrogen Corp.), pREP4 (manufactured by Invitrogen Corp.), pAGE103 [J. Biochem., 101, 1307 (1987)], pAGE210, pAMo, pAMoA, and such can be used as an expression vector.

As a promoter, any promoter can be used so long as it functions in animal cells, and examples include the promoter of the immediate early (IE) gene of cytomegalovirus (CMV), SV40 early promoter or metallothionein promoter, the promoter of a retrovirus, heat shock promoter, SRα promoter, and such. Further, the enhancer of the IE gene of human CMV can be used in combination with the promoter.

Examples of the host cells include mouse myeloma cells, rat myeloma cells, mouse hybridoma cells, Namalwa cells and Namalwa KJM-1 cells which are human cells, human embryonic kidney cells, human leukemia cells, African green monkey kidney cells, Chinese hamster-derived CHO cells, and HBT5637 (JP-A (Kokai) S63-299).

Examples of mouse myeloma cell include SP2/0 and NSO; examples of rat myeloma cell include YB2/0; examples of human embryonic kidney cell include HEK293 (ATCC CRL-1573); examples of human leukemia cell include BALL-1; and examples of African green monkey kidney cell include COS-1 and COS-7.

As a method for introducing the recombinant DNA into animal cells, any method can be used so long as it introduces the DNA into animal cells, and examples include the electroporation method [Cytotechnology, 3, 133 (1990)], the calcium phosphate method (JP-A (Kokai) H02-227075), the lipofection method [Proc. Natl. Acad. Sci. USA, 84, 7413 (1987)], and the method described in Virology, 52, 456 (1973).

In case of using an insect cell as a host, the protein can be produced by using, for example, methods described in Baculovirus Expression Vectors, A Laboratory Manual, W. H.

Freeman and Company, New York (1992); Current Protocols in Molecular Biology; Molecular Biology, A Laboratory Manual; Bio/Technology, 6, 47 (1988), and such.

Specifically, a protein can be produced by co-introducing a recombinant gene transfer vector and a baculovirus into insect cells to obtain recombinant viruses in the culture supernatant of the insect cells, and then infecting insect cells with the recombinant viruses.

Examples of the gene transfer vector used in the method include pVL1392, pVL1393, and pBlueBacIII (all manufactured by Invitrogen Corp.).

As a baculovirus, for example, *Autographa californica* nuclear polyhedrosis virus which is a virus that infects the *Noctuidae Hadeninae* insects can be used.

As an insect cell, ovarian cell of *Spodoptera frugiperda*, ovarian cell of *Trichoplusia ni*, cultured cell derived from silkworm ovary, and such can be used.

Examples of ovarian cell of *Spodoptera frugiperda* include Sf9 and Sf21 (Baculovirus Expression Vectors, A Laboratory Manual); examples of ovarian cell of *Trichoplusia ni* include High 5 and BTI-TN-5B1-4 (Invitrogen Corp.); and examples of cultured cell derived from silkworm ovary include *Bombyx mori* N4.

Examples of a method for co-introducing the above-mentioned recombinant gene transfer vector and the above-mentioned baculovirus into insect cells for the preparation of recombinant viruses include the calcium phosphate method (JP-A (Kokai) H02-227075) and the lipofection method [Proc. Natl. Acad. Sci. USA, 84, 7413 (1987)].

In case of using a plant cell as a host cell, the Ti plasmid or tobacco mosaic virus vector can be used as an expression vector.

As a promoter, any promoter can be used so long as it functions in plant cells, and examples include the 35S promoter of cauliflower mosaic virus (CaMV) and the rice actin 1 promoter.

Examples of the host cells include plant cells of tobacco, potato, tomato, carrot, soybean, rape, alfalfa, rice, wheat, barley and such.

As a method for introducing the recombinant vector into plant cells, any method can be used so long as it introduces the DNA into plant cells, and examples include methods using *Agrobacterium* (JP-A (Kokai) S59-140885, JP-A (Kokai) S60-70080, WO 94/00977), the electroporation method (JP-A (Kokai) S60-251887), and methods using a particle gun (gene gun) (Japanese Patent No. 2606856 and Japanese Patent No. 2517813).

6. Methods for Producing the Proteins of the Present Invention

The proteins of the present invention can be produced by culturing the transformants obtained by the method of the above-described 5 in a medium, allowing the protein of the present invention to produce and accumulate in the culture, and collecting the protein from the culture.

The host of the above-mentioned transformants for producing the protein of the present invention may be any host such as a bacterium, yeast, animal cell, insect cell, or plant cell, and it is preferably a bacterium, more preferably a microorganism belonging to the genus *Escherichia*, and even more preferably a microorganism belonging to *Escherichia coli*.

In case of expression using yeast, an animal cell, an insect cell, or a plant cell, proteins with sugars or sugar chains attached thereto can be obtained.

Methods for culturing the above-mentioned transformants in a medium can be carried out following general methods used for culturing the host.

As a medium for culturing transformants obtained by using prokaryotes such as *Escherichia coli* or eukaryotes such as yeast as a host, either of a natural medium and synthetic medium may be used, as long as it is a medium which contains a carbon source, a nitrogen source, an inorganic salt, and such which can be assimilated by the organism and in which the transformants can be cultured efficiently.

As a carbon source, any carbon source that can be assimilated by the organism can be used, and a carbohydrate such as glucose, fructose, sucrose, molasses containing these, starch, or starch hydrolysate; an organic acid such as acetic acid and propionic acid; and an alcohol such as ethanol and propanol can be used.

As a nitrogen source, ammonia, an ammonium salt of an organic or inorganic acid such as ammonium chloride, ammonium sulfate, ammonium acetate, and ammonium phosphate, and other nitrogen-containing compounds, as well as peptone, meat extract, yeast extract, corn steep liquor, casein hydrolysate, soybean cake, soybean cake hydrolysate, and various fermentative microbial cells, and digestion products thereof can be used.

As an inorganic salt, potassium dihydrogenphosphate, dipotassium hydrogenphosphate, magnesium phosphate, magnesium sulfate, sodium chloride, ferrous sulfate, manganese sulfate, copper sulfate, calcium carbonate, and such can be used.

Culturing is usually carried out under aerobic conditions, for example, by a shaking culture or a deep aeration agitation culture. The culturing temperature is preferably 15 to 40° C., and the culturing period is usually five hours to seven days. The pH is maintained at 3.0 to 9.0 during the culturing. The pH adjustment is carried out by using an organic or inorganic acid, an alkali solution, urea, calcium carbonate, ammonia, and such.

As necessary, antibiotics such as ampicillin and tetracycline can be added to the medium during the culturing.

In case a microorganism transformed with an expression vector which comprises an inducible promoter as a promoter is cultured, an inducer may be added to the medium, as necessary. For example, in case culturing a microorganism transformed with an expression vector which comprises the lac promoter, isopropyl-β-D-thiogalactopyranoside (IPTG) or such may be added to the medium; and in case culturing a microorganism transformed with an expression vector that comprises the trp promoter, indoleacrylic acid or such may be added to the medium.

As a medium for culturing the transformants obtained by using an animal cell as a host, generally used media can be used, such as the RPMI1640 medium [J. Am. Med. Assoc., 199, 519 (1967)], Eagle's MEM medium [Science, 122, 501 (1952)], DMEM medium [Virology, 8, 396 (1959)], and 199 medium [Proc. Soc. Biol. Med., 73, 1 (1950)], or media to which fetal calf serum or such has been added to these media.

Culturing is usually carried out for one to seven days under conditions of pH 6 to 8 at 25° C. to 40° C. in the presence of 5% $CO_2$ or the like.

As necessary, antibiotics such as kanamycin, penicillin, and streptomycin can be added to the medium during the culturing.

As a medium for culturing the transformants obtained by using an insect cell as a host, generally used media can be used, such as TNM-FH medium (manufactured by Pharmingen, Inc.), Sf-900 II SFM medium (manufactured by Life Technologies, Inc.), ExCell 400 and ExCell 405 (both manufactured by JRH Biosciences, Inc.), and Grace's Insect Medium [Nature, 195, 788 (1962)].

Culturing is usually carried out for one to five days under conditions of pH 6 to 7 at 25° C. to 30° C., and such.

As necessary, antibiotics such as gentamicin can be added to the medium during the culturing.

Transformants obtained by using a plant cell as a host can be cultured as cells or after differentiation into plant cells or plant organs. As a medium for culturing the transformants, generally used media can be used, such as the Murashige and Skoog (MS) medium, White medium, and media to which plant hormones such as auxin and cytokinin have been added to these media.

Culturing is usually carried out for 3 to 60 days under conditions of pH 5 to 9 at 20° C. to 40° C.

As necessary, antibiotics such as kanamycin and hygromycin can be added to the medium during the culturing.

Methods for producing the proteins of the present invention include methods of production inside the host cells, methods of secretion outside the host cells, and methods of production on the host cell outer membrane. The structure of the protein to be produced can be altered according to the selected method.

In case the protein of the present invention is produced in host cells or on the host cell outer membrane, the protein can be actively secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in JP-A (Kokai) H05-336963, WO 94/23021, and such.

Specifically, the protein of the present invention can be actively secreted outside the host cells by producing the protein in a form in which a signal peptide is added upstream of a protein containing the active site of the protein of the present invention by using genetic engineering techniques.

It is also possible to increase the production level by utilizing a gene amplification system which uses a dihydrofolate reductase gene or such according to the method described in JP-A (Kokai) H02-227075.

Furthermore, by redifferentiation of a gene-introduced animal or plant cell, a gene-introduced animal (non-human transgenic animal) or plant (transgenic plant) can be constructed, and can be used to produce the proteins of the present invention.

In case the transformant producing the protein of the present invention is an animal or a plant, the protein can be produced by rearing the animal or culturing the plant according to general methods, allowing the protein to form and accumulate, and collecting the protein from the animal or plant.

Methods for producing the protein of the present invention using an animal include, for example, methods of producing the protein of the present invention in an animal constructed by gene introduction according to known methods [Am. J. Clin. Nutr., 63, 639S (1996); Am. J. Clin. Nutr., 63, 627S (1996); Bio/Technology, 9, 830 (1991)].

In the case of an animal, the protein of the present invention can be produced, for example, by rearing a non-human transgenic animal into which the DNA of the present invention or the DNA for use in the production method of the present invention has been introduced, allowing the protein to produce and accumulate in the animal, and collecting the protein from the animal. The places where the protein is produced and accumulated in the animal include milk (JP-A (Kokai) S63-309192), egg, and such of the animal. As a promoter used in this process, any promoter can be used so long as it functions in the animal, and for example, mammary gland cell-specific promoters such as a casein promoter, β casein promoter, β lactoglobulin promoter, and whey acidic protein promoter can be preferably used.

Methods for producing the protein of the present invention using a plant include, for example, methods for producing the protein by cultivating a transgenic plant into which the DNA encoding the protein of the present invention has been introduced according to known methods [Soshiki Baiyo (Tissue Culture), 20 (1994); Soshiki Baiyo, 21 (1995); Trends Biotechnol., 15, 45 (1997)], allowing the protein to produce and accumulate in the plant, and collecting the protein from the plant.

As a method for isolating and/or purifying the protein of the present invention produced by using the transformant that produces the protein of the present invention, general methods for isolating and purifying enzymes can be used.

For example, in case the protein of the present invention is produced in a soluble state in cells, the cells are collected by centrifugation after completion of culture, suspended in an aqueous buffer, then disrupted using a sonicator, French press, Manton Gaulin homogenizer, Dynomill, or such to obtain a cell-free extract.

A purified protein can be prepared from the supernatant obtained by centrifugation of the cell-free extract by using, alone or in combination, general methods for isolating and purifying enzymes. The general methods include a solvent extraction, a salting-out using ammonium sulfate or such, a desalting, a precipitation using an organic solvent, an anion exchange chromatography using resins such as diethylaminoethyl (DEAE)-Sepharose or DIAION HPA-75 (manufactured by Mitsubishi Kasei Corp.), a cation exchange chromatography using resins such as S-Sepharose FF (manufactured by GE Healthcare Biosciences), a hydrophobic chromatography using resins such as butyl Sepharose and phenyl Sepharose, a gel filtration using a molecular sieve, an affinity chromatography, a chromatofocusing, and an electrophoresis such as isoelectric focusing.

In case the protein is produced in the form of an insoluble body in cells, the cells are similarly collected and disrupted, centrifuged to obtain a precipitate fraction, and after the protein is recovered from the precipitate fraction by an ordinary method, the insoluble body of the protein is solubilized using a protein-denaturing agent.

A purified protein can be prepared by diluting or dialyzing the solubilized solution with a solution containing no protein-denaturing agent or a solution containing a protein-denaturing agent at such a low concentration that the protein is not denatured, constituting the protein to have a normal three-dimensional structure, and then by isolation and purification methods similar to those described above.

In case the protein of the present invention or its derivative such as a glycosylated form is extracellularly secreted, the protein or its derivative such as a glycosylated form can be recovered in the culture supernatant.

Specifically, the culture is treated by similar means as described above such as centrifugation to obtain a soluble fraction, and a purified protein can be prepared from the soluble fraction by using isolation and purification methods similar to those described above.

An example of a protein obtained in the above manner includes a protein comprising the amino acid sequence represented by any one of SEQ ID NOs: 3-37.

Further, the protein of the present invention can be produced as a fusion protein with another protein and purified by using affinity chromatography using a substance having affinity for the fused protein. For example, the protein of the present invention can be produced as a fusion protein with protein A according to the method of Lowe, et al. [Proc. Natl. Acad. Sci. USA, 86, 8227 (1989); Genes Develop., 4, 1288 (1990)] or methods described in JP-A (Kokai) H05-336963 and WO 94/23021, and purified by affinity chromatography using immunoglobulin G.

The protein of the present invention can also be produced as a fusion protein with a Flag peptide and purified by affinity chromatography using an anti-Flag antibody [Proc. Natl. Acad. Sci. USA, 8227 (1989); Genes Develop., 4, 1288 (1990)], or can be produced as a fusion protein with polyhistidine and purified by affinity chromatography using a metal-coordinated resin having high affinity to polyhistidine. Further, the protein can be purified by affinity chromatography using an antibody against the protein itself.

The protein of the present invention can be produced by chemical synthesis methods such as the Fmoc method (the fluorenylmethyloxycarbonyl method) and the tBoc method (the t-butoxycarbonyl method) based on the amino acid sequence information on a protein obtained above. Further, the protein can be chemically synthesized by using peptide synthesizers from Advanced ChemTech, Perkin-Elmer, Pharmacia, Protein Technology Instrument, Synthecell-Vega, PerSeptive, Shimadzu Corporation, and such.

7. Methods for Measuring Glycated Hexapeptides Using the Proteins of the Present Invention The proteins of the present invention have the characteristic of producing hydrogen peroxide by acting on glycated hexapeptides produced from glycated hemoglobin following the action of a protease on the glycated hemoglobin; therefore, they can be used to measure glycated proteins in various types of samples. Specifically, glycated hemoglobin in a sample can be measured by reacting the sample with a protease to produce glycated hexapeptides, reacting the produced glycated hexapeptides with the protein of the present invention, and measuring a substance produced by the reaction between the glycated hexapeptides and the protein of the present invention or a substance consumed in the reaction between the glycated hexapeptides and the protein of the present invention. The reactions relating to measurement of glycated hemoglobin in the sample can be carried out in the aqueous media described below. Glycated hemoglobin in the present invention is, for example, HbA1c.

The measurement methods of the present invention are described below.

(Samples and Components to be Measured)

The sample used in the measurement method of the present invention is not particularly limited so long as it contains glycated hemoglobin, and examples include biological samples such as whole blood, plasma, serum, blood cells, cell samples, urine, spinal fluid, sweat, tear fluid, saliva, skin, mucous membrane, and hair. As a sample, whole blood, plasma, serum, blood cells and such are preferred, and whole blood, blood cells, and such are particularly preferred. Whole blood includes samples of whole blood-derived blood cell fractions admixed with plasma. With regard to these samples, samples subjected to pretreatments such as hemolysis, separation, dilution, concentration, and purification can be used.

The sequence of the three amino acids at the N terminus of the α-chain of hemoglobin is valine-leucine-serine and the sequence of the three amino acids at the N terminus of the β-chain is valine-histidine-leucine. HbA1c is defined as a hemoglobin in which the N-terminal valine residue of the β-chain is specifically glycated. Furthermore, hemoglobin is known to have multiple glycation sites within the molecule including the N terminus of the α-chain (The Journal of Biological Chemistry (1980), 256, 3120-3127).

By making a protease act on a sample containing glycated hemoglobin, glycated amino acids and/or glycated oligopeptides are produced, such as α-FV, α-FVH, and α-F6P which are derived from glycated hemoglobin in which the β-chain N-terminal valine residue is glycated, α-FV, α-glycated valyl leucine (hereinafter, abbreviated as α-FVL), and α-Fructosyl Val-Leu-Ser-Pro-Ala-Asp (SEQ ID NO: 135) which are derived from glycated hemoglobin in which the α-chain N-terminal valine residue is glycated, and ε-FK derived from glycation of the ε-amino group of lysine residues inside the α-chain and/or β-chain.

Furthermore, in case the sample is whole blood, glycated amino acids such as ε-FK are also produced from glycated proteins in the whole blood other than glycated hemoglobin, such as glycated albumin.

Namely, in case a protease is made to act on a sample containing purified hemoglobin or a sample containing whole blood, for example, α-F6P, α-FVH, α-FV, ε-FK, and α-FVL are produced, where α-F6P, α-FVH, and α-FVL are derived from glycated hemoglobin and α-F6P and α-FVH are specifically derived from HbA1c.

Therefore, in case measuring HbA1c, one can specifically measure α-F6P or α-FVH. The proteins of the present invention are highly reactive towards α-F6P; accordingly, HbA1c can be measured effectively.

In the reference measurement procedure for HbA1c set forth by the International Federation of Clinical Chemistry (IFCC), HbA1c is measured by cutting out a glycated N-terminal hexapeptide (α-F6P) from HbA1c by the action of endoprotease Glu-C (V8 protease), and then analyzing α-F6P by HPLC. In currently used enzymatic assays for HbA1c, a glycated dipeptide produced by treating HbA1c with a protease is a target of measurement. This is because most known glycated peptide oxidases do not recognize glycated peptides that are longer than the glycated dipeptide. Accordingly, if one can develop an enzymatic assay that is based on the principle of measuring HbA1c by using glycated hexapeptide as a target of measurement, enzymatic assays that conform to the IFCC reference measurement procedure will become possible, and it is considered to be industrially very meaningful.

(Proteases)

As a protease that can be used in the present invention, any protease can be used so long as it acts on glycated hemoglobin to be measured included in a sample to produce a glycated hexapeptide, and examples include proteases and peptidases such as Endoproteinase Glu-C, V8 Protease, Proteinase K, Proteinase P, Pronase, thermolysin, subtilisin, carboxypeptidase, chymotrypsin, Dispase, papain, ficin, bromelain, and amino peptidase, and particularly preferred examples include Endoproteinase Glu-C and V8 Protease.

The condition for protease treatment of a sample may be any condition as long as it enables action of the protease used on the glycated hemoglobin which is the target of measurement to release α-F6P efficiently within a short period of time. The amount of protease used is selected appropriately according to the content of HbA1c in a sample, treatment conditions, or such, and as an example, Endoproteinase Glu-C (for example, that manufactured by Roche Diagnostics) is added so that the final concentration becomes 0.1 to 50 U/mL, or preferably 1 to 10 U/mL. Other proteases may be added appropriately, if necessary. The pH during protease treatment may be unadjusted, or adjusted to a pH suitable for the action of the protease to be used, such as pH2 to 9, or preferably pH3 to 8, for example, by using a suitable pH-adjusting agent such as hydrochloric acid, acetic acid, sulfuric acid, sodium hydroxide, or potassium hydroxide. The temperature for treatment may be 20° C. to 50° C., and depending on the enzyme used, a higher range such as 45° C. to 70° C. may be used. The time taken for treatment is not limited as long as the time is sufficient for degradation of HbA1c, and examples include 5 seconds to 180 minutes, and preferably 1 to 60 minutes. The obtained solution after treatment is used without further treatment or upon appropriate heating, centrifugation, concentration, dilution, or such, if necessary, and is subjected to the reaction of glycated hexapeptide oxidase as a sample containing glycated hexapeptides.

(Measurement Method)

Glycated hemoglobin to be measured in a sample of the present invention can be measured by sequentially carrying out the following steps (i) to (iii):

(i) producing glycated hexapeptides by reacting glycated hemoglobin in a sample with a protease;

(ii) reacting the produced glycated hexapeptides with the protein of the present invention; and
(iii) measuring a substance produced or consumed in step (ii).

The above-mentioned steps (i) to (iii) can be carried out in an aqueous medium. Examples of the aqueous medium include deionized water, distilled water, and a buffer solution; and, a buffer solution is preferred. Examples of buffer agents to be used in the buffer solution include tris(hydroxymethyl)aminomethane buffer (Tris buffer), a phosphate buffer, a borate buffer, and a Good's buffer.

Examples of Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxy-3-propanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]-glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO) and N-cyclohexyl-3-aminopropanesulfonic acid (CAPS).

The concentration of the buffer solution is not particularly limited as long as it is suitable for measurement, but the concentration is preferably 0.001 mol/L to 2.0 mol/L, and more preferably 0.005 mol/L to 1.0 mol/L.

For the reactions in each step, the reaction temperature is for example, 10° C. to 50° C. and preferably 20° C. to 40° C., and the reaction time is 1 second to 60 minutes and preferably 1 to 10 minutes.

Regarding the measurement method of glycated hemoglobin of the present invention, in the step of reacting a glycated hemoglobin-containing sample with a protease, a denaturing agent of glycated hemoglobin or an oxidizing agent may coexist. Alternatively, a sample containing glycated hemoglobin can be treated with the denaturing agent or the oxidizing agent in advance, and then the treated sample can be subjected to reaction with a protease. The denaturing agent is not particularly limited, as long as it enables the measurement method of the present invention, and examples include a nonionic surfactant, a cationic surfactant, an anionic surfactant, and an amphoteric surfactant. The oxidizing agent is not particularly limited as long as it enables the measurement method of the present invention, and examples include potassium iodate, potassium periodate, and potassium bromate.

The protease does not have to be particularly inactivated after performing step (i) if it does not affect the reaction of step (ii), and heating, cooling, centrifugation, membrane filtration, addition of an inhibitor, or such can be carried out so that the enzyme will not act in step (ii).

In step (ii), products produced in the reaction solution due to the reaction between the glycated hexapeptide and the protein of the present invention include hydrogen peroxide, sugar osone (α-keto aldehyde), and a peptide. Furthermore, in step (ii), a substance consumed by the reaction between the glycated hexapeptide and the protein of the present invention is, for example, an oxygen molecule. Oxygen molecule consumed in step (ii) is measured, for example, by an electrochemical measurement method using an oxygen electrode.

Hydrogen peroxide produced in step (ii) of the present invention can be measured using, for example, an optical technique or an electrochemical technique. Examples of the optical technique include an absorbance method and a luminescence method. Specific examples include an optical determination using a reagent for measuring hydrogen peroxide and an electrochemical determination using a hydrogen peroxide electrode.

A reagent for measuring hydrogen peroxide is a reagent for converting the produced hydrogen peroxide into a detectable substance. Examples of the detectable substance include a dye and a light; and, a dye is preferred.

In case the detectable substance is a dye, the reagent for measuring hydrogen peroxide includes a peroxidative substance such as peroxidase and an oxidative coloring chromogen. Examples of the oxidative coloring chromogen include an oxidative coupling-type chromogen and a leuco chromogen which are described later.

In case the detectable substance is a light, the reagent for measuring hydrogen peroxide includes chemiluminescent substance, which includes a bioluminescent substance. Examples include luminol, isoluminol, lucigenin, an acridinium ester, and an oxalate ester.

In case using a reagent comprising a peroxidative substance such as peroxidase and an oxidative coloring chromogen as a reagent for measuring hydrogen peroxide, hydrogen peroxide can be measured by reacting hydrogen peroxide with the oxidative coloring chromogen in the presence of a peroxidative substance to produce a dye and then measuring the produced dye. Furthermore, in case using a reagent for measuring hydrogen peroxide which comprises a chemiluminescent substance, hydrogen peroxide can be measured by reacting hydrogen peroxide with a chemiluminescent substance to produce a photon and then measuring the produced photon.

An oxidative coupling-type chromogen is a chromogen which reacts with hydrogen peroxide in the presence of a peroxidative substance such as peroxidase to produce a dye by an oxidative coupling reaction. Specific examples of the oxidative coupling-type chromogen include a coupler such as 4-aminoantipyrine, and a phenolic or anilinic hydrogen donor. A coupler and a phenolic or anilinic hydrogen donor compound undergo oxidative coupling in the presence of hydrogen peroxide and a peroxidative substance to produce a dye.

Examples of a coupler include 4-aminoantipyrine (4-AA) and 3-methyl-2-benzothiazolinone hydrazone.

Examples of a phenolic hydrogen donor include phenol, 4-chlorophenol, 3-methylphenol, and 3-hydroxy-2,4,6-triiodobenzoic acid (HTIB).

Examples of an anilinic hydrogen donor include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5- dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl) aniline, N-ethyl-N-(3-methylphenyl)-N'-succinylethylenediamine (EMSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino)ethyl]-2-methoxy-5-methylaniline (Et-MASE).

A leuco chromogen is a chromogen which produces a dye by itself by reacting with hydrogen peroxide in the presence of a peroxidative substance such as peroxidase. Specific examples include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 10-(carboxymethylaminocarbonyl)-3,7-bis(dimethylamino)phenothiazine sodium salt (DA-67), 4,4'-bis(dimethylamino)diphenylamine, bis[3-bis(4-chlorophenyl)methyl-4-dimethylaminophenyl]amine (BCMA), N,N,N',N',N'',N''-hexa-3-sulfopropyl-4,4',4''-triaminotriphenylmethane (TPM-PS), diaminobentidine, hydroxyphenylpropionic acid, tetramethylbentidine, and orthophenylenediamine.

In the measurement of hydrogen peroxide, the concentration of the peroxidative substance is not particularly limited as long as it is suitable for measurement; and, in case peroxidase is used as a peroxidative substance, the concentration is preferably 1 U/mL to 100 U/mL and more preferably 2 U/mL to 50 U/mL. The concentration of the oxidative coloring chromogen is not particularly limited as long as it is suitable for measurement; and, it is preferably 0.01 g/L to 10 g/L and more preferably 0.02 g/L to 5 g/L.

In case hydrogen peroxide is measured using a hydrogen peroxide electrode, the electrode to be used is not particularly limited as long as it is a material that allows transfer of electrons with the hydrogen peroxide, and examples include platinum, gold, and silver. As the method for measurement, known methods such as amperometry, potentiometry, and coulometry can be used. By interposing an electron-transfer substance in the reaction between the electrode and the oxidase or substrate, the resulting oxidation or reduction current or its electrical quantity can also be measured.

Any substance having a function of transferring electrons can be used as an electron-transfer substance, and examples include substances such as a ferrocene derivative and a quinone derivative. Furthermore, by interposing an electron-transfer substance between the electrode and the hydrogen peroxide produced by the oxidase reaction, the resulting oxidation or reduction current or its electrical quantity can be measured.

In step (ii), a sugar osone (an α-keto aldehyde) is produced together with hydrogen peroxide; therefore, glycated hemoglobin in a sample can also be measured by measuring the produced sugar osone (an α-keto aldehyde). By making glucose oxidase act on the α-keto aldehyde and by measuring the produced hydrogen peroxide as well, highly sensitive measurements can be taken (JP-A (Kokai) 2000-333696).

(Methods for Preparing Samples)

A sample containing the glycated protein to be measured can be separated from a biological sample, as necessary. Examples of a separation method include a centrifugation, a filtration, and a method using blood cell separation membrane. For example, a method of separation by centrifugation enables a separation of whole blood into blood cells and plasma or serum. As necessary, the blood cells can be washed with an isotonic solution such as a physiological saline solution to obtain washed blood cells from which plasma-derived components have been removed.

In case using blood cells as a sample, hemolysis can be carried out by diluting a sample containing blood cells such as whole blood, blood cells, or washed blood cells using a hypotonic solution. Any hypotonic solution can be used so long as it can cause hemolysis of blood cells; examples include water and a buffer solution, and the hypotonic solution preferably contains an additive such as a surfactant. Examples of surfactant include a nonionic surfactant, a cationic surfactant, an anionic surfactant, and an amphoteric surfactant.

A method for preparing washed blood cells includes the following method.

Blood is collected from healthy individuals and diabetes patients, and mixed by overturning, and then subjected to centrifugation (3,000 rpm) at 25° C. for five minutes. After centrifugation, the supernatant plasma is removed. For one part of the lower-part blood cell layer, four parts of physiological saline solution is added, and the mixture is mixed by overturning and subjected to centrifugation (3,000 rpm) at 25° C. for five minutes. After centrifugation, the supernatant physiological saline solution is removed. After repeating this washing operation three times, nine parts of distilled water is added to one part of the washed blood cell layer to yield washed blood cells.

(Reagents and Kits for Measuring Glycated Hemoglobin)

The reagent for measuring glycated hemoglobin and kit for measuring glycated hemoglobin of the present invention can be used in the method for measuring glycated hemoglobin of the present invention. The reagent for measuring glycated hemoglobin of the present invention can take the form of a kit, as a form suitable for storage, transport, and distribution. Examples of the form of the kit include a two-reagent system and a three-reagent system.

The reagent for measuring glycated hemoglobin of the present invention comprises protease and the protein of the present invention. Furthermore, the reagent for measuring glycated hemoglobin of the present invention can comprise a reagent for measuring a product produced by the reaction between the protein of the present invention and a glycated hexapeptide produced from glycated hemoglobin. Examples of a product produced by the reaction between the protein of the present invention and a glycated hexapeptide produced from glycated hemoglobin include hydrogen peroxide, sugar osone (an α-keto aldehyde), and a peptide (Val-His-Leu-Thr-Pro-Glu; SEQ ID NO: 134). Examples of the reagent for measuring a product produced by the reaction between the protein of the present invention and a glycated hexapeptide produced from glycated hemoglobin include a reagent for measuring hydrogen peroxide, a reagent for measuring a sugar osone (an α-keto aldehyde), and a reagent for measuring a peptide (Val-His-Leu-Thr-Pro-Glu; SEQ ID NO: 134), and a reagent for measuring hydrogen peroxide are preferred.

Examples of the kits of the present invention for measuring glycated hemoglobin to be measured include the kits of the following embodiments:

Kit 1 (Two-Reagent System Kit)

A kit comprising the following two reagents:
(1) a reagent comprising a protease; and
(2) a reagent comprising the protein of the present invention.

Kit 2 (Two-Reagent System Kit)

A kit comprising the following two reagents:
(1) a reagent comprising a protease; and
(2) a reagent comprising a protein of the present invention and a reagent for measuring a product produced by the reaction between the protein of the present invention and a glycated hexapeptide produced from glycated hemoglobin.

Kit 3 (Two-Reagent System Kit)

A kit comprising the following two reagents:

(1) a reagent comprising a protease and a reagent for measuring a product produced by the reaction between the protein of the present invention and a glycated hexapeptide produced from glycated hemoglobin; and (2) a reagent comprising the protein of the present invention.

Kit 4 (Two-Reagent System Kit)

A kit comprising the following two reagents:

(1) a reagent comprising a protease and a reagent for measuring a product produced by the reaction between the protein of the present invention and a glycated hexapeptide produced from glycated hemoglobin; and (2) a reagent comprising the protein of the present invention and a reagent for measuring a product produced by the reaction between the protein of the present invention and a glycated hexapeptide produced from glycated hemoglobin.

Kit 5 (Three-Reagent System Kit)

A kit comprising the following three reagents:

(1) a reagent comprising a protease;

(2) a reagent comprising the protein of the present invention; and (3) a reagent for measuring a product produced by the reaction between the protein of the present invention and a glycated hexapeptide produced from glycated hemoglobin.

Kit 6 (Three-Reagent System Kit)

A kit comprising the following three reagents:

(1) a reagent comprising a protease and a reagent for measuring a product produced by the reaction between the protein of the present invention and a glycated hexapeptide produced from glycated hemoglobin;

(2) a reagent comprising the protein of the present invention; and (3) a reagent for measuring a product produced by the reaction between the protein of the present invention and a glycated hexapeptide produced from glycated hemoglobin.

Kit 7 (Three-Reagent System Kit)

A kit comprising the following three reagents:

(1) a reagent comprising a protease;

(2) a reagent comprising the protein of the present invention and a reagent for measuring a product produced by the reaction between the protein of the present invention and a glycated hexapeptide produced from glycated hemoglobin; and (3) a reagent for measuring a product produced by the reaction between the protein of the present invention and a glycated hexapeptide produced from glycated hemoglobin.

Kit 8 (Three-Reagent System Kit)

A kit comprising the following three reagents:

(1) a reagent comprising a protease and a reagent for measuring a product produced by the reaction between the protein of the present invention and a glycated hexapeptide produced from glycated hemoglobin;

(2) a reagent comprising the protein of the present invention and a reagent for measuring a product produced by the reaction between the protein of the present invention and a glycated hexapeptide produced from glycated hemoglobin; and (3) a reagent for measuring a product produced by the reaction between the protein of the present invention and a glycated hexapeptide produced from glycated hemoglobin.

Examples of each of the protease, the protein of the present invention, glycated hemoglobin, and the reagent for measuring a product produced by the reaction between the protein of the present invention and a glycated hexapeptide produced from glycated hemoglobin used in the reagent and kit for measurement of the present invention include those mentioned above.

In case the reagent for measuring a product produced by the reaction between the protein of the present invention and a glycated hexapeptide produced from glycated hemoglobin is a reagent for measuring hydrogen peroxide, examples of the reagent for measuring hydrogen peroxide include the aforementioned reagents for measuring hydrogen peroxide. In case an oxidative coupling-type chromogen is used as a reagent for measuring hydrogen peroxide, a coupler and a phenolic or anilinic hydrogen donor can be included in the same reagent; and, they are preferably included in separate reagents.

The reagent for measurement and kit for measurement of the present invention can further comprise a standard substance for measurement such as a standard protein.

As necessary, the reagent for measurement and kit for measurement of the present invention can comprise a buffer, a stabilizer, a preservative, an agent for removing affecting substance, an agent for suppressing nonspecific reaction, a surfactant, and such. Examples of the buffer include the aforementioned buffers. Examples of the stabilizer include ethylenediaminetetraacetic acid (EDTA), sucrose, calcium chloride, amino acids, albumin, dextran, and salts such as calcium acetate. Examples of the preservative include sodium azide and an antibiotic. Examples of the agent for removing affecting substance include ascorbate oxidase for eliminating the effect of ascorbic acid. Examples of the agent for suppressing nonspecific reaction include a polymeric compound such as dextran sulfate. Examples of the surfactant include a nonionic surfactant, a cationic surfactant, an anionic surfactant, and an amphoteric surfactant.

The reagent and kit for measurement of the present invention can be in a freeze-dried state or in a state dissolved in a reaction solution. In case using a kit in a freeze-dried state, the kit can be used after dissolution in an aforementioned aqueous medium or reaction solution. In case using a kit in a freeze-dried state, a reagent for dissolving the freeze-dried reagent or such can be comprised in the kit, as necessary.

The protease content in the kit for measurement of the present invention is preferably a content which will give a concentration of 0.01 U/mL to 1,000,000 U/mL, more preferably a concentration of 0.1 U/mL to 100,000 U/mL in a state dissolved in an aqueous medium.

The content of the protein of the present invention in the kit for measurement of the present invention is preferably a content which will give a concentration of 0.01 U/mL to 10,000 U/mL, more preferably a concentration of 0.1 U/mL to 1,000 U/mL in a state dissolved in an aqueous medium.

In case a reagent comprising peroxidase and an oxidative coupling-type chromogen is used as a reagent for measuring hydrogen peroxide, the contents of peroxidase and an oxidative coupling-type chromogen in a kit are preferably contents which will give concentrations of 1 U/mL to 600 U/mL and 0.5 g/L to 40 g/L, respectively, and more preferably concentrations of 2 U/mL to 150 U/mL and 1 g/L to 20 g/L, respectively, in a state dissolved in an aqueous medium.

(Methods for Directly Measuring Glycated Hemoglobin)

The protein of the present invention includes that having the activity of directly oxidizing glycated hemoglobin to produce hydrogen peroxide (hereinafter, referred to as glycated hemoglobin oxidase activity). By using a protein having the glycated hemoglobin oxidase activity (hereinafter, referred to as glycated hemoglobin oxidase), glycated hemoglobin can be directly measured by direct action of the glycated hemoglobin oxidase of the present invention on glycated hemoglobin, without action of a protease on the glycated hemoglobin, to produce hydrogen peroxide, followed by measurement of this hydrogen peroxide.

The glycated hemoglobin oxidase of the present invention may be any glycated hexapeptide oxidase having the ability to directly oxidize glycated hemoglobin, and examples include the following glycated hexapeptide oxidases:
[1] a protein comprising the amino acid sequence represented by any one of SEQ ID NOs: 6 to 37; and
[2] a protein comprising an amino acid sequence having a homology of 90% or more, for example, 94% or more, preferably 95% or more, more preferably 96% or more, even more preferably 97% or more, yet even more preferably 98% or more, and particularly preferably 99% or more to the amino acid sequences represented by SEQ ID NOs: 6 to 37, and having glycated hemoglobin oxidase activity.

Regarding the method for directly measuring glycated hemoglobin of the present invention, in the step of reacting a glycated hemoglobin-containing sample with a glycated hemoglobin oxidase, a denaturing agent or an oxidizing agent may coexist. Alternatively, a sample containing glycated hemoglobin can be treated with a denaturing agent or an oxidizing agent in advance, and then the treated sample can be subjected to reaction with a glycated hemoglobin oxidase. Examples of the denaturing agent and oxidizing agent include the aforementioned denaturing agents and oxidizing agents, respectively.

(Methods for Measuring Glycated Hemoglobin Oxidase Activity)

Glycated hemoglobin oxidase activity can be measured, for example, by the following method.

(Reagents for Activity Measurements)
Solution A: 0.1 mol/L MOPS buffer solution (pH6.8)
Solution B: 24 mmol/L solution of DA-67 in DMF
Solution C: 1 kU/L solution of peroxidase in 0.01 mol/L phosphate buffer solution (pH7.0)
Solution D: 10 g/L human hemocyte-derived hemolysate sample
Solution E: 5 g/L aqueous solution of potassium iodate and 50% (v/v) AMPHITOL 20N (amphoteric surfactant)
Solution F: 0.5 to 1.0 U/mL solution of glycated hemoglobin oxidase in 10 mmol/L phosphate buffer solution (pH7.0)

(Measurement Procedure)
(i) 2 µL of Solution E is mixed into 20 µL of Solution D, and this is incubated at 37° C. for 10 to 30 minutes.
(ii) To 10 mL of Solution A, 12.6 µL of Solution B and 35 µL of Solution C are added, and the obtained solution is dispensed into a 96-well microplate at 190 µL per sample. Then 20 µL of a solution produced by mixing Solutions D and E, and 20 µL of Solution F are added and mixed. The absorbance of the solution immediately after mixing is measured at 660 nm (main wavelength)/750 nm (sub-wavelength) using a fully automated microplate EIA analyzer, and then an enzymatic reaction is carried out by incubating at 37° C. for 60 to 120 minutes, the absorbance of the obtained solution is measured at 660 nm (main wavelength)/750 nm (sub-wavelength), and the change in absorbance before and after the enzymatic reaction is determined.

The above-mentioned steps can be carried out in an aqueous medium. Examples of the aqueous medium include the aforementioned aqueous medium (preferably a buffer solution), and the concentration of the buffer solution may be, for example, the aforementioned concentration of the buffer solution.

For the reactions in each step, the reaction temperature is for example, 10° C. to 50° C. and preferably 20° C. to 40° C., and the reaction time is 1 second to 120 minutes, preferably 1 to 90 minutes, and particularly preferably 1 to 60 minutes.

(Reagents and Kits for Direct Measurement of Glycated Hemoglobin)

The reagent for measuring glycated hemoglobin of the present invention include reagent for directly measuring glycated hemoglobin. The reagent for directly measuring glycated hemoglobin of the present invention can be used in the method for measuring glycated hemoglobin of the present invention. By using the reagent for direct measurement of glycated hemoglobin of the present invention, glycated hemoglobin can be measured without a use of a protease through measurement of a substance produced or consumed by direct oxidation of glycated hemoglobin. The reagent for directly measuring glycated hemoglobin of the present invention can take the form of a kit, as a form suitable for storage, transport, and distribution. Examples of the form of the kit include a two-reagent system and a three-reagent system.

The reagent of the present invention for directly measuring glycated hemoglobin comprises glycated hemoglobin oxidase of the present invention. Furthermore, the reagent of the present invention for directly measuring glycated hemoglobin can comprise a reagent for measuring a product produced by the reaction between the glycated hemoglobin oxidase of the present invention and glycated hemoglobin. Examples of the product produced by the reaction between the glycated hemoglobin oxidase of the present invention and glycated hemoglobin include hydrogen peroxide, sugar osone (an α-keto aldehyde), and hemoglobin. Examples of the reagent for measuring a product produced by the reaction between the glycated hemoglobin oxidase of the present invention and glycated hemoglobin include a reagent for measuring hydrogen peroxide, a reagent for measuring a sugar osone (an α-keto aldehyde), and a reagent for measuring hemoglobin; and a reagent for measuring hydrogen peroxide is preferred.

Examples of the kit of the present invention for directly measuring glycated hemoglobin include the kit of the following embodiments:
A kit comprising the following two reagents:
(1) a reagent comprising a glycated hemoglobin oxidase; and
(2) a reagent for measuring a product produced by the reaction between the glycated hemoglobin oxidase and glycated hemoglobin.

Examples of the glycated hemoglobin oxidase and the reagent for measuring a product produced by the reaction between a glycated hemoglobin oxidase and glycated hemoglobin used in the reagent and kit of the present invention for direct measurement include those mentioned above, respectively.

In case the reagent for measuring a product produced by the reaction between the glycated hemoglobin oxidase of the present invention and glycated hemoglobin is a reagent for measuring hydrogen peroxide, examples of the reagent for measuring hydrogen peroxide include the aforementioned reagents for measuring hydrogen peroxide. In case an oxidative coupling-type chromogen is used as a reagent for measuring hydrogen peroxide, a coupler and a phenolic or anilinic hydrogen donor can be included in the same reagent; and they are preferably included in separate reagents.

The reagent for direct measurement and kit for direct measurement of the present invention can further comprise a standard for measurement such as standard proteins.

As necessary, the reagent for direct measurement and kit for direct measurement of the present invention can individually comprise the aforementioned buffer, stabilizer, preservative, agent for removing affecting substances, agent for suppressing nonspecific reactions, surfactant, and such.

The reagent for direct measurement and kit for direct measurement of the present invention can be in a freeze-dried state or in a state dissolved in a reaction solution. In case of using a kit in a freeze-dried state, the kit can be used after dissolution in an aforementioned aqueous medium or reaction solution. In case of using a kit in a freeze-dried state, a reagent for dissolving the freeze-dried reagent or such can be comprised in the kit, as necessary.

The content of glycated hemoglobin oxidase in the kit for direct measurement of the present invention is preferably a content which will give a concentration of 0.01 U/mL to 1,000,000 U/mL, more preferably a concentration of 0.1 U/mL to 100,000 U/mL in a state dissolved in an aqueous medium.

In case a reagent comprising peroxidase and an oxidative coupling-type chromogen is used as a reagent for measuring hydrogen peroxide, the contents of peroxidase and an oxidative coupling-type chromogen in a kit are preferably contents which will give concentrations of 1 U/mL to 600 U/mL and 0.5 g/L to 40 g/L, respectively, and more preferably concentrations of 2 U/mL to 150 U/mL and 1 g/L to 20 g/L, respectively, in a state dissolved in an aqueous medium.

All prior art references cited herein are incorporated by reference into this description.

EXAMPLES

Herein below, Examples are indicated, but the present invention is not to be construed as being limited thereto. Reagents, enzymes, and instruments of the following manufacturers were used in the present Examples:
potassium dihydrogenphosphate (Wako Pure Chemical Industries), dibasic potassium phosphate (Wako Pure Chemical Industries), DA-67 (manufactured by Wako Pure Chemical Industries), peroxidase (manufactured by TOYOBO), α-glycated valine (manufactured by Peptide Institute Inc.), α-glycated hexapeptide (manufactured by Peptide Institute Inc.), MOPS (manufactured by Dojindo Laboratories), dimethylformamide (manufactured by Wako Pure Chemical Industries), potassium iodate (manufactured by Wako Pure Chemical Industries), 4-aminoantipyrine (4-AA) (manufactured by Wako Pure Chemical Industries), EMSE (manufactured by Daito Chemix Corporation), manganese chloride tetrahydrate (manufactured by Wako Pure Chemical Industries), isopropyl-β-thiogalactoside (IPTG) (manufactured by Nacalai Tesque Inc.), potassium chloride (manufactured by Wako Pure Chemical Industries), imidazole (manufactured by Wako Pure Chemical Industries), tris(hydroxymethyl)aminomethane hydrochloride salt (Tris-HCl) (manufactured by Wako Pure Chemical Industries), Luria-Bertani miller medium (LB medium) (manufactured by Becton, Dickinson and Company), sodium ampicillin (manufactured by Wako Pure Chemical Industries), KOD-Plus- (DNA polymerase; manufactured by TOYOBO), Dpn I (restriction enzyme; manufactured by New England Biolabs), Bgl II (restriction enzyme; manufactured by Roche Applied Science), Xho I (restriction enzyme; manufactured by Roche Applied Science), and Competent high DH5α($E.$ $coli$ competent cells; manufactured by TOYOBO).

Example 1

Construction of FPOX-15 Expression Plasmid and FPOX-15-Expressing $E.$ $coli$ Strain (Production of the pTrc-FPOX-9 Expression Plasmid)

Glycated peptide oxidase FPOX-9-expressing $E.$ $coli$ XL1-Blue MRF strain deposited under Accession No. FERM BP-11026 was inoculated into 3 mL of LB medium containing 50 mg/L ampicillin, and this was shake-cultured overnight at 37° C. The culture solution was centrifuged at 8,000 rpm for 2 minutes to collect the bacterial cells. Expression plasmid pTrc-FPOX-9 which expresses glycated peptide oxidase FPOX-9 having the amino acid sequence represented by SEQ ID NO: 2 inside $E.$ $coli$ cells was extracted from the obtained bacterial cells using "Wizard Plus SV Minipreps DNA Purification" manufactured by Promega.

Using the method described in International Publication No. WO 2010/041715 pamphlet, pTrc-FPOX-15 expression plasmid which expresses FPOX-15 having the amino acid sequence represented by SEQ ID NO: 1, which has excellent thermostability and reaction specificity towards α-FVH which is a partial structure of a glycated hexapeptide, was produced by the above-mentioned plasmid pTrc-FPOX-9.

(Method for Site-Specific Amino Acid Substitution)

Using the pTrc-FPOX-15 expression plasmid as a template DNA and a primer pair in which a codon of the amino acid targeted for mutation is replaced with a codon corresponding to the substituting amino acid, PCR products (expression plasmids containing the mutation) were amplified using the following reagent composition and PCR conditions. PCR was carried out by following the protocol provided with DNA polymerase "KOD-Plus-", a PCR kit manufactured by TOYOBO.

(Reagent Composition)

| | |
|---|---|
| reaction buffer | |
| template DNA | 1 to 2 ng/μL |
| forward primer | 0.3 μmol/L |
| reverse primer | 0.3 μmol/L |
| dNTP solution mixture | 0.2 mmol/L each |
| MgSO$_4$ | 1 mmol/L |
| DNA polymerase | 0.02 U/μL |
| sterilized water | added to fill up to 50 μL |

(PCR Conditions)
1. 94° C. for 2 minutes
2. 98° C. for 15 seconds
3. 60° C. for 30 seconds
4. 68° C. for 6 minutes
5. repeat 2 to 4 (for a total of 30 cycles)
6. 68° C. for 10 minutes To 50 μL of the PCR product, 1 μL of "restriction enzyme Dpn I" manufactured by New England Biolabs was added, and by incubating this at 37° C. for 1 hour, template DNA was degraded. The PCR product subjected to the restriction enzyme treatment was purified using "Wizard SV Gel and PCR Clean-Up System" manufactured by Promega, and a portion of this sample was used to transform $E.$ $coli$ competent cells "Competent high DH5α" manufactured by TOYOBO. Colonies grown on LB agar medium containing 50 mg/L ampicillin were selected, and plasmids were extracted using "Wizard Plus SV Minipreps DNA Purification" manufactured by Promega.

Sequence analysis was performed on the extracted plasmids using a DNA sequencer to confirm the construction of plasmids containing a DNA comprising the nucleotide sequence represented by SEQ ID NO: 39 which encodes FPOX-15. For the sequence analysis, primers that have DNAs comprising the nucleotide sequences represented by SEQ ID NOs: 87 and 88, which reflect the nucleotide sequences just before and after the multicloning site of the pTrc99a vector, respectively, and a primer that has a DNA comprising the nucleotide sequence represented by SEQ ID NO: 89 which is the nucleotide sequence of positions 530 to 548 in the nucleotide sequence of FPOX-15 having the nucleotide sequence represented by SEQ ID NO: 39 were used.

Example 2

Production of FPOX-15 and the Proteins of the Present Invention, and Measurement of Glycated Hexapeptide Oxidase Activities of FPOX-15 and the Proteins of the Present Invention Regarding the mutants that showed significant activity in the enzyme modification process, purified samples were prepared by following the method of expression and purification of the glycated peptide oxidase FPOX-15, described in International Publication No. WO 2010/041715 pamphlet, to evaluate their activities.

Since the glycated hexapeptide oxidases and glycated hemoglobin oxidases which are the proteins of the present invention carry flavin-adenine dinucleotide (hereinafter written as FAD) as a coenzyme, their protein concentrations can be measured by the following method, in which the absorbance at 452 nm, derived specifically from FAD, is measured.

Commercially available glycated peptide oxidase FPOX-CE (manufactured by Kikkoman Co.) was diluted using a 10 mmol/L phosphate buffer solution to prepare each of the FPOX-CE solutions having each of the following concentrations: 0.7, 1.4, 2.8, 5.6, and 11.2 mg/mL. The FPOX-CE solutions prepared at each of the concentrations were subjected to absorbance measurements at 452 nm (main wavelength)/600 nm (sub-wavelength) using the "Ultrospec 2100 pro" spectrophotometer manufactured by GE Healthcare to prepare a calibration curve indicating the relationship between FPOX-CE concentration and absorbance. The same method was used to measure the absorbance of the purified protein, except that purified proteins were used as a sample instead of the series of diluted solutions of FPOX-CE (manufactured by Kikkoman Co.). Protein concentrations of the purified proteins were determined by comparing the measured absorbance values for the purified proteins with the values of the above-described calibration curve.

The glycated hexapeptide oxidase activity of the obtained glycated hemoglobin oxidase was evaluated using the following reagents and the following measurement procedure.
(Reagents for Activity Measurements)
Solution A: 50 mmol/L phosphate buffer solution (pH7.0)
Solution B: 24 mmol/L solution of DA-67 in DMF
Solution C: 1 kU/L peroxidase in 10 mmol/L phosphate buffer solution (pH7.0)
Solution D: 1 mmol/L aqueous solution of α-F6P
Solution E: 0.1 mg/mL solution of glycated hexapeptide oxidase of the present invention in 10 mmol/L phosphate buffer solution (pH7.0)

(Measurement Procedure)

To 10 mL of solution A, 12.64 of solution B and 354 of solution C were added, and the obtained solution was dispensed into a 96-well plate at 1904 per sample. 204 of solution D and 104 of solution E were added and mixed, and this was allowed to react at 30° C. for 30 minutes. The absorbance of the solution before reaction $Abs_{(before\ reaction)}$ at 660 nm (main wavelength)/750 nm (sub-wavelength), and the absorbance after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$. Absorbance change for the blank $\Delta'Abs_{(blank)}$ was determined by performing a similar method, except that distilled water was used instead of solution E (protein solution). The reaction absorbance $\Delta Abs_{(reaction)}$ was obtained by subtracting the absorbance change for the blank $\Delta'Abs_{(blank)}$ from the absorbance change due to the reaction $\Delta'Abs_{(reaction)}$.

In the aforementioned measurement system, various concentrations of hydrogen peroxide were used instead of solution D to perform similar reactions, and the change in absorbance before and after the reaction at 660 nm (main wavelength)/750 (sub-wavelength) was measured to prepare a calibration curve that shows the relationship between hydrogen peroxide concentration and absorbance change. Solution D (substrate solution) and solution E (protein solution) were used to perform an enzyme reaction, and by comparing the absorbance change accompanying the enzyme reaction with the values in the aforementioned calibration curve, concentration of hydrogen peroxide produced in the enzymatic reaction was determined. In the enzyme reaction performed using α-F6P as a substrate, the enzyme activity that produces 1 μmol of hydrogen peroxide in one minute is defined as 1 U. Based on both of the previously determined purified protein concentration and the enzyme activity defined as described above, the activity of the purified protein used was presented as specific activity (U/mg), which is the activity possessed by 1 mg of purified enzyme. Furthermore, the activity of the purified enzyme used was presented as specific activity (U/mL), which is the total activity per 1 mL of the purified protein solution, based on the aforementioned specific activity (U/mg).
(Site-Specific Amino Acid Substitutions)

Using pTrc-FPOX-15 and the expression plasmid derived from it as a template DNA, site-specific amino acid substitutions were introduced by the method described in Example 1. Site-specific saturation mutagenesis was performed by a method similar to the method for introducing site-specific amino acid substitution described in Example 1, and as exemplified by the nucleotide sequences of SEQ ID NOs: 90 and 91, primers in which the targeted amino acid positions were replaced with NNS were used. N indicates that any one of the nucleotides, A, T, G, and C, is included randomly, and S indicates that either one of the nucleotides, G and C, is included randomly.

The prepared mutant glycated peptide oxidases and the constructed mutant glycated peptide oxidase library were evaluated by the following method. Colonies (transformants) that grew in an overnight culture on a plate containing an LB agar medium supplemented with 50 mg/L ampicillin were selected. They were shake-cultured at 37° C. for 12 hours using a 96-well microplate containing 100 μL of LB medium supplemented with 50 mg/L of ampicillin. 10 μL of "BugBuster (registered trademark) Protein Extraction Reagent (hereinafter written as BugBuster)" manufactured by Novagen was added to 2 μL of the culture solution to lyse the bacterial cells, and after centrifugation, the supernatant was used as a sample.

The α-FV oxidase activities of the mutant glycated peptide oxidases included in the prepared mutant glycated peptide oxidase library were evaluated using the following reagents and the following measurement procedure.
(Reagents for Activity Evaluation)

| | |
|---|---|
| 50 mmol/L phosphate buffer solution (pH 7.0) | 10 mL |
| 10 g/L aqueous solution of 4-AA | 100 μL |
| 10 g/L aqueous solution of EMSE | 100 μL |
| 1 kU/L solution of peroxidase in 10 mmol/L phosphate buffer solution (pH 7.0) | 35 μL |
| 80 mmol/L α-FV | 62.5 μL |

(Measurement Procedure)

100 μL each of the reagents for evaluation were dispensed into each well of a 96-well microplate, 10 μL of the sample was additionally added, and this was incubated at 30° C. for 30 minutes. Measurements were carried out at 550 nm (main wavelength)/650 nm (sub-wavelength) before and after incubation, and the clones showing larger absorbance changes were selected.

2 μL of culture solutions of the clones having significant α-FV activity were added to a 96-well microplate containing 200 μL of LB medium supplemented with 50 mg/L of ampicillin, and this was shake-cultured at 37° C. for 2 hours. After culturing, 2 μL of 10 mmol/L IPTG (manufactured by Nacalai Tesque Inc.) was added, and this was additionally shake-cultured at 37° C. for 5 hours. After culturing, the bacterial cells were collected by centrifugation. 20 μL of BugBuster was added to the obtained bacterial cells, and after bacterial cell lysis and centrifugation, the supernatant was used as a sample to measure the glycated hexapeptide oxidase activity.

For screening of mutants, glycated hexapeptide oxidase activity on α-F6P was evaluated using the following reagents and measurement procedure.
(Reagents for Activity Evaluation)

| | |
|---|---|
| 50 mmol/L phosphate buffer solution (pH 7.0) | 10 mL |
| 24 mmol/L solution of DA-67 in DMF | 12.6 μL |
| 1 kU/L solution of peroxidase in 10 mmol/L phosphate buffer solution (pH 7.0) | 35 μL |
| 0.25 mmol/L aqueous solution of α-F6P | 720 μL |

(Measurement Procedure)

30 μL each of the reagents for activity evaluation were dispensed into a 384-well plate, 5 μL of the sample was added, and this was incubated at 30° C. for 1 hour. Each well was observed after incubation and clones with significantly strong color development were selected.

Meanwhile, plasmids were prepared from each transformant, and the nucleotide sequence of the FPOX gene portion was verified using a DNA sequencer according to the method of Example 1. Then the changes in enzyme activity were correlated with the changes in the nucleotide sequences (amino acid sequences).

Site-specific saturation mutations were introduced to the pTrc-FPOX-15 plasmid which expresses FPOX-15, by using a primer pair which has DNAs comprising the nucleotide sequences represented by SEQ ID NOs: 90 and 91. Using the plasmid introduced with the site-specific saturation mutations, a group of mutants comprising proteins in which arginine at position 61 of FPOX-15 is substituted with 19 types of amino acids other than arginine was constructed. The group of mutants constructed was evaluated using α-FV and α-F6P activities as an index, and glycated hexapeptide oxidase activities of each of the mutants were found to be improved remarkably as shown in Table 1. Particularly, among the group of mutants, the mutant whose position 61 had been substituted with glycine (hereinafter, referred to as FPOX-16) had α-F6P activity 63.9 times as FPOX-15, and the mutant whose position 61 had been substituted with serine (hereinafter, referred to as FPOX-17) had α-F6P activity 67.7 times as FPOX-15, and their glycated hexapeptide oxidase activity was increased. The amino acid sequences of FPOX-16 and FPOX-17 are shown in SEQ ID NOs: 3 and 4, respectively.

TABLE 1

| | Position 61 | Activity ratio* | |
|---|---|---|---|
| FPOX-15 | Arg (WT) | 1.0 | |
| | Gly | 63.9 | ... FPOX-16 |
| | Ala | 29.4 | |
| | Val | 11.0 | |
| | Leu | 3.8 | |
| | Ser | 67.7 | ... FPOX-17 |
| | Cys | 10.4 | |
| | Met | 6.9 | |
| | Thr | 32.3 | |
| | Pro | 18.0 | |
| | Asn | 41.1 | |
| | Gln | 16.2 | |
| | Asp | 46.5 | |
| | Glu | 0.0 | |

*Activity ratio when the glycated hexapeptide oxidase activity of FPOX-15 is defined as 1

Next, a mutant library was constructed by introducing site-specific saturation mutations to FPOX-16, which targeted arginine at position 63, using a primer pair having DNAs comprising the nucleotide sequences represented by SEQ ID NOs: 92 and 93. As a result of evaluating the library using oxidase activity on α-FV and α-F6P as an index, mutants with substitution to alanine, proline, or glycine were obtained. As shown in Table 2, the above-mentioned mutants showed glycated hexapeptide oxidase activity on α-F6P 2 to 2.7 times as that of FPOX-16. Especially, glycated hexapeptide oxidase activity showed the greatest increase by substitution with alanine.

TABLE 2

| Template | Additional mutation | Activity ratio with respect to FPOX-16* | Activity ratio with respect to FPOX-15** |
|---|---|---|---|
| FPOX-16 | — | 1.0 | 63.9 |
| | R63G | 2.0 | 128 |
| | R63P | 2.2 | 143 |
| | R63A | 2.7 | 171 |

*Activity ratio when the glycated hexapeptide oxidase activity of FPOX-16 is defined as 1
**Activity ratio when the glycated hexapeptide oxidase activity of FPOX-15 is defined as 1

Screening using the mutant library constructed by introducing site-specific saturation mutations to FPOX-16 confirmed that substitution of arginine at position 63 with alanine improves glycated hexapeptide oxidase activity, and this mutation was introduced to FPOX-17 using a primer pair having the DNAs comprising the nucleotide sequences represented by SEQ ID NOs: 94 and 95, to obtain the mutant in which arginine at position 63 in the amino acid sequence of FPOX-17 has been substituted with alanine. Next, leucine at position 62, which is positioned between amino acids at positions 61 and 63 found to contribute to increase in glycated hexapeptide oxidase activity, was subjected to saturation mutagenesis using a primer pair having the DNAs comprising the nucleotide sequences of SEQ ID NOs: 96 and 97 to construct a mutant library by introduction of the site-specific saturation mutations. As a result of evaluating the library using oxidase activity on α-FV and α-F6P as an index, a mutant with substitution to glycine (hereinafter, referred to as FPOX-18) was obtained. As shown in Table 3, the above-mentioned mutation caused the oxidase activity on α-F6P to increase by 2.8 times as that of FPOX-17. The amino acid sequences of FPOX-17 and FPOX-18 are shown in SEQ ID NOs: 4 and 5, respectively.

TABLE 3

| Template | Additional mutation(s) | Activity ratio with respect to FPOX-17* | Activity ratio with respect to FPOX-15** | |
|---|---|---|---|---|
| FPOX-17 | — | 1.0 | 67.7 | |
|  | R63A | 2.6 | 178 | |
|  | R63A L62G | 2.8 | 190 | ... FPOX-18 |

*Activity ratio when the glycated hexapeptide oxidase activity of FPOX-17 is defined as 1
**Activity ratio when the glycated hexapeptide oxidase activity of FPOX-15 is defined as 1

By site-specific amino acid substitution, the mutant in which glutamine at position 93 of FPOX-18 has been substituted with glutamic acid by using a primer pair which has DNAs comprising the nucleotide sequences represented by SEQ ID NOs: 98 and 99, and the mutant in which phenylalanine at position 267 has been substituted with tyrosine by using a primer pair which has DNAs comprising the nucleotide sequences represented by SEQ ID NOs: 100 and 101 were obtained. As shown in Table 4, glycated hexapeptide oxidase activity on α-F6P increased 1.3 times and 1.5 times, respectively, as that of FPOX-18.

TABLE 4

| Template | Additional mutation | Activity ratio with respect to FPOX-18* | Activity ratio with respect to FPOX-15** |
|---|---|---|---|
| FPOX-18 | — | 1.0 | 190 |
|  | Q93E | 1.3 | 257 |
|  | F267Y | 1.5 | 282 |

*Activity ratio when the glycated hexapeptide oxidase activity of FPOX-18 is defined as 1
**Activity ratio when the glycated hexapeptide oxidase activity of FPOX-15 is defined as 1

Next, using pTrc-FPOX-18 as a template DNA, introduction of random mutations was examined using glycated hexapeptide oxidase activity as an indicator.
(Construction of Plasmids for Examination of Random Mutations)
First, the pTrc-FPOX-18 plasmid containing a DNA encoding FPOX-18 was obtained by a method similar to that of Example 1. Then, using the plasmid as a template DNA, and by using a primer pair that has DNAs comprising the nucleotide sequences represented by SEQ ID NOs: 102 and 103 to substitute adenine at position 168 in the FPOX-18 gene with guanine by a method similar to the method for introduction of site-specific amino acid substitution of Example 1, a Bgl II restriction enzyme site was introduced without accompanying amino acid substitutions. The obtained modified plasmid is called pTrc-FPOX-18'.

For random mutations, nucleotide substitutions were carried out randomly by PCR using a primer pair that has DNAs comprising the nucleotide sequences represented by SEQ ID NOs: 102 and 104 designed to amplify the region corresponding to amino acid positions 58 to 119 in the FPOX gene included in pTrc-FPOX-18', and using the following reagent composition and PCR conditions. PCR was carried out using Error Prone PCR by partially modifying the protocol of "rTaq DNA polymerase", a PCR kit manufactured by TOYOBO.
(Reagent Composition)

| reaction buffer |  |
|---|---|
| template DNA | 0.2 ng/μL |
| forward primer | 1 μmol/L |
| reverse primer | 1 μmol/L |
| MgCl$_2$ | 7 mmol/L |
| MnCl$_2$ | 0.5 mmol/L |
| dATP | 0.2 mmol/L |
| dTTP | 1 mmol/L |
| dGTP | 0.1 mmol/L |
| dCTP | 1 mmol/L |
| DNA polymerase | 0.04 U/μL |

(PCR Conditions)
1. 94° C. for 3 minutes
2. 94° C. for 30 seconds
3. 50° C. for 30 seconds
4. 72° C. for 30 seconds
5. repeat steps 2 to 4 (total of 45 cycles)
6. 72° C. for 1 minute PCR products containing random nucleotide substitutions were digested using restriction enzymes Bgl II and Xho I, this was then purified using "Wizard SV Gel and PCR Clean-Up System" to obtain digestion products. The aforementioned digestion products were ligated to pTrc-FPOX-18' treated with the same restriction enzymes by using the "DNA Ligation Kit Mighty Mix" manufactured by Takara Bio Inc., and this was used to transform the E. coli DH5α strain.

As a result of trial of random mutations using pTrc-FPOX-18' as a template DNA, the pTrc-FPOX-18A plasmid, which expresses FPOX-18A having the amino acid sequence represented by SEQ ID NO: 6, was obtained, wherein cysteine substitutes for tyrosine at position 71 in the amino acid sequence of FPOX-18 which has the amino acid sequence represented by SEQ ID NO: 5. Furthermore, a group of mutants was constructed by using pTrc-FPOX-18' as a template DNA and introducing site-specific saturation mutations using a primer pair which has DNAs comprising the nucleotide sequences represented by SEQ ID NOs: 105 and 106. As a result of evaluating the mutants using oxidase activity on α-FV and α-F6P as an index, pTrc-FPOX-18B plasmid, which expresses FPOX-18B having the amino acid sequence represented by SEQ ID NO: 7, was obtained, wherein serine substitutes for tyrosine at position 71 in the amino acid sequence of FPOX-18 which has the amino acid sequence represented by SEQ ID NO: 5.

A group of mutants was constructed by targeting the aspartic acid at position 115 of the amino acid sequence of FPOX-18 having the amino acid sequence represented by SEQ ID NO: 5, whose glycated hexapeptide oxidase activity was found to be increased by random mutations, by using pTrc-FPOX-18B as a template DNA, and by introducing site-specific saturation mutations using a primer pair which has DNAs comprising the nucleotide sequences represented by SEQ ID NOs: 107 and 108. As a result of evaluating the mutants using oxidase activity on α-FV and α-F6P as an index, the pTrc-FPOX-18C plasmid and the pTrc-FPOX-18D plasmid were obtained. pTrc-FPOX-18C plasmid expresses FPOX-18C having the amino acid sequence represented by SEQ ID NO: 8, wherein asparagine substitutes for aspartic acid at position 115 in the amino acid sequence of FPOX-18B which has the amino acid sequence represented by SEQ ID NO: 7. pTrc-FPOX-18D plasmid expresses FPOX-18D having the amino acid sequence represented by SEQ ID NO: 9, wherein arginine substitutes for aspartic acid at position 115 in the amino acid sequence of FPOX-18B which has the amino acid sequence represented by SEQ ID NO: 7.

Furthermore, a group of mutants was constructed by targeting methionine at position 108 of the amino acid sequence of FPOX-18 having the amino acid sequence represented by SEQ ID NO: 5, whose glycated hexapeptide oxidase activity was found to be increased by random mutations, by using pTrc-FPOX-18D as a template DNA, and by introducing site-specific saturation mutations using a primer pair which has DNAs comprising the nucleotide sequences represented by SEQ ID NOs: 109 and 110. As a result of evaluating the mutants using oxidase activity on α-FV and α-F6P as an index, pTrc-FPOX-19 plasmid, which expresses FPOX-19 having the amino acid sequence represented by SEQ ID NO: 10, was obtained, wherein lysine substitutes for methionine at position 108 in the amino acid sequence of FPOX-18D which has the amino acid sequence represented by the amino acid sequence SEQ ID NO: 9.

The pTrc-FPOX-20 plasmid that expresses FPOX-20 having the amino acid sequence represented by SEQ ID NO: 11 was obtained by introduction of site-specific amino acid substitutions using pTrc-FPOX-19 as a template DNA, and by using a primer pair that has DNAs comprising the nucleotide sequences represented by SEQ ID NOs: 111 and 112, to substitute alanine for leucine at position 75 in the amino acid sequence of FPOX-19 having the amino acid sequence represented by SEQ ID NO: 10.

The six types of recombinant protein expression plasmids obtained as described above were transfected into *E. coli* DH5α strain to produce recombinant protein-expressing *E. coli* strains.

Using each of the recombinant protein-expressing *E. coli* strain, purified proteins were prepared according to the method of expression and purification of glycated peptide oxidase FPOX-15 described in International Publication No. WO 2010/041715 pamphlet, and the glycated hexapeptide oxidase activity on α-F6P was evaluated for each protein.

As shown in Table 5, the glycated hexapeptide oxidase activity of each of the proteins, FPOX-18A, FPOX-18B, FPOX-18C, FPOX-18D, FPOX-19, and FPOX-20, was increased 6.0 to 38.0 times as the glycated hexapeptide oxidase activity of FPOX-18, and were increased 190 to 7240 times as the glycated hexapeptide oxidase activity of FPOX-15.

Example 3

Enhancement of Glycated Hexapeptide Oxidase Activity by Introduction of Amino Acid Mutations The pTrc-FPOX-21 plasmid that expresses FPOX-21 having the amino acid sequence represented by SEQ ID NO: 12 was obtained by introducing site-specific amino acid substitutions using pTrc-FPOX-19 prepared in Example 2 as a template DNA, and by using a primer pair that has DNAs comprising the nucleotide sequences represented by SEQ ID NOs: 113 and 114, to substitute phenylalanine for leucine at position 75 in the amino acid sequence of FPOX-19 having the amino acid sequence represented by SEQ ID NO: 10.

Introduction of random mutations by Error Prone PCR was examined using glycated hexapeptide oxidase activity as an index and using pTrc-FPOX-21 as a template DNA.

Random mutations by Error Prone PCR was carried out using a primer pair that has DNAs comprising the nucleotide sequences represented by SEQ ID NOs: 87 and 104 designed to amplify the region corresponding to amino acid positions 1 to 119 in the protein-encoding gene included in pTrc-FPOX-21. DNAs to which mutations were introduced randomly were obtained from the random mutations as amplification products. The amplification products comprising DNAs to which mutations were introduced randomly were treated with restriction enzymes Nco I and Xho I to obtain fragments, and plasmids containing DNAs with introduced mutations were obtained by a method similar to that of Example 2, other than the operation of substituting the obtained fragments for the corresponding region of pTrc-FPOX-18' treated with the aforementioned restriction enzymes. The obtained plasmids were examined by evaluating the group of mutants expressed from the plasmids using oxidase activity on α-FV and α-F6P as an index. As a result, the following plasmids were obtained as plasmids that express proteins with improved oxidase activity towards α-F6P in comparison to that of FPOX-21:

pTrc-FPOX-22 plasmid that expresses FPOX-22 having the amino acid sequence represented by SEQ ID NO: 13, wherein threonine substitutes for serine at position 34 in the amino acid sequence of FPOX-21 which has the amino acid sequence represented by SEQ ID NO: 12;

pTrc-FPOX-23 plasmid that expresses FPOX-23 having the amino acid sequence represented by SEQ ID NO: 14, wherein histidine substitutes for tyrosine at position 52 in the amino acid sequence of FPOX-21;

pTrc-FPOX-24 plasmid that expresses FPOX-24 having the amino acid sequence represented by SEQ ID NO: 15, wherein valine substitutes for isoleucine at position 57 in the amino acid sequence of FPOX-21;

TABLE 5

| Template | Additional mutation(s) | | | Activity ratio with respect to FPOX-18* | Activity ratio with respect to FPOX-15** | |
|---|---|---|---|---|---|---|
| FPOX-18 | — | | | 1.0 | 190 | |
| | Y71C | | | 6.0 | 1140 | FPOX-18A |
| | Y71S | | | 8.1 | 1540 | FPOX-18B |
| | Y71S | D115N | | 15.3 | 2920 | FPOX-18C |
| | Y71S | D115R | | 19.0 | 3610 | FPOX-18D |
| | Y71S | D115R | M108K | 28.6 | 5440 | FPOX-19 |
| | Y71S | D115R | M108K L75A | 38.0 | 7240 | FPOX-20 |

*Activity ratio when the glycated hexapeptide oxidase activity of FPOX-18 is defined as 1
**Activity ratio when the glycated hexapeptide oxidase activity of FPOX-15 is defined as 1 pTrc-FPOX-25 plasmid that expresses FPOX-25 having the amino acid sequence represented by SEQ ID NO: 16, wherein histidine substitutes for proline at position 66 in the amino acid sequence of FPOX-21;

pTrc-FPOX-26 plasmid that expresses FPOX-26 having the amino acid sequence represented by SEQ ID NO: 17, wherein glutamic acid substitutes for aspartic acid at position 95 in the amino acid sequence of FPOX-21;

pTrc-FPOX-27 plasmid that expresses FPOX-27 having the amino acid sequence represented by SEQ ID NO: 18, wherein arginine substitutes for lysine at position 105 in the amino acid sequence of FPOX-21;

pTrc-FPOX-28 plasmid that expresses FPOX-28 having the amino acid sequence represented by SEQ ID NO: 19, wherein arginine substitutes for lysine at position 108 in the amino acid sequence of FPOX-21;

pTrc-FPOX-29 plasmid that expresses FPOX-29 having the amino acid sequence represented by SEQ ID NO: 20, wherein serine substitutes for alanine at position 355 in the amino acid sequence of FPOX-21;

pTrc-FPOX-30 plasmid that expresses FPOX-30 having the amino acid sequence represented by SEQ ID NO: 21, wherein histidine substitutes for proline at position 66 and glutamic acid substitutes for aspartic acid at position 95 in the amino acid sequence of FPOX-21;

pTrc-FPOX-31 plasmid that expresses FPOX-31 having the amino acid sequence represented by SEQ ID NO: 22, wherein histidine substitutes for proline at position 66, glutamic acid substitutes for aspartic acid at position 95, and arginine substitutes for lysine at position 105 in the amino acid sequence of FPOX-21;

pTrc-FPOX-32 plasmid that expresses FPOX-32 having the amino acid sequence represented by SEQ ID NO: 23, wherein histidine substitutes for proline at position 66, glutamic acid substitutes for aspartic acid at position 95, arginine substitutes for lysine at position 105, and arginine substitutes for lysine at position 108 in the amino acid sequence of FPOX-21;

pTrc-FPOX-33 plasmid that expresses FPOX-33 having the amino acid sequence represented by SEQ ID NO: 24, wherein threonine substitutes for serine at position 34, histidine substitutes for proline at position 66, glutamic acid substitutes for aspartic acid at position 95, arginine substitutes for lysine at position 105, and arginine substitutes for lysine at position 108 in the amino acid sequence of FPOX-21;

pTrc-FPOX-34 plasmid that expresses FPOX-34 having the amino acid sequence represented by SEQ ID NO: 25, wherein histidine substitutes for tyrosine at position 52, histidine substitutes for proline at position 66, glutamic acid substitutes for aspartic acid at position 95, arginine substitutes for lysine at position 105, and arginine substitutes for lysine at position 108 in the amino acid sequence of FPOX-21;

pTrc-FPOX-35 plasmid that expresses FPOX-35 having the amino acid sequence represented by SEQ ID NO: 26, wherein valine substitutes for isoleucine at position 57, histidine substitutes for proline at position 66, glutamic acid substitutes for aspartic acid at position 95, arginine substitutes for lysine at position 105, and arginine substitutes for lysine at position 108 in the amino acid sequence of FPOX-21;

pTrc-FPOX-36 plasmid that expresses FPOX-36 having the amino acid sequence represented by SEQ ID NO: 27, wherein histidine substitutes for proline at position 66, and arginine substitutes for lysine at position 108 in the amino acid sequence of FPOX-21;

pTrc-FPOX-37 plasmid that expresses FPOX-37 having the amino acid sequence represented by SEQ ID NO: 28, wherein histidine substitutes for proline at position 66, arginine substitutes for lysine at position 105, and arginine substitutes for lysine at position 108 in the amino acid sequence of FPOX-21;

pTrc-FPOX-38 plasmid that expresses FPOX-38 having the amino acid sequence represented by SEQ ID NO: 29, wherein histidine substitutes for proline at position 66, and serine substitutes for alanine at position 355 in the amino acid sequence of FPOX-21;

pTrc-FPOX-39 plasmid that expresses FPOX-39 having the amino acid sequence represented by SEQ ID NO: 30, wherein histidine substitutes for proline at position 66, glutamic acid substitutes for aspartic acid at position 95, and serine substitutes for alanine at position 355 in the amino acid sequence of FPOX-21;

pTrc-FPOX-40 plasmid that expresses FPOX-40 having the amino acid sequence represented by SEQ ID NO: 31, wherein histidine substitutes for proline at position 66, arginine substitutes for lysine at position 105, and serine substitutes for alanine at position 355 in the amino acid sequence of FPOX-21;

pTrc-FPOX-41 plasmid that expresses FPOX-41 having the amino acid sequence represented by SEQ ID NO: 32, wherein histidine substitutes for proline at position 66, arginine substitutes for lysine at position 108, and serine substitutes for alanine at position 355 in the amino acid sequence of FPOX-21;

pTrc-FPOX-42 plasmid that expresses FPOX-42 having the amino acid sequence represented by SEQ ID NO: 33, wherein histidine substitutes for proline at position 66, arginine substitutes for lysine at position 105, arginine substitutes for lysine at position 108, and serine substitutes for alanine at position 355 in the amino acid sequence of FPOX-21;

pTrc-FPOX-43 plasmid that expresses FPOX-43 having the amino acid sequence represented by SEQ ID NO: 34, wherein threonine substitutes for serine at position 34, histidine substitutes for proline at position 66, arginine substitutes for lysine at position 105, arginine substitutes for lysine at position 108, and serine substitutes for alanine at position 355 in the amino acid sequence of FPOX-21;

pTrc-FPOX-44 plasmid that expresses FPOX-44 having the amino acid sequence represented by SEQ ID NO: 35, wherein histidine substitutes for tyrosine at position 52, histidine substitutes for proline at position 66, arginine substitutes for lysine at position 105, arginine substitutes for lysine at position 108, and serine substitutes for alanine at position 355 in the amino acid sequence of FPOX-21;

pTrc-FPOX-45 plasmid that expresses FPOX-45 having the amino acid sequence represented by SEQ ID NO: 36, wherein valine substitutes for isoleucine at position 57, histidine substitutes for proline at position 66, arginine substitutes for lysine at position 105, arginine substitutes for lysine at position 108, and serine substitutes for alanine at position 355 in the amino acid sequence of FPOX-21; and pTrc-FPOX-46 plasmid that expresses FPOX-46 having the amino acid sequence represented by SEQ ID NO: 37, wherein histidine substitutes for proline at position 66, glutamic acid substitutes for aspartic acid at position 95, arginine substitutes for lysine at position 105, arginine substitutes for lysine at position 108, and serine substitutes for alanine at position 355 in the amino acid sequence of FPOX-21.

The 26 types of plasmids obtained as described above were introduced into the *E. coli* DH5α strain to produce mutant-expressing *E. coli* strains. According to the method of the expression and purification of the glycated peptide oxidase FPOX-15 described in International Publication No. WO 2010/041715, pamphlet, the produced *E. coli* strains described above were used to obtain each of the mutants in pure form, and each of the obtained purified mutants was evaluated for their glycated hexapeptide oxidase activity on α-F6P. As shown in Table 6, the glycated hexapeptide oxidase activities for each of the mutants, FPOX-21 to FPOX-46, were 1.3 to 4.7 times as the glycated hexapeptide oxidase activity of FPOX-19 and 7,000 to 25,500 times as the glycated hexapeptide oxidase activity of FPOX-15, and their glycated hexapeptide oxidase activities were found to be markedly improved.

cloning site (MCS) of pUC57 to construct the pUC-AoF-POX vector which contains the DNA.

(Preparation of AoFPOX-Expressing *E. coli* Strain)

DNA fragment which codes "AoFPOX tagged with four histidine residues at the N-terminal" was obtained by using pUC-AoFPOX as a template DNA, a primer to which a four histidine residues tag and an Nco I restriction enzyme site have been added to the sequence corresponding to the 5' end of the AoFPOX cDNA sequence which has a DNA comprising the nucleotide sequence represented by SEQ ID NO: 132, and a primer to which a Bam HI restriction enzyme site has been added to the sequence corresponding to the 3' end which has a DNA comprising the nucleotide sequence represented by SEQ ID NO: 133, to perform PCR under the

TABLE 6

| Template | Additional mutation(s) | | | | | Activity ratio with respect to FPOX-19* | Activity ratio with respect to FROX-15** | |
|---|---|---|---|---|---|---|---|---|
| FPOX-19 | — | | | | | 1.0 | 5440 | |
| | L75F | | | | | 1.3 | 7000 | FPOX-21 |
| | L75F | S34T | | | | 1.6 | 8490 | FPOX-22 |
| | L75F | Y52H | | | | 1.6 | 8490 | FPOX-23 |
| | L75F | I57V | | | | 1.7 | 9190 | FPOX-24 |
| | L75F | P66H | | | | 2.3 | 12700 | FPOX-25 |
| | L75F | D95E | | | | 1.8 | 9900 | FPOX-26 |
| | L75F | K105R | | | | 2.0 | 10600 | FPOX-27 |
| | L75F | K108R | | | | 1.8 | 9900 | FPOX-28 |
| | L75F | A355S | | | | 3.3 | 17700 | FPOX-29 |
| | L75F | P66H | D95E | | | 2.3 | 12700 | FPOX-30 |
| | L75F | P66H | D95E | K105R | | 2.6 | 14100 | FPOX-31 |
| | L75F | P66H | D95E | K105R | K108R | 3.3 | 17700 | FPOX-32 |
| | L75F | P66H | D95E | K105R | K108R | S34T | 3.1 | 17000 | FPOX-33 |
| | L75F | P66H | D95E | K105R | K108R | Y52H | 2.9 | 15600 | FPOX-34 |
| | L75F | P66H | D95E | K105R | K108R | I57V | 2.2 | 12000 | FPOX-35 |
| | L75F | P66H | K108R | | | 3.5 | 19100 | FPOX-36 |
| | L75F | P66H | K105R | K108R | | 2.0 | 10600 | FPOX-37 |
| | L75F | P66H | A355S | | | 4.2 | 22600 | FPOX-38 |
| | L75F | P66H | A355S | D95E | | 3.6 | 19800 | FPOX-39 |
| | L75F | P66H | A355S | K105R | | 4.0 | 21900 | FPOX-40 |
| | L75F | P66H | A355S | K108R | | 4.6 | 24800 | FPOX-41 |
| | L75F | P66H | A355S | K105R | K108R | 4.7 | 25500 | FPOX-42 |
| | L75F | P66H | A355S | K105R | K108R | S34T | 4.6 | 24800 | FPOX-43 |
| | L75F | P66H | A355S | K105R | K108R | Y52H | 4.7 | 25500 | FPOX-44 |
| | L75F | P66H | A355S | K105R | K108R | I57V | 4.6 | 24800 | FPOX-45 |
| | L75F | P66H | A355S | K105R | K108R | D95E | 2.3 | 12700 | FPOX-46 |

*Activity ratio when the glycated hexapeptide oxidase activity of FPOX-19 is defined as 1
**Activity ratio when the glycated hexapeptide oxidase activity of FPOX-15 is defined as 1

Example 4

Comparison of Glycated Hexapeptide Oxidase Activities Between the Proteins of the Present Invention and FPOX Derived from the Filamentous Fungus *Aspergillus oryzae* (AoFPOX)

The glycated hexapeptide oxidase activity of FPDX derived from *Aspergillus oryzae* RIB40 (registered with the accession number A00090023000307 in DOGAN-Database of genomes analyzed at NITE, www.bio.nite.go.jp/dogan/project/view/AO; hereinafter referred to as AoFPDX), which has the amino acid sequence represented by SEQ ID NO: 38 and is described to have oxidase activity towards α-F6P in International Publication No. WO2008/108385, pamphlet, was compared to the glycated hexapeptide oxidase activities of each of the proteins of the present invention, FPDX-19, FPDX-20, FPDX-32, and FPDX-42.

An AoFPOX-encoding DNA comprising the nucleotide sequence represented by SEQ ID NO: 76 was synthesized, and the synthesized DNA was introduced into the multifollowing PCR conditions using DNA polymerase "KOD-Plus-", a PCR kit manufactured by TOYOBO. The obtained DNA fragment was treated with restriction enzymes Nco I and Bam HI to obtain a digestion product. The aforementioned digestion product was ligated to the expression vector pTrc99a treated with restriction enzymes Nco I and Bam HI, similarly, using "DNA Ligation Kit Mighty Mix" manufactured by Takara Bio Inc. to transform the *E. coli* DH5α strain. Plasmids were extracted from colonies that grew on LB agar medium containing 50 mg/L ampicillin, and the clone found to contain the AoFPOX gene from sequence analysis was determined as a recombinant AoFPOX-expressing *E. coli* strain.

(Reagent Composition (Final Concentration))

| | |
|---|---|
| reaction buffer | |
| template DNA | 1 to 2 ng/μL |
| forward primer | 0.3 μmol/L |
| reverse primer | 0.3 μmol/L |
| dNTP solution mixture | 0.2 mmol/L each |

| | |
|---|---|
| MgSO₄ | 1 mmol/L |
| DNA polymerase | 0.02 U/L |

(PCR Conditions)
1. 94° C. for 2 minutes
2. 98° C. for 15 seconds
3. 60° C. for 30 seconds
4. 68° C. for 2 minutes
5. repeat 2 to 4 (for a total of 30 cycles)
6. 68° C. for 5 minutes (Preparation of Purified Enzyme AoFPOX)

The recombinant AoFPOX protein-expressing *E. coli* strain obtained as described above was inoculated into 200 mL of LB medium containing 50 mg/L ampicillin, and this was shake-cultured at 37° C. After the turbidity at O.D. 600 reached 0.5, 200 μL of a 0.1 mol/L aqueous solution of isopropyl-β-thiogalactoside (IPTG) was added, and this was additionally shake-cultured at 37° C. for 5 hours. After culturing, the bacterial cells were collected by centrifugation at 8,000 rpm for ten minutes.

The bacterial cells were suspended in 10 mL of 50 mmol/L phosphate buffer solution (pH7.4) containing 10 mmol/L imidazole and 0.4 mol/L potassium chloride, and then subjected to sonication. The supernatant obtained after centrifugation at 8,000 rpm for ten minutes was filtered through a 0.8 μm filter, and the obtained sample was used as a crude enzyme solution.

Purification Using a Nickel Chelating Column

A column was filled with 5 mL of "Ni-NTA Agarose" manufactured by QIAGEN, and was equilibrated using the above-mentioned buffer. The crude enzyme solution was passed through the column for adsorption of AoFPOX to the resin, and the column was washed with 3 times the volume of the same buffer and then eluted using a 50 mmol/L phosphate buffer solution (pH7.4) containing 0.5 mol/L imidazole and 0.4 mol/L potassium chloride. The AoFPOX fraction was collected by fractionation, and this was dialyzed against 10 mmol/L phosphate buffer solution (pH7.0).

The concentrations of FPOX-19 and FPOX-20 obtained in Example 2, FPOX-32 and FPOX42 obtained in Example 3, and AoFPOX were determined by measuring the absorbance specifically derived from FAD harbored by FPOX by following the method described in Example 1.

Using each of the FPOX-19, FPOX-20, FPOX-32, FPOX-42, and AoFPOX proteins, the glycated hexapeptide oxidase activity of each of the proteins was measured using the following reagents and measurement procedure.

(Reagents for Activity Measurements)

Solution A: 50 mmol/L phosphate buffer solution (pH7.0)
Solution B: 24 mmol/L solution of DA-67 in DMF
Solution C: 1 kU/L solution of peroxidase in 10 mmol/L phosphate buffer solution (pH7.0)
Solution D: 1 mmol/L aqueous solution of α-F6P
Solution E: 0.1 mg/mL to 10 mg/mL solution of glycated hexapeptide oxidase (AoFPOX, FPOX-19, FPOX-20, FPOX-32, or FPOX-42) in 10 mmol/L phosphate buffer solution (pH7.0)

(Measurement Procedure)

To 10 mL of solution A, 12.6 μL of solution B and 35 μL of solution C were added, and the obtained solution was dispensed into each well of a 96-well microplate at 190 μL per sample. 20 μL of solution D and 10 μL of solution E were added and mixed, and this was allowed to react at 30° C. for 30 minutes. The absorbance of the solution before reaction $Abs_{(before\ reaction)}$ at 660 nm (main wavelength)/750 nm (sub-wavelength), and the absorbance of the solution after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$. Absorbance change for the blank $\Delta'Abs_{(blank)}$ was determined by a similar method except for using distilled water instead of solution E (protein solution). The reaction absorbance $\Delta Abs_{(reaction)}$ for the protein was obtained by subtracting the absorbance change for the blank $\Delta'Abs_{(blank)}$ from the absorbance change due to the reaction $\Delta'Abs_{(reaction)}$. The specific activity (U/mg) for glycated hexapeptide oxidase activity of each of the proteins was calculated from the obtained absorbance $\Delta Abs_{(reaction)}$ by following the method described in Example 2.

As shown in Table 7, the glycated hexapeptide oxidase activity of AoFPOX was approximately 0.5% of the glycated hexapeptide oxidase activity of FPOX-20, and the glycated hexapeptide oxidase activities of FPOX-19, FPOX-20, FPOX-32, and FPOX-42 of the present invention were markedly higher than that of glycated peptide oxidase AoFPOX described in International Publication No. WO 2008/108385, pamphlet.

TABLE 7

| Protein | Specific activity (mU/mg) | %* |
|---|---|---|
| FPOX-19 | 19.6 | 85.6 |
| FPOX-20 | 22.9 | 100.0 |
| FPOX-32 | 64.7 | 282.5 |
| FPOX-42 | 92.1 | 402.2 |
| AoFPOX | 0.12 | 0.5 |

*Specific activity of FPOX-20 is defined as 100%

Example 5

Measurement of HbA1c Using V8 Protease and the Proteins of the Present Invention HbA1c in hemolysate samples were measured by the following method using hemocytes as a sample, and using V8 protease and proteins of the present invention, FPOX-19, FPOX-32, or FPOX-42.

Using the following reagents and measurement procedure, HbA1c in a sample was treated with V8 protease, α-F6P produced was reacted with each of the proteins, FPOX-19, FPOX-32, and FPOX-42, and the absorbance changes from the reactions were measured.

(Reagents for Activity Measurements)

Solution A: 0.1 mol/L MOPS buffer solution (pH6.8)
Solution B: 24 mmol/L solution of DA-67 in DMF
Solution C: 1 kU/L solution of peroxidase in 10 mmol/L phosphate buffer solution (pH7.0)
Solution D: human hemocyte-derived hemolysate samples [The hemoglobin concentration is 10 mg/mL, and the HbA1c concentrations have been determined to be 9.8, 11.1, 12.3, 13.3, 14.5, 15.4, 17.9, and 23.3 μmol/L from both of the HPLC method (KO500 method) and the hemoglobin-SLS method.]
Solution E: 8 g/L solution of potassium iodate and 10% (v/v) AMPHITOL 20N in 100 mmol/L Tris-HCl (pH8.0)
Solution F: 80 U/mL solution of V8 protease in 20% glycerol Solution G: 10 mg/mL solution of glycated hexapeptide oxidase in 10 mmol/L phosphate buffer solution (pH7.0)

In hemoglobin concentration measurements using the hemoglobin-SLS method, Hemoglobin B-test Wako was used.

(Measurement Procedure)

(i) 4 μL of Solution E was added to 40 μL of Solution D and mixed, then 4.4 μL of Solution F was added, and this was incubated at 37° C. for 15 minutes.

(ii) To 10 mL of Solution A, 12.6 μL of Solution B and 35 μL of Solution C were added, and the obtained solution was dispensed into each well of a 96-well microplate at 190 μL per sample. Then 20 μL of the treated hemocyte solution prepared in (i) above and 10 μL of Solution G was added and mixed, and this was allowed to react at 37° C. for 15 minutes.

The absorbance of the solution before reaction $Abs_{(before\ reaction)}$ at 660 nm (main wavelength)/750 nm (sub-wavelength), and the absorbance after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$. Absorbance change for the blank $\Delta'Abs_{(blank)}$ was determined by a similar method except for using distilled water instead of solution D (human hemocyte-derived hemolysate sample). The reaction absorbance $\Delta Abs_{(reaction)}$ for the human hemocyte-derived hemolysate sample was obtained by subtracting the absorbance change for the blank $\Delta'Abs_{(blank)}$ from the absorbance change due to the reaction $\Delta'Abs_{(reaction)}$. Similar reactions were performed on each of the human hemocyte-derived hemolysate samples, and the reaction absorbance $\Delta Abs_{(reaction)}$ for each of the human hemocyte-derived hemolysate samples were determined.

Figure 2:
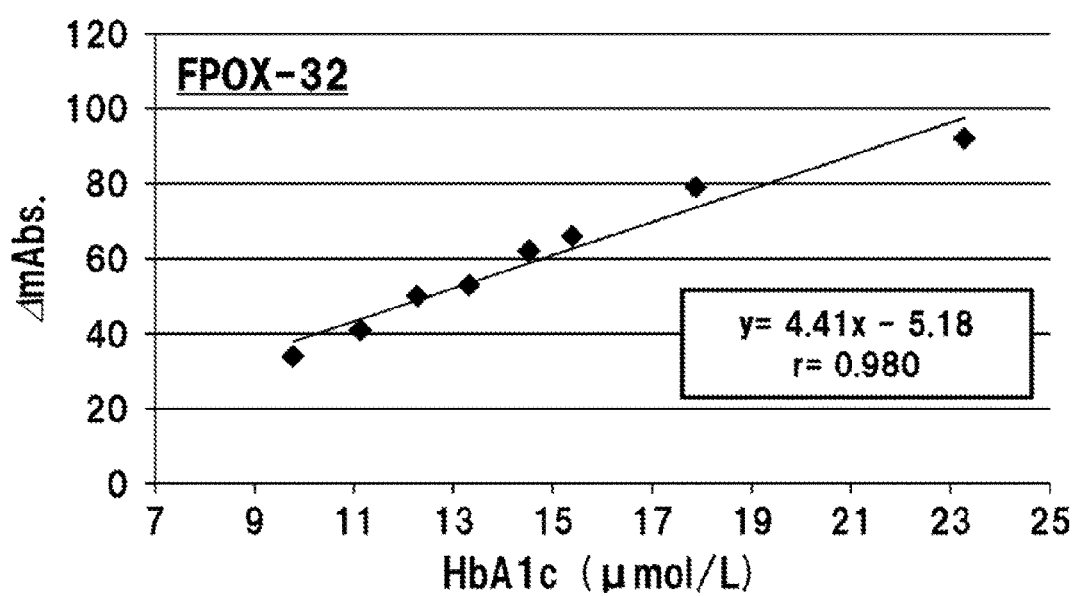
FIG. 2 shows a graph indicating the correlation between the method for measuring glycated hemoglobin of the present invention using V8 protease and FPOX-32, and the method for measuring glycated hemoglobin using both of the HPLC method (KO500 method) and the hemoglobin-SLS method.
Figure 3:
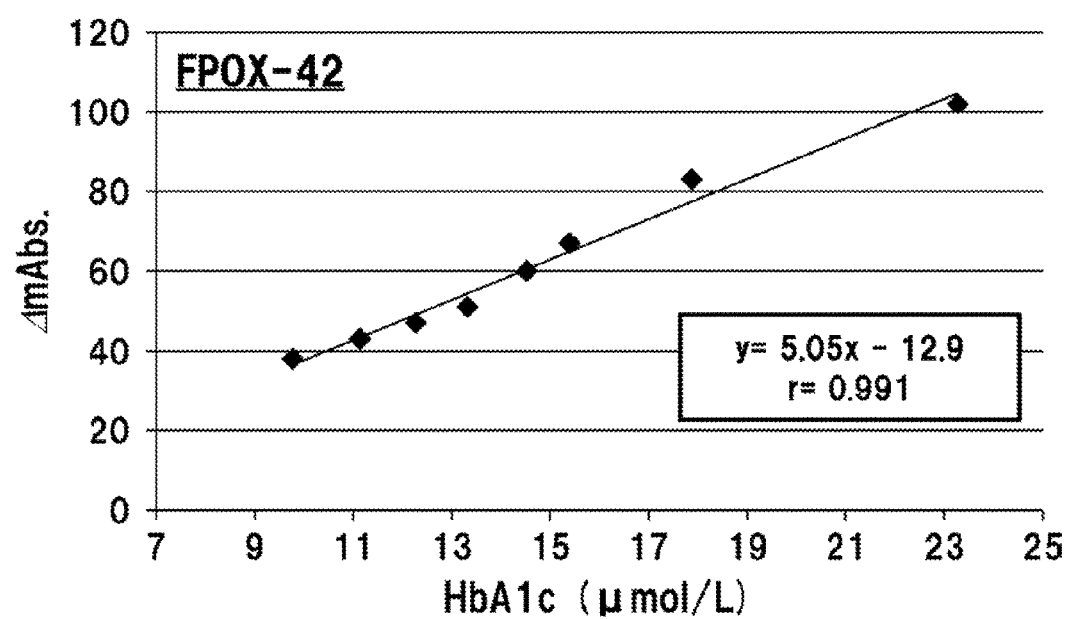
FIG. 3 shows a graph indicating the correlation between the method for measuring glycated hemoglobin of the present invention using V8 protease and FPOX-42, and the method for measuring glycated hemoglobin using both of the HPLC method (KO500 method) and the hemoglobin-SLS method.
Figure 4:
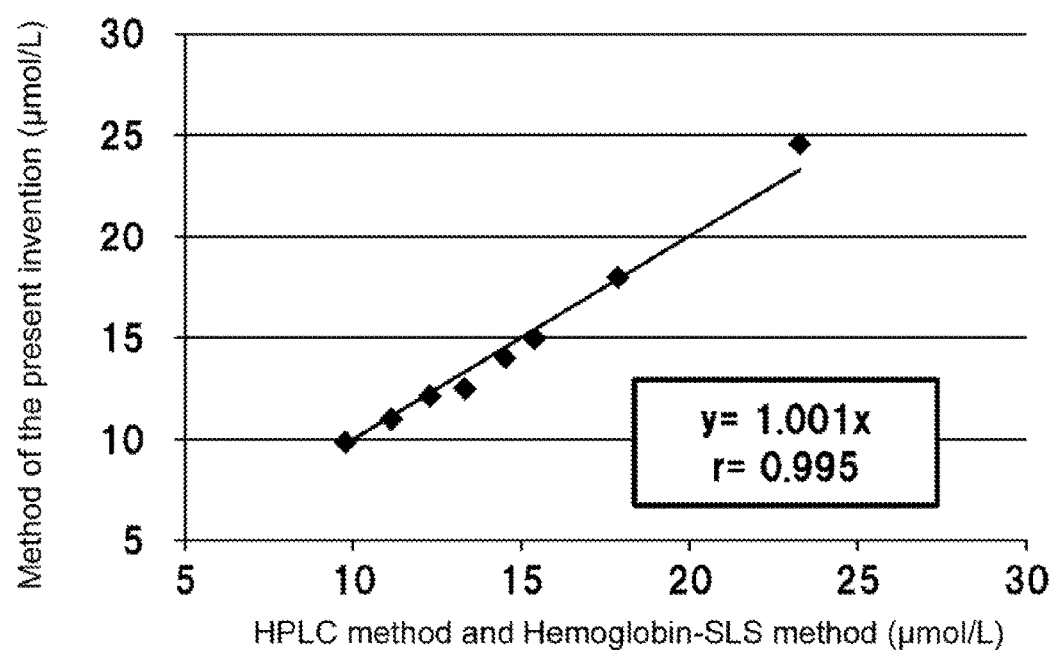
FIG. 4 shows a graph indicating the correlation between the method for measuring glycated hemoglobin of the present invention, in which FPOX-19 is used and protease is not used, and the method for measuring glycated hemoglobin using both of the HPLC method (KO500 method) and the hemoglobin-SLS method.
Figure 5:
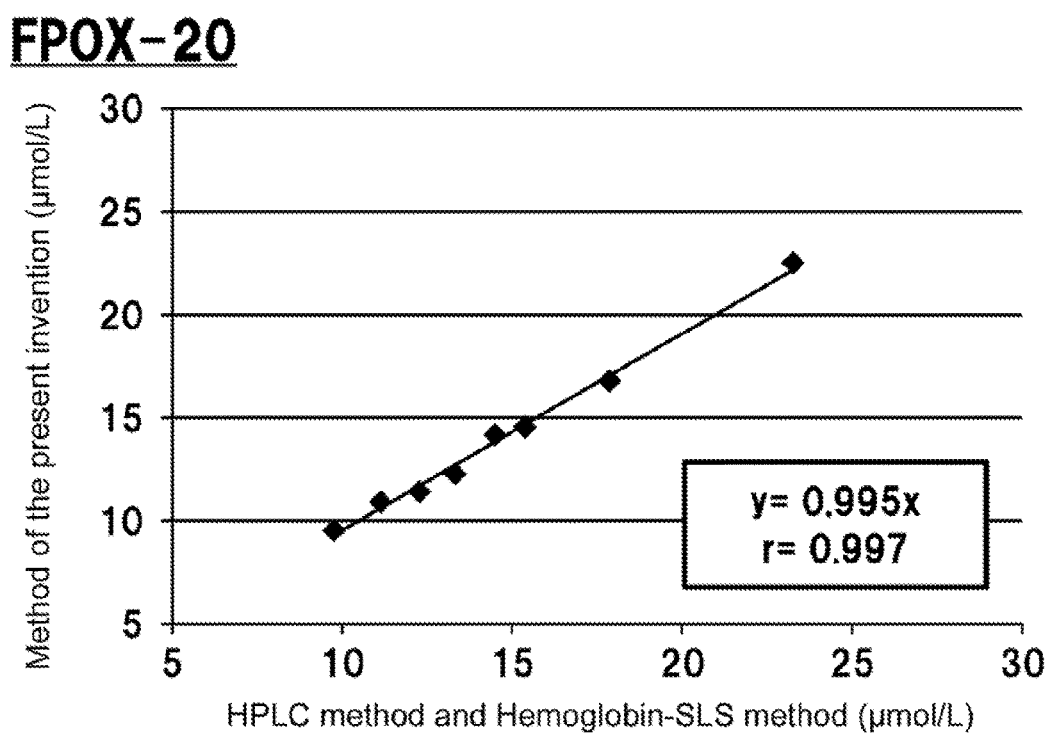
FIG. 5 shows a graph indicating the correlation between the method for measuring glycated hemoglobin of the present invention, in which FPOX-20 is used and protease is not used, and the method for measuring glycated hemoglobin using both of the HPLC method (KO500 method) and the hemoglobin-SLS method.
Figure 6:
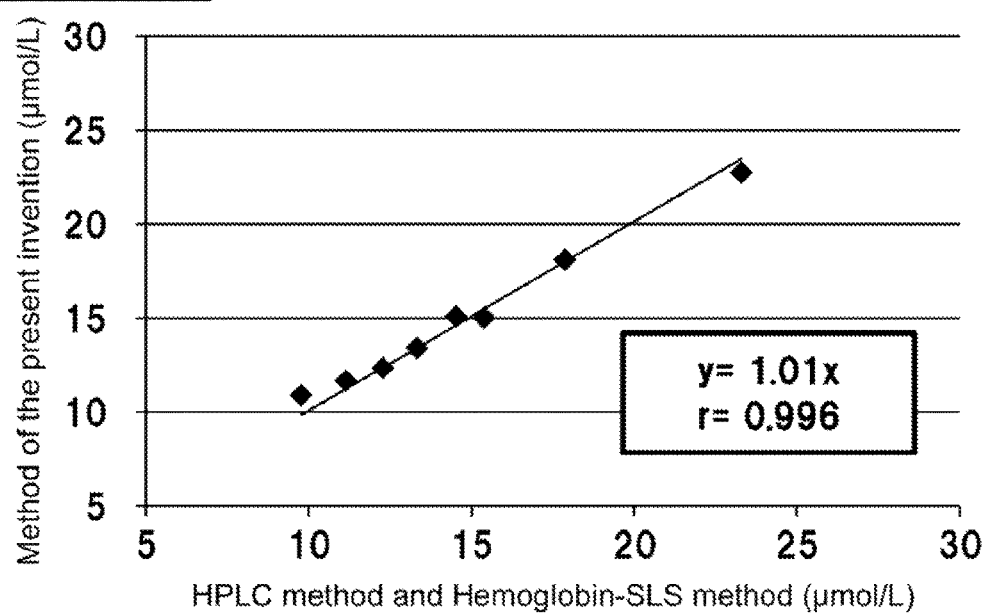
FIG. 6 shows a graph indicating the correlation between the method for measuring glycated hemoglobin of the present invention, in which FPOX-32 is used and protease is not used, and the method for measuring glycated hemoglobin using both of the HPLC method (KO500 method) and the hemoglobin-SLS method.
Figure 7:
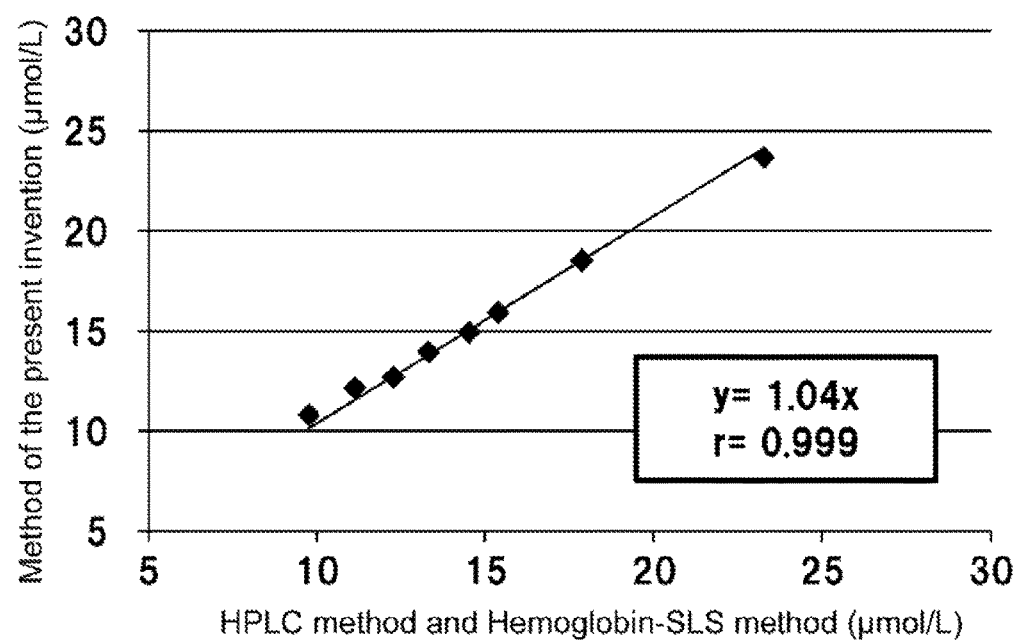
FIG. 7 shows a graph indicating the correlation between the method for measuring glycated hemoglobin of the present invention, in which FPOX-42 is used and protease is not used, and the method for measuring glycated hemoglobin using both of the HPLC method (KO500 method) and the hemoglobin-SLS method.

As a result, good linearity was found between HbA1c concentration determined by both of the HPLC method and the hemoglobin-SLS method, and the reaction absorbance $\Delta Abs_{(reaction)}$ for each of the human hemocyte-derived hemolysate samples obtained by the above-mentioned determinations, as shown in FIGS. 1 to 3.

The results showed that HbA1c in samples can be measured by using the proteins of the present invention and V8 protease which digests HbA1c to dissociate α-F6P.

Example 6

Measurement of Glycated Hemoglobin Oxidase Activities of the Proteins of the Present Invention Using FPOX-18A, FPOX-18B, FPOX-19, and FPOX-20 obtained in Example 2, FPOX-32 and FPOX-42 obtained in Example 3, and FPOX-15, glycated hemoglobin oxidase activities were measured using the following reagents and measurement procedure.

(Reagents for Activity Measurements)
Solution A: 0.1 mol/L MOPS buffer solution (pH6.8)
Solution B: 24 mmol/L solution of DA-67 in DMF
Solution C: 1 kU/L solution of peroxidase in 10 mmol/L phosphate buffer solution (pH7.0)
Solution D: human hemocyte-derived hemolysate sample [The hemoglobin concentration is 10 mg/mL, and the HbA1c concentration has been determined to be 84.2 won from both of the HPLC method (KO500 method) and the hemoglobin-SLS method.]

Solution E: 5 g/L aqueous solution of potassium iodate and 50% (v/v) AMPHITOL 20N Solution F: 30 mg/mL solution of glycated hemoglobin oxidase (FPOX-18A, FPOX-18B, FPOX-19, FPOX-20, FPOX-32, FPOX-42, and FPOX-15) in 10 mmol/L phosphate buffer solution (pH7.0)

(Measurement Procedure)

(i) 2 μL of Solution E was mixed into 20 μL of Solution D, and this was incubated at 37° C. for 10 minutes.

(ii) To 10 mL of Solution A, 12.6 μL of Solution B and 35 μL of Solution C were added, and the obtained solution was dispensed into each well of a 96-well microplate at 190 μL per sample. Then 20 μL of a solution obtained by mixing Solutions D and E, and 10 μL of Solution F were added and mixed, and this was allowed to react at 37° C. for 60 minutes.

The absorbance of the solution before reaction $Abs_{(before\ reaction)}$ at 660 nm (main wavelength)/750 nm (sub-wavelength), and the absorbance after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$. The absorbance change for a blank derived from the enzyme solution $\Delta'Abs_{(enzyme\ solution\ blank)}$ was determined by a similar method except for using a pH7.0 10 mmol/L phosphate buffer solution instead of Solution F (enzyme solution). Absorbance change for the blank derived from the human hemocyte-derived hemolysate sample $\Delta'Abs_{(hemolysate\ sample\ blank)}$ was determined by a similar method except for using distilled water instead of solution D (human hemocyte-derived hemolysate sample).

The reaction absorbance $\Delta Abs_{(reaction)}$ for the protein was determined by subtracting $\Delta'Abs_{(enzyme\ solution\ blank)}$ and $\Delta'Abs_{(hemolysate\ sample\ blank)}$ from the absorbance change due to the reaction $\Delta'Abs_{(reaction)}$. The reaction absorbance $\Delta Abs_{(reaction)}$ for each of the proteins, FPOX-15, FPOX-18A, FPOX-18B, FPOX-19, FPOX-20, FPOX-32, and FPOX-42, are shown in Table 8.

As shown in Table 8, while ΔAbs is below the detection limit for FPOX-15, ΔAbs values for FPOX-18A, FPOX-18B, FPOX-19, FPOX-20, FPOX-32, and FPOX-42 were 0.017, 0.021, 0.054, 0.080, 0.235, and 0.246, respectively. It was found that by using FPOX-18A, FPOX-18B, FPOX-19, FPOX-20, FPOX-32, and FPOX-42, reaction between the enzymes and HbA1c proceeded to produce hydrogen peroxide.

TABLE 8

| Protein | $\Delta Abs_{(reaction)}$ |
|---|---|
| FPOX-15 | n.d. * |
| FPOX-18A | 0.017 |
| FPOX-18B | 0.021 |
| FPOX-19 | 0.054 |
| FPOX-20 | 0.080 |
| FPOX-32 | 0.235 |
| FPOX-42 | 0.246 |

* Not detected

Example 7

Correlation Between the Method for Measuring Glycated Hemoglobin Using the Proteins of the Present Invention, and the Method for Measuring Glycated Hemoglobin Using Both of the HPLC Method and the Hemoglobin-SLS Method The following reagents and measurement procedure were used to confirm the correlation between the HbA1c measurement method of the present invention using each of the proteins, FPOX-19 and FPOX-20 obtained in Example 2 and FPOX-32 and FPOX-42 obtained in Example 3, and the HbA1c measurement method using both of the HPLC method (KO500 method) and the hemoglobin-SLS method.
(Reagents for Activity Measurements)
Solution A: 0.1 mol/L MOPS buffer solution (pH6.8)
Solution B: 24 mmol/L solution of DA-67 in DMF
Solution C: 1 kU/L peroxidase in 10 mmol/L phosphate buffer solution (pH7.0)
Solution D: human hemocyte-derived hemolysate sample [The hemoglobin concentration is 10 mg/mL, and the HbA1c concentrations have been determined to be 9.8, 11.1, 12.3, 13.3, 14.5, 15.4, 17.9, and 23.3 µmol/L from both of the HPLC method (KO500 method) and the hemoglobin-SLS method.]
Solution E: 5 g/L aqueous solution of potassium iodate and 50% (v/v) AMPHITOL 20N
Solution F: 30 mg/mL solution of glycated hemoglobin oxidase (FPOX-19, FPOX-20, FPOX-32, or FPOX-42) in 10 mmol/L phosphate buffer solution (pH7.0)
(Measurement Procedure)

(i) 4 µL of Solution E was mixed into 40 µL of Solution D, and this was incubated at 37° C. for 10 minutes.

(ii) To 10 mL of Solution A, 12.6 µL of Solution B and 35 µL of Solution C were added, and the obtained solution was dispensed into each well of a 96-well microplate at 190 µL per sample. Then 20 µL of the solution obtained by mixing Solutions D and E, and 10 µL of Solution F were added and mixed, and this was allowed to react at 37° C. for 60 minutes.

The absorbance of the solution before reaction $Abs_{(before\ reaction)}$ at 660 nm (main wavelength)/750 nm (sub-wavelength), and the absorbance after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$.

Similar measurements were performed using two human hemocyte-derived hemolysate samples with known HbA1c concentrations (samples in which the hemoglobin concentration is 10 mg/mL and the HbA1c concentrations are 9.82 µmol/L and 24.2 µmol/L, respectively) to prepare a calibration curve indicating the relationship between HbA1c concentration and reaction absorbance $\Delta Abs_{(reaction)}$.

HbA1c concentration in each of the human hemocyte-derived hemolysate samples was determined by comparing the reaction absorbance $\Delta Abs_{(reaction)}$ for each of the human hemocyte-derived hemolysate samples with the values of the above-mentioned calibration curve. HbA1c concentration determined this way was compared with the HbA1c concentration determined by the HbA1c measurement method using both of the HPLC method (KO500 method) and the hemoglobin-SLS method.

As shown in FIGS. 4 to 7, good correlation was observed between HbA1c concentrations determined by the measurement methods of the present invention and HbA1c concentrations determined by the HbA1c measurement method using both of the HPLC method (KO500 method) and the hemoglobin-SLS method. Accordingly, the measurement method using each of the proteins, FPOX-19, FPOX-20, FPOX-32, and FPOX-42 of the present invention was found to enable measurement of HbA1c in samples without the use of a protease.

INDUSTRIAL APPLICABILITY

The present invention provides novel proteins useful for diagnosing life-style diseases such as diabetes, DNAs encoding the proteins, methods for producing the proteins, as well as methods for measuring glycated hemoglobin using the proteins, and reagents for measuring glycated hemoglobin comprising the proteins.

Sequence Listing Free Text

SEQ ID NO: 1—Description of Artificial Sequence: Amino acid sequence of FPOX-15
SEQ ID NO: 2—Description of Artificial Sequence: Amino acid sequence of FPOX-9
SEQ ID NO: 3—Description of Artificial Sequence: Amino acid sequence of FPOX-16
SEQ ID NO: 4—Description of Artificial Sequence: Amino acid sequence of FPOX-17
SEQ ID NO: 5—Description of Artificial Sequence: Amino acid sequence of FPOX-18
SEQ ID NO: 6—Description of Artificial Sequence: Amino acid sequence of FPOX-18A
SEQ ID NO: 7—Description of Artificial Sequence: Amino acid sequence of FPOX-18B
SEQ ID NO: 8—Description of Artificial Sequence: Amino acid sequence of FPOX-18C
SEQ ID NO: 9—Description of Artificial Sequence: Amino acid sequence of FPOX-18D
SEQ ID NO: 10—Description of Artificial Sequence: Amino acid sequence of FPOX-19
SEQ ID NO: 11—Description of Artificial Sequence: Amino acid sequence of FPOX-20
SEQ ID NO: 12—Description of Artificial Sequence: Amino acid sequence of FPOX-21
SEQ ID NO: 13—Description of Artificial Sequence: Amino acid sequence of FPOX-22
SEQ ID NO: 14—Description of Artificial Sequence: Amino acid sequence of FPOX-23
SEQ ID NO: 15—Description of Artificial Sequence: Amino acid sequence of FPOX-24
SEQ ID NO: 16—Description of Artificial Sequence: Amino acid sequence of FPOX-25
SEQ ID NO: 17—Description of Artificial Sequence: Amino acid sequence of FPOX-26
SEQ ID NO: 18—Description of Artificial Sequence: Amino acid sequence of FPOX-27
SEQ ID NO: 19—Description of Artificial Sequence: Amino acid sequence of FPOX-28
SEQ ID NO: 20—Description of Artificial Sequence: Amino acid sequence of FPOX-29
SEQ ID NO: 21—Description of Artificial Sequence: Amino acid sequence of FPOX-30
SEQ ID NO: 22—Description of Artificial Sequence: Amino acid sequence of FPOX-31

SEQ ID NO: 23—Description of Artificial Sequence: Amino acid sequence of FPOX-32
SEQ ID NO: 24—Description of Artificial Sequence: Amino acid sequence of FPOX-33
SEQ ID NO: 25—Description of Artificial Sequence: Amino acid sequence of FPOX-34
SEQ ID NO: 26—Description of Artificial Sequence: Amino acid sequence of FPOX-35
SEQ ID NO: 27—Description of Artificial Sequence: Amino acid sequence of FPOX-36
SEQ ID NO: 28—Description of Artificial Sequence: Amino acid sequence of FPOX-37
SEQ ID NO: 29—Description of Artificial Sequence: Amino acid sequence of FPOX-38
SEQ ID NO: 30—Description of Artificial Sequence: Amino acid sequence of FPOX-39
SEQ ID NO: 31—Description of Artificial Sequence: Amino acid sequence of FPOX-40
SEQ ID NO: 32—Description of Artificial Sequence: Amino acid sequence of FPOX-41
SEQ ID NO: 33—Description of Artificial Sequence: Amino acid sequence of FPOX-42
SEQ ID NO: 34—Description of Artificial Sequence: Amino acid sequence of FPOX-43
SEQ ID NO: 35—Description of Artificial Sequence: Amino acid sequence of FPOX-44
SEQ ID NO: 36—Description of Artificial Sequence: Amino acid sequence of FPOX-45
SEQ ID NO: 37—Description of Artificial Sequence: Amino acid sequence of FPOX-46
SEQ ID NO: 38—Description of Artificial Sequence: Amino acid sequence of AoFPOX
SEQ ID NO: 39—Description of Artificial Sequence: DNA of FPOX-15
SEQ ID NO: 40—Description of Artificial Sequence: DNA of FPOX-9
SEQ ID NO: 41—Description of Artificial Sequence: DNA of FPOX-16
SEQ ID NO: 42—Description of Artificial Sequence: DNA of FPOX-17
SEQ ID NO: 43—Description of Artificial Sequence: DNA of FPOX-18
SEQ ID NO: 44—Description of Artificial Sequence: DNA of FPOX-18A
SEQ ID NO: 45—Description of Artificial Sequence: DNA of FPOX-18B
SEQ ID NO: 46—Description of Artificial Sequence: DNA of FPOX-18C
SEQ ID NO: 47—Description of Artificial Sequence: DNA of FPOX-18D
SEQ ID NO: 48—Description of Artificial Sequence: DNA of FPOX-19
SEQ ID NO: 49—Description of Artificial Sequence: DNA of FPOX-20
SEQ ID NO: 50—Description of Artificial Sequence: DNA of FPOX-21
SEQ ID NO: 51—Description of Artificial Sequence: DNA of FPOX-22
SEQ ID NO: 52—Description of Artificial Sequence: DNA of FPOX-23
SEQ ID NO: 53—Description of Artificial Sequence: DNA of FPOX-24
SEQ ID NO: 54—Description of Artificial Sequence: DNA of FPOX-25
SEQ ID NO: 55—Description of Artificial Sequence: DNA of FPOX-26
SEQ ID NO: 56—Description of Artificial Sequence: DNA of FPOX-27
SEQ ID NO: 57—Description of Artificial Sequence: DNA of FPOX-28
SEQ ID NO: 58—Description of Artificial Sequence: DNA of FPOX-29
SEQ ID NO: 59—Description of Artificial Sequence: DNA of FPOX-30
SEQ ID NO: 60—Description of Artificial Sequence: DNA of FPOX-31
SEQ ID NO: 61—Description of Artificial Sequence: DNA of FPOX-32
SEQ ID NO: 62—Description of Artificial Sequence: DNA of FPOX-33
SEQ ID NO: 63—Description of Artificial Sequence: DNA of FPOX-34
SEQ ID NO: 64—Description of Artificial Sequence: DNA of FPOX-35
SEQ ID NO: 65—Description of Artificial Sequence: DNA of FPOX-36
SEQ ID NO: 66—Description of Artificial Sequence: DNA of FPOX-37
SEQ ID NO: 67—Description of Artificial Sequence: DNA of FPOX-38
SEQ ID NO: 68—Description of Artificial Sequence: DNA of FPOX-39
SEQ ID NO: 69—Description of Artificial Sequence: DNA of FPOX-40
SEQ ID NO: 70—Description of Artificial Sequence: DNA of FPOX-41
SEQ ID NO: 71—Description of Artificial Sequence: DNA of FPOX-42
SEQ ID NO: 72—Description of Artificial Sequence: DNA of FPOX-43
SEQ ID NO: 73—Description of Artificial Sequence: DNA of FPOX-44
SEQ ID NO: 74—Description of Artificial Sequence: DNA of FPOX-45
SEQ ID NO: 75—Description of Artificial Sequence: DNA of FPOX-46
SEQ ID NO: 76—Description of Artificial Sequence: DNA of AoFPOX
SEQ ID NO: 77—Description of Artificial Sequence: M58F/S59G-F primer
SEQ ID NO: 78—Description of Artificial Sequence: M58F/S59G-R primer
SEQ ID NO: 79—Description of Artificial Sequence: G105K-F primer
SEQ ID NO: 80—Description of Artificial Sequence: G105K-R primer
SEQ ID NO: 81—Description of Artificial Sequence: G183E-F primer
SEQ ID NO: 82—Description of Artificial Sequence: G183E-R primer
SEQ ID NO: 83—Description of Artificial Sequence: N272D-F primer
SEQ ID NO: 84—Description of Artificial Sequence: N272D-R primer
SEQ ID NO: 85—Description of Artificial Sequence: P302L-F primer
SEQ ID NO: 86—Description of Artificial Sequence: P302L-R primer
SEQ ID NO: 87—Description of Artificial Sequence: pTrc-F1 primer
SEQ ID NO: 88—Description of Artificial Sequence: pTrc-R primer SEQ ID NO: 89—Description of Artificial Sequence: pTrc-F2 primer
SEQ ID NO: 90—Description of Artificial Sequence: R61 saturation-F primer
SEQ ID NO: 91—Description of Artificial Sequence: R61 saturation-R primer
SEQ ID NO: 92—Description of Artificial Sequence: R63 saturation-F primer
SEQ ID NO: 93—Description of Artificial Sequence: R63 saturation-R primer
SEQ ID NO: 94—Description of Artificial Sequence: R61S/R63A-F primer
SEQ ID NO: 95—Description of Artificial Sequence: R61S/R63A-R primer
SEQ ID NO: 96—Description of Artificial Sequence: L62 saturation-F primer
SEQ ID NO: 97—Description of Artificial Sequence: L62 saturation-R primer
SEQ ID NO: 98—Description of Artificial Sequence: Q93E-F primer
SEQ ID NO: 99—Description of Artificial Sequence: Q93E-R primer
SEQ ID NO: 100—Description of Artificial Sequence: F267Y-F primer
SEQ ID NO: 101—Description of Artificial Sequence: F267Y-R primer
SEQ ID NO: 102—Description of Artificial Sequence: BglII introduction-F primer
SEQ ID NO: 103—Description of Artificial Sequence: BglII introduction-R primer
SEQ ID NO: 104—Description of Artificial Sequence: EP-R primer
SEQ ID NO: 105—Description of Artificial Sequence: Y71 saturation-F primer
SEQ ID NO: 106—Description of Artificial Sequence: Y71 saturation-R primer
SEQ ID NO: 107—Description of Artificial Sequence: D115 saturation-F primer
SEQ ID NO: 108—Description of Artificial Sequence: D115 saturation-R primer
SEQ ID NO: 109—Description of Artificial Sequence: M108 saturation-F primer
SEQ ID NO: 110—Description of Artificial Sequence: M108 saturation-R primer
SEQ ID NO: 111—Description of Artificial Sequence: L75A-F primer
SEQ ID NO: 112—Description of Artificial Sequence: L75A-R primer
SEQ ID NO: 113—Description of Artificial Sequence: L75F-F primer
SEQ ID NO: 114—Description of Artificial Sequence: L75F-R primer
SEQ ID NO: 115—Description of Artificial Sequence: S34T-F primer
SEQ ID NO: 116—Description of Artificial Sequence: S34T-R primer
SEQ ID NO: 117—Description of Artificial Sequence: Y52H-F primer
SEQ ID NO: 118—Description of Artificial Sequence: Y52H-R primer
SEQ ID NO: 119—Description of Artificial Sequence: I57V-F primer
SEQ ID NO: 120—Description of Artificial Sequence: I57V-R primer
SEQ ID NO: 121—Description of Artificial Sequence: P66H-F primer
SEQ ID NO: 122—Description of Artificial Sequence: P66H-R primer
SEQ ID NO: 123—Description of Artificial Sequence: D95E-F primer
SEQ ID NO: 124—Description of Artificial Sequence: D95E-R primer
SEQ ID NO: 125—Description of Artificial Sequence: K105R-F primer
SEQ ID NO: 126—Description of Artificial Sequence: K105R-R1 primer
SEQ ID NO: 127—Description of Artificial Sequence: K105R-R2 primer
SEQ ID NO: 128—Description of Artificial Sequence: K108R-F primer
SEQ ID NO: 129—Description of Artificial Sequence: K108R-R primer
SEQ ID NO: 130—Description of Artificial Sequence: A355S-F primer
SEQ ID NO: 131—Description of Artificial Sequence: A355S-R primer
SEQ ID NO: 132—Description of Artificial Sequence: AoF-POX-F primer
SEQ ID NO: 133—Description of Artificial Sequence: AoF-POX-R primer

The invention claimed is:

1. An isolated protein comprising the amino acid sequence set forth in SEQ ID NO: 1 with a substitution of arginine at position 61 with an amino acid selected from the group consisting of glycine, alanine, valine, leucine, serine, threonine, proline, cysteine, methionine, asparagine, glutamine, and aspartic acid, wherein the isolated protein has glycated hexapeptide oxidase activity.

2. An isolated protein, wherein the protein comprises an amino acid sequence that is at least 95% identical to SEQ ID NO:1, wherein the protein has glycated hexapeptide oxidase activity, and wherein the amino acid at position 61 is substituted with an amino acid selected from the group consisting of glycine, alanine, valine, leucine, serine, threonine, proline, cysteine, methionine, asparagine, glutamine, and aspartic acid.

3. The isolated protein of claim 1, further having at least one mutation selected from the following (1) to (15) in the amino acid sequence set forth in SEQ ID NO: 1:

(1) mutation where arginine at position 63 is substituted with an amino acid selected from the group consisting of glycine, proline, and alanine;

(2) mutation where leucine at position 62 is substituted with glycine;

(3) mutation where glutamine at position 93 is substituted with glutamic acid;

(4) mutation where phenylalanine at position 267 is substituted with tyrosine;

(5) mutation where tyrosine at position 71 is substituted with serine or cysteine;

(6) mutation where aspartic acid at position 115 is substituted with an amino acid selected from the group consisting of asparagine and arginine;

(7) mutation where methionine at position 108 is substituted with an amino acid selected from the group consisting of lysine and arginine;

(8) mutation where leucine at position 75 is substituted with an amino acid selected from the group consisting of alanine and phenylalanine;

(9) mutation where serine at position 34 is substituted with threonine;

(10) mutation where tyrosine at position 52 is substituted with histidine;

(11) mutation where isoleucine at position 57 is substituted with valine;

(12) mutation where proline at position 66 is substituted with histidine;

(13) mutation where aspartic acid at position 95 is substituted with glutamic acid;

(14) mutation where lysine at position 105 is substituted with arginine; and

(15) mutation where alanine at position 355 is substituted with serine.

4. The isolated protein of claim 2, further comprising an additional substitution, wherein the protein comprises an amino acid sequence that is at least 95% identical to any one of SEQ ID NOs: 3 to 37.

5. The isolated protein of claim 4, wherein said protein comprises the amino acid sequence set forth in any one of SEQ ID NOs: 3 to 37.

6. The isolated protein of claim 2, further comprising an additional substitution, wherein the protein comprises an amino acid sequence that is at least 95% identical to any one of SEQ ID NOs: 6 to 37, and wherein the protein has an activity of directly oxidizing glycated hemoglobin.

7. The isolated protein of claim 6, wherein said protein comprises the amino acid sequence set forth in any one of SEQ ID NOs: 6 to 37.

8. The isolated protein of claim 6, wherein the glycated hemoglobin is hemoglobin A1c.

* * * * *

SEQUENCE LISTING

```
<160> NUMBER OF SEQ ID NOS: 135

<210> SEQ ID NO 1
<211> LENGTH: 438
<212> TYPE: PRT
<213> ORGANISM: Artificial
<220> FEATURE:
<223> OTHER INFORMATION: FPOX-15

<400> SEQUENCE: 1

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45
```

Ser Ala Gly Tyr Asp Leu Asn Lys Ile Phe Gly Ile Arg Leu Arg Asn
    50              55                  60
Lys Pro Asp Leu Gln Leu Tyr Leu Glu Ala Leu Asp Met Trp Lys Asn
 65              70                  75                  80
Asp Pro Leu Phe Lys Pro Phe Phe His Asn Val Gly Gln Met Asp Val
                 85                  90                  95
Ser Ser Thr Glu Glu Gly Ile Lys Lys Leu Arg Met Arg Tyr Gln Ser
            100                 105                 110
Leu Leu Asp Ala Gly Ile Gly Leu Glu Lys Thr Asn Phe Leu Leu Glu
            115                 120                 125
Ser Glu Asp Glu Ile Leu Ala Lys Ala Pro His Phe Thr Arg Glu Gln
130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
            180                 185                 190
Ala Asp Ala Asp Glu Lys Thr Cys Ile Gly Val Glu Thr Val Asp Gly
            195                 200                 205
Thr Lys Tyr Tyr Ala Asp Lys Val Val Leu Ala Ala Gly Ala Trp Ser
210                 215                 220
Ser Thr Leu Val Asp Leu Glu Glu Gln Cys Val Ser Lys Ala Trp Val
225                 230                 235                 240
Phe Ala His Ile Gln Leu Thr Pro Ala Glu Ala Ala Tyr Lys Asn
                245                 250                 255
Thr Pro Val Ile Tyr Asp Gly Asp Tyr Gly Phe Phe Ile Glu Pro Asp
            260                 265                 270
Glu Asn Gly Ile Ile Lys Val Cys Asp Glu Phe Pro Gly Phe Thr His
            275                 280                 285
Phe Lys Met His Gln Pro Tyr Gly Ser Pro Val Pro Lys Leu Ile Ser
290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
            340                 345                 350
Ala Asp Ala Asn Leu Leu Val Cys Glu His Pro Arg Trp Lys Gly Phe
            355                 360                 365
Tyr Leu Ala Thr Gly Asp Ser Gly His Ser Phe Lys Leu Leu Pro Asn
370                 375                 380
Ile Gly Lys His Val Val Glu Leu Leu Glu Gly Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
            435

<210> SEQ ID NO 2
<211> LENGTH: 438
<212> TYPE: PRT

<213> ORGANISM: Artificial
<220> FEATURE:
<223> OTHER INFORMATION: FPOX-9

<400> SEQUENCE: 2

| | | | | | | | | | | | | | | |
|---|---|---|---|---|---|---|---|---|---|---|---|---|---|---|
| Met | Ala | Pro | Arg | Ala | Asn | Thr | Lys | Ile | Ile | Val | Val | Gly | Gly | Gly |
| 1 | | | | 5 | | | | | 10 | | | | | 15 |

| | | | | | | | | | | | | | | |
|---|---|---|---|---|---|---|---|---|---|---|---|---|---|---|
| Thr | Met | Gly | Ser | Ser | Thr | Ala | Leu | His | Leu | Leu | Arg | Ala | Gly | Tyr | Thr |
| | | | 20 | | | | | 25 | | | | | 30 | | |

| | | | | | | | | | | | | | | |
|---|---|---|---|---|---|---|---|---|---|---|---|---|---|---|
| Pro | Ser | Asn | Ile | Thr | Val | Leu | Asp | Thr | Tyr | Pro | Ile | Pro | Ser | Ala | Gln |
| | | 35 | | | | | 40 | | | | | 45 | | | |

| | | | | | | | | | | | | | | |
|---|---|---|---|---|---|---|---|---|---|---|---|---|---|---|
| Ser | Ala | Gly | Tyr | Asp | Leu | Asn | Lys | Ile | Met | Ser | Ile | Arg | Leu | Arg | Asn |
| | 50 | | | | | 55 | | | | | 60 | | | | |

| | | | | | | | | | | | | | | |
|---|---|---|---|---|---|---|---|---|---|---|---|---|---|---|
| Lys | Pro | Asp | Leu | Gln | Leu | Tyr | Leu | Glu | Ala | Leu | Asp | Met | Trp | Lys | Asn |
| 65 | | | | | 70 | | | | | 75 | | | | | 80 |

| | | | | | | | | | | | | | | |
|---|---|---|---|---|---|---|---|---|---|---|---|---|---|---|
| Asp | Pro | Leu | Phe | Lys | Pro | Phe | Phe | His | Asn | Val | Gly | Gln | Met | Asp | Val |
| | | | | 85 | | | | | 90 | | | | | 95 | |

| | | | | | | | | | | | | | | |
|---|---|---|---|---|---|---|---|---|---|---|---|---|---|---|
| Ser | Ser | Thr | Glu | Glu | Gly | Ile | Lys | Gly | Leu | Arg | Met | Arg | Tyr | Gln | Ser |
| | | | | 100 | | | | | 105 | | | | | 110 | |

| | | | | | | | | | | | | | | |
|---|---|---|---|---|---|---|---|---|---|---|---|---|---|---|
| Leu | Leu | Asp | Ala | Gly | Ile | Gly | Leu | Glu | Lys | Thr | Asn | Phe | Leu | Leu | Glu |
| | | | 115 | | | | | 120 | | | | | 125 | | |

| | | | | | | | | | | | | | | |
|---|---|---|---|---|---|---|---|---|---|---|---|---|---|---|
| Ser | Glu | Asp | Glu | Ile | Leu | Ala | Lys | Ala | Pro | His | Phe | Thr | Arg | Glu | Gln |
| | 130 | | | | | 135 | | | | | 140 | | | | |

| | | | | | | | | | | | | | | |
|---|---|---|---|---|---|---|---|---|---|---|---|---|---|---|
| Ile | Lys | Gly | Trp | Lys | Gly | Leu | Phe | Cys | Gly | Asp | Gly | Gly | Trp | Leu | Ala |
| 145 | | | | | 150 | | | | | 155 | | | | | 160 |

| | | | | | | | | | | | | | | |
|---|---|---|---|---|---|---|---|---|---|---|---|---|---|---|
| Ala | Ala | Lys | Ala | Ile | Asn | Ala | Ile | Gly | Gln | Phe | Leu | Lys | Glu | Gln | Gly |
| | | | | 165 | | | | | 170 | | | | | 175 | |

| | | | | | | | | | | | | | | |
|---|---|---|---|---|---|---|---|---|---|---|---|---|---|---|
| Val | Lys | Phe | Gly | Phe | Gly | Gly | Ala | Gly | Thr | Phe | Lys | Lys | Pro | Leu | Phe |
| | | | 180 | | | | | 185 | | | | | 190 | | |

| | | | | | | | | | | | | | | |
|---|---|---|---|---|---|---|---|---|---|---|---|---|---|---|
| Ala | Asp | Ala | Asp | Glu | Lys | Thr | Cys | Ile | Gly | Val | Glu | Thr | Val | Asp | Gly |
| | 195 | | | | | 200 | | | | | 205 | | | | |

| | | | | | | | | | | | | | | |
|---|---|---|---|---|---|---|---|---|---|---|---|---|---|---|
| Thr | Lys | Tyr | Tyr | Ala | Asp | Lys | Val | Val | Leu | Ala | Ala | Gly | Ala | Trp | Ser |
| 210 | | | | | 215 | | | | | 220 | | | | | |

| | | | | | | | | | | | | | | |
|---|---|---|---|---|---|---|---|---|---|---|---|---|---|---|
| Ser | Thr | Leu | Val | Asp | Leu | Glu | Glu | Gln | Cys | Val | Ser | Lys | Ala | Trp | Val |
| 225 | | | | | 230 | | | | | 235 | | | | | 240 |

| | | | | | | | | | | | | | | |
|---|---|---|---|---|---|---|---|---|---|---|---|---|---|---|
| Phe | Ala | His | Ile | Gln | Leu | Thr | Pro | Ala | Glu | Ala | Ala | Tyr | Lys | Asn |
| | | | | 245 | | | | | 250 | | | | | 255 |

| | | | | | | | | | | | | | | |
|---|---|---|---|---|---|---|---|---|---|---|---|---|---|---|
| Thr | Pro | Val | Ile | Tyr | Asp | Gly | Asp | Tyr | Gly | Phe | Phe | Ile | Glu | Pro | Asn |
| | | | 260 | | | | | 265 | | | | | 270 | | |

| | | | | | | | | | | | | | | |
|---|---|---|---|---|---|---|---|---|---|---|---|---|---|---|
| Glu | Asn | Gly | Ile | Ile | Lys | Val | Cys | Asp | Glu | Phe | Pro | Gly | Phe | Thr | His |
| | | 275 | | | | | 280 | | | | | 285 | | | |

| | | | | | | | | | | | | | | |
|---|---|---|---|---|---|---|---|---|---|---|---|---|---|---|
| Phe | Lys | Met | His | Gln | Pro | Tyr | Gly | Ser | Pro | Val | Pro | Lys | Pro | Ile | Ser |
| | 290 | | | | | 295 | | | | | 300 | | | | |

| | | | | | | | | | | | | | | |
|---|---|---|---|---|---|---|---|---|---|---|---|---|---|---|
| Val | Pro | Arg | Ser | His | Ala | Lys | His | Pro | Thr | Asp | Thr | Tyr | Pro | His | Ala |
| 305 | | | | | 310 | | | | | 315 | | | | | 320 |

| | | | | | | | | | | | | | | |
|---|---|---|---|---|---|---|---|---|---|---|---|---|---|---|
| Ser | Glu | Val | Thr | Ile | Lys | Lys | Ala | Ile | Asn | Arg | Phe | Leu | Pro | Arg | Phe |
| | | | | 325 | | | | | 330 | | | | | 335 | |

| | | | | | | | | | | | | | | |
|---|---|---|---|---|---|---|---|---|---|---|---|---|---|---|
| Asn | Asp | Lys | Glu | Leu | Phe | Asn | Arg | Ala | Met | Cys | Trp | Cys | Thr | Asp | Thr |
| | | | 340 | | | | | 345 | | | | | 350 | | |

| | | | | | | | | | | | | | | |
|---|---|---|---|---|---|---|---|---|---|---|---|---|---|---|
| Ala | Asp | Ala | Asn | Leu | Leu | Val | Cys | Glu | His | Pro | Arg | Trp | Lys | Gly | Phe |
| | | 355 | | | | | 360 | | | | | 365 | | | |

| | | | | | | | | | | | | | | |
|---|---|---|---|---|---|---|---|---|---|---|---|---|---|---|
| Tyr | Leu | Ala | Thr | Gly | Asp | Ser | Gly | His | Ser | Phe | Lys | Leu | Leu | Pro | Asn |
| | 370 | | | | | 375 | | | | | 380 | | | | |

| | | | | | | | | | | | | | | |
|---|---|---|---|---|---|---|---|---|---|---|---|---|---|---|
| Ile | Gly | Lys | His | Val | Val | Glu | Leu | Leu | Glu | Gly | Arg | Leu | Glu | Ser | Val |

```
                    385                 390                 395                 400
        Phe Lys Asp Ala Trp Arg Trp Arg Pro Gly Ser Gly Asp Ala Leu Lys
                        405                 410                 415

Ser Arg Arg Ala Ala Pro Ala Lys Asp Leu Ala Asp Met Pro Gly Trp
                        420                 425                 430

Arg Asn Glu Ala Lys Met
                        435

<210> SEQ ID NO 3
<211> LENGTH: 438
<212> TYPE: PRT
<213> ORGANISM: Artificial
<220> FEATURE:
<223> OTHER INFORMATION: FPOX-16

<400> SEQUENCE: 3

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Gly Leu Arg Asn
        50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                    85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
```

```
            305                 310                 315                 320
Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435
```

<210> SEQ ID NO 4
<211> LENGTH: 438
<212> TYPE: PRT
<213> ORGANISM: Artificial
<220> FEATURE:
<223> OTHER INFORMATION: FPOX-17

<400> SEQUENCE: 4

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Ile Phe Gly Ile Ser Leu Arg Asn
            50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
            130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
```

```
                225                 230                 235                 240
        Phe Ala His Ile Gln Leu Thr Pro Ala Glu Ala Ala Tyr Lys Asn
                        245                 250                 255

Thr Pro Val Ile Tyr Asp Gly Asp Tyr Gly Phe Ile Glu Pro Asp
                        260                 265                 270

Glu Asn Gly Ile Ile Lys Val Cys Asp Glu Phe Pro Gly Phe Thr His
                        275                 280                 285

Phe Lys Met His Gln Pro Tyr Gly Ser Pro Val Pro Lys Leu Ile Ser
                        290                 295                 300

Val Pro Arg Ser His Ala Lys His Pro Thr Asp Thr Tyr Pro His Ala
        305                 310                 315                 320

Ser Glu Val Thr Ile Lys Lys Ala Ile Asn Arg Phe Leu Pro Arg Phe
                        325                 330                 335

Asn Asp Lys Glu Leu Phe Asn Arg Ala Met Cys Trp Cys Thr Asp Thr
                        340                 345                 350

Ala Asp Ala Asn Leu Leu Val Cys Glu His Pro Arg Trp Lys Gly Phe
                        355                 360                 365

Tyr Leu Ala Thr Gly Asp Ser Gly His Ser Phe Lys Leu Leu Pro Asn
                        370                 375                 380

Ile Gly Lys His Val Val Glu Leu Leu Glu Gly Arg Leu Glu Ser Val
        385                 390                 395                 400

Phe Lys Asp Ala Trp Arg Trp Arg Pro Gly Ser Gly Asp Ala Leu Lys
                        405                 410                 415

Ser Arg Arg Ala Ala Pro Ala Lys Asp Leu Ala Asp Met Pro Gly Trp
                        420                 425                 430

Arg Asn Glu Ala Lys Met
                        435

<210> SEQ ID NO 5
<211> LENGTH: 438
<212> TYPE: PRT
<213> ORGANISM: Artificial
<220> FEATURE:
<223> OTHER INFORMATION: FPOX-18

<400> SEQUENCE: 5

Met Ala Pro Arg Ala Asn Thr Lys Ile Ile Val Val Gly Gly Gly Gly
        1               5                   10                  15

Thr Met Gly Ser Ser Thr Ala Leu His Leu Leu Arg Ala Gly Tyr Thr
                        20                  25                  30

Pro Ser Asn Ile Thr Val Leu Asp Thr Tyr Pro Ile Pro Ser Ala Gln
                        35                  40                  45

Ser Ala Gly Tyr Asp Leu Asn Lys Ile Phe Gly Ile Ser Gly Ala Asn
                        50                  55                  60

Lys Pro Asp Leu Gln Leu Tyr Leu Glu Ala Leu Asp Met Trp Lys Asn
        65                  70                  75                  80

Asp Pro Leu Phe Lys Pro Phe His Asn Val Gly Gln Met Asp Val
                        85                  90                  95

Ser Ser Thr Glu Glu Gly Ile Lys Lys Leu Arg Met Arg Tyr Gln Ser
                        100                 105                 110

Leu Leu Asp Ala Gly Ile Gly Leu Glu Lys Thr Asn Phe Leu Leu Glu
                        115                 120                 125

Ser Glu Asp Glu Ile Leu Ala Lys Ala Pro His Phe Thr Arg Glu Gln
                        130                 135                 140

Ile Lys Gly Trp Lys Gly Leu Phe Cys Gly Asp Gly Gly Trp Leu Ala
```

```
            145                 150                 155                 160
    Ala Ala Lys Ala Ile Asn Ala Ile Gly Gln Phe Leu Lys Glu Gln Gly
                    165                 170                 175

Val Lys Phe Gly Phe Gly Glu Ala Gly Thr Phe Lys Lys Pro Leu Phe
                    180                 185                 190

Ala Asp Ala Asp Glu Lys Thr Cys Ile Gly Val Glu Thr Val Asp Gly
                    195                 200                 205

Thr Lys Tyr Tyr Ala Asp Lys Val Val Leu Ala Ala Gly Ala Trp Ser
                210                 215                 220

Ser Thr Leu Val Asp Leu Glu Glu Gln Cys Val Ser Lys Ala Trp Val
    225                 230                 235                 240

Phe Ala His Ile Gln Leu Thr Pro Ala Glu Ala Ala Tyr Lys Asn
                    245                 250                 255

Thr Pro Val Ile Tyr Asp Gly Asp Tyr Gly Phe Phe Ile Glu Pro Asp
                    260                 265                 270

Glu Asn Gly Ile Ile Lys Val Cys Asp Glu Phe Pro Gly Phe Thr His
                    275                 280                 285

Phe Lys Met His Gln Pro Tyr Gly Ser Pro Val Pro Lys Leu Ile Ser
                290                 295                 300

Val Pro Arg Ser His Ala Lys His Pro Thr Asp Thr Tyr Pro His Ala
    305                 310                 315                 320

Ser Glu Val Thr Ile Lys Lys Ala Ile Asn Arg Phe Leu Pro Arg Phe
                    325                 330                 335

Asn Asp Lys Glu Leu Phe Asn Arg Ala Met Cys Trp Cys Thr Asp Thr
                    340                 345                 350

Ala Asp Ala Asn Leu Leu Val Cys Glu His Pro Arg Trp Lys Gly Phe
                    355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Gly Arg Leu Glu Ser Val
    385                 390                 395                 400

Phe Lys Asp Ala Trp Arg Trp Arg Pro Gly Ser Gly Asp Ala Leu Lys
                    405                 410                 415

Ser Arg Arg Ala Ala Pro Ala Lys Asp Leu Ala Asp Met Pro Gly Trp
                    420                 425                 430

Arg Asn Glu Ala Lys Met
                435

<210> SEQ ID NO 6
<211> LENGTH: 438
<212> TYPE: PRT
<213> ORGANISM: Artificial
<220> FEATURE:
<223> OTHER INFORMATION: FPOX-18A

<400> SEQUENCE: 6

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Ile Phe Gly Ile Ser Gly Ala Asn
            50                  55                  60

Lys Pro Asp Leu Gln Leu Cys Leu Glu Ala Leu Asp Met Trp Lys Asn
```

```
            65                  70                  75                  80
Asp Pro Leu Phe Lys Pro Phe Phe His Asn Val Gly Gln Met Asp Val
                    85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
                115                 120                 125

Ser Glu Asp Glu Ile Leu Ala Lys Ala Pro His Phe Thr Arg Glu Gln
            130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                    165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                    245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                    325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                    405                 410                 415

Ser Arg Arg Ala Ala Pro Ala Lys Asp Leu Ala Asp Met Pro Gly Trp
                420                 425                 430

Arg Asn Glu Ala Lys Met
        435

<210> SEQ ID NO 7
<211> LENGTH: 438
<212> TYPE: PRT
<213> ORGANISM: Artificial
<220> FEATURE:
<223> OTHER INFORMATION: FPOX-18B
```

<400> SEQUENCE: 7

```
Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415
```

```
Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 8
<211> LENGTH: 438
<212> TYPE: PRT
<213> ORGANISM: Artificial
<220> FEATURE:
<223> OTHER INFORMATION: FPOX-18C

<400> SEQUENCE: 8

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asn Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335
```

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 9
<211> LENGTH: 438
<212> TYPE: PRT
<213> ORGANISM: Artificial
<220> FEATURE:
<223> OTHER INFORMATION: FPOX-18D

<400> SEQUENCE: 9

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

```
Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 10
<211> LENGTH: 438
<212> TYPE: PRT
<213> ORGANISM: Artificial
<220> FEATURE:
<223> OTHER INFORMATION: FPOX-19

<400> SEQUENCE: 10

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175
```

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 11
<211> LENGTH: 438
<212> TYPE: PRT
<213> ORGANISM: Artificial
<220> FEATURE:
<223> OTHER INFORMATION: FPOX-20

<400> SEQUENCE: 11

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Ala Asp Met Trp Lys Asn
65                  70                  75                  80

Asp Pro Leu Phe Lys Pro Phe Phe His Asn Val Gly Gln Met Asp Val
            85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 12
<211> LENGTH: 438
<212> TYPE: PRT
<213> ORGANISM: Artificial
<220> FEATURE:
<223> OTHER INFORMATION: FPOX-21

<400> SEQUENCE: 12

Met Ala Pro Arg Ala Asn Thr Lys Ile Ile Val Val Gly Gly Gly Gly
1               5                   10                  15

-continued

Thr Met Gly Ser Ser Thr Ala Leu His Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 13
<211> LENGTH: 438
<212> TYPE: PRT
<213> ORGANISM: Artificial
<220> FEATURE:
<223> OTHER INFORMATION: FPOX-22

<400> SEQUENCE: 13

Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65              70                  75                  80

Asp Pro Leu Phe Lys Pro Phe His Asn Val Gly Gln Met Asp Val
            85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145             150                 155                 160

Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225             230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305             310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 14
<211> LENGTH: 438
<212> TYPE: PRT
<213> ORGANISM: Artificial
<220> FEATURE:
<223> OTHER INFORMATION: FPOX-23

<400> SEQUENCE: 14

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly His Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

```
Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 15
<211> LENGTH: 438
<212> TYPE: PRT
<213> ORGANISM: Artificial
<220> FEATURE:
<223> OTHER INFORMATION: FPOX-24

<400> SEQUENCE: 15

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Val Phe Gly Ile Ser Gly Ala Asn
        50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190
```

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
    355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 16
<211> LENGTH: 438
<212> TYPE: PRT
<213> ORGANISM: Artificial
<220> FEATURE:
<223> OTHER INFORMATION: FPOX-25

<400> SEQUENCE: 16

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

```
Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 17
<211> LENGTH: 438
<212> TYPE: PRT
<213> ORGANISM: Artificial
<220> FEATURE:
<223> OTHER INFORMATION: FPOX-26

<400> SEQUENCE: 17

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30
```

-continued

```
Pro Ser Asn Ile Thr Val Leu Asp Thr Tyr Pro Ile Pro Ser Ala Gln
         35                  40                  45

Ser Ala Gly Tyr Asp Leu Asn Lys Ile Phe Gly Ile Ser Gly Ala Asn
 50                  55                  60

Lys Pro Asp Leu Gln Leu Ser Leu Glu Ala Phe Asp Met Trp Lys Asn
 65                  70                  75                  80

Asp Pro Leu Phe Lys Pro Phe Phe His Asn Val Gly Gln Met Glu Val
                 85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435
```

<210> SEQ ID NO 18
<211> LENGTH: 438
<212> TYPE: PRT
<213> ORGANISM: Artificial
<220> FEATURE:
<223> OTHER INFORMATION: FPOX-27

<400> SEQUENCE: 18

Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn

```
            370                 375                 380
Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 19
<211> LENGTH: 438
<212> TYPE: PRT
<213> ORGANISM: Artificial
<220> FEATURE:
<223> OTHER INFORMATION: FPOX-28

<400> SEQUENCE: 19

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys Pro Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Arg Arg Tyr Gln Ser
                100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
```

```
                290                 295                 300
Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 20
<211> LENGTH: 438
<212> TYPE: PRT
<213> ORGANISM: Artificial
<220> FEATURE:
<223> OTHER INFORMATION: FPOX-29

<400> SEQUENCE: 20

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Ile Phe Gly Ile Ser Gly Ala Asn
                50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
                100                 105                 110

Leu Leu Arg Ala Gly Ile Gly Leu Glu Lys Thr Asn Phe Leu Leu Glu
                115                 120                 125

Ser Glu Asp Glu Ile Leu Ala Lys Ala Pro His Phe Thr Arg Glu Gln
                130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
```

-continued

```
            210                 215                 220
Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 21
<211> LENGTH: 438
<212> TYPE: PRT
<213> ORGANISM: Artificial
<220> FEATURE:
<223> OTHER INFORMATION: FPOX-30

<400> SEQUENCE: 21

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
```

```
                130             135             140
Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 22
<211> LENGTH: 438
<212> TYPE: PRT
<213> ORGANISM: Artificial
<220> FEATURE:
<223> OTHER INFORMATION: FPOX-31

<400> SEQUENCE: 22

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
```

```
            50                  55                  60
Lys His Asp Leu Gln Leu Ser Leu Glu Ala Phe Asp Met Trp Lys Asn
 65                  70                  75                  80

Asp Pro Leu Phe Lys Pro Phe Phe His Asn Val Gly Gln Met Glu Val
                 85                  90                  95

Ser Ser Thr Glu Glu Gly Ile Lys Arg Leu Arg Lys Arg Tyr Gln Ser
                100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 23
<211> LENGTH: 438
<212> TYPE: PRT
<213> ORGANISM: Artificial
```

<220> FEATURE:
<223> OTHER INFORMATION: FPOX-32

<400> SEQUENCE: 23

```
Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400
```

```
Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 24
<211> LENGTH: 438
<212> TYPE: PRT
<213> ORGANISM: Artificial
<220> FEATURE:
<223> OTHER INFORMATION: FPOX-33

<400> SEQUENCE: 24

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320
```

```
Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
            420                 425                 430

Arg Asn Glu Ala Lys Met
            435
```

```
<210> SEQ ID NO 25
<211> LENGTH: 438
<212> TYPE: PRT
<213> ORGANISM: Artificial
<220> FEATURE:
<223> OTHER INFORMATION: FPOX-34

<400> SEQUENCE: 25
```

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
            35                  40                  45

Ser Ala Gly His Asp Leu Asn Lys Ile Phe Gly Ile Ser Gly Ala Asn
            50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
            85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
            130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240
```

```
Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 26
<211> LENGTH: 438
<212> TYPE: PRT
<213> ORGANISM: Artificial
<220> FEATURE:
<223> OTHER INFORMATION: FPOX-35

<400> SEQUENCE: 26

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Val Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160
```

Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 27
<211> LENGTH: 438
<212> TYPE: PRT
<213> ORGANISM: Artificial
<220> FEATURE:
<223> OTHER INFORMATION: FPOX-36

<400> SEQUENCE: 27

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

```
Asp Pro Leu Phe Lys Pro Phe His Asn Val Gly Gln Met Asp Val
                 85                  90                  95

Ser Ser Thr Glu Glu Gly Ile Lys Lys Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 28
<211> LENGTH: 438
<212> TYPE: PRT
<213> ORGANISM: Artificial
<220> FEATURE:
<223> OTHER INFORMATION: FPOX-37

<400> SEQUENCE: 28

-continued

Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
        20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

-continued

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 29
<211> LENGTH: 438
<212> TYPE: PRT
<213> ORGANISM: Artificial
<220> FEATURE:
<223> OTHER INFORMATION: FPOX-38

<400> SEQUENCE: 29

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
            85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

```
Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 30
<211> LENGTH: 438
<212> TYPE: PRT
<213> ORGANISM: Artificial
<220> FEATURE:
<223> OTHER INFORMATION: FPOX-39

<400> SEQUENCE: 30

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255
```

-continued

```
Thr Pro Val Ile Tyr Asp Gly Asp Tyr Gly Phe Phe Ile Glu Pro Asp
            260                 265                 270

Glu Asn Gly Ile Ile Lys Val Cys Asp Glu Pro Gly Phe Thr His
        275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435
```

```
<210> SEQ ID NO 31
<211> LENGTH: 438
<212> TYPE: PRT
<213> ORGANISM: Artificial
<220> FEATURE:
<223> OTHER INFORMATION: FPOX-40

<400> SEQUENCE: 31
```

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175
```

```
Val Lys Phe Gly Phe Gly Glu Ala Gly Thr Phe Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
        260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 32
<211> LENGTH: 438
<212> TYPE: PRT
<213> ORGANISM: Artificial
<220> FEATURE:
<223> OTHER INFORMATION: FPOX-41

<400> SEQUENCE: 32

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95
```

```
Ser Ser Thr Glu Glu Gly Ile Lys Lys Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 33
<211> LENGTH: 438
<212> TYPE: PRT
<213> ORGANISM: Artificial
<220> FEATURE:
<223> OTHER INFORMATION: FPOX-42

<400> SEQUENCE: 33

Met Ala Pro Arg Ala Asn Thr Lys Ile Ile Val Val Gly Gly Gly Gly
1               5                   10                  15
```

```
Thr Met Gly Ser Ser Thr Ala Leu His Leu Leu Arg Ala Gly Tyr Thr
            20                  25                  30
Pro Ser Asn Ile Thr Val Leu Asp Thr Tyr Pro Ile Pro Ser Ala Gln
        35                  40                  45
Ser Ala Gly Tyr Asp Leu Asn Lys Ile Phe Gly Ile Ser Gly Ala Asn
 50                  55                  60
Lys His Asp Leu Gln Leu Ser Leu Glu Ala Phe Asp Met Trp Lys Asn
 65                  70                  75                  80
Asp Pro Leu Phe Lys Pro Phe Phe His Asn Val Gly Gln Met Asp Val
                85                  90                  95
Ser Ser Thr Glu Glu Gly Ile Lys Arg Leu Arg Arg Tyr Gln Ser
            100                 105                 110
Leu Leu Arg Ala Gly Ile Gly Leu Glu Lys Thr Asn Phe Leu Leu Glu
            115                 120                 125
Ser Glu Asp Glu Ile Leu Ala Lys Ala Pro His Phe Thr Arg Glu Gln
            130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
            180                 185                 190
Ala Asp Ala Asp Glu Lys Thr Cys Ile Gly Val Glu Thr Val Asp Gly
            195                 200                 205
Thr Lys Tyr Tyr Ala Asp Lys Val Val Leu Ala Ala Gly Ala Trp Ser
210                 215                 220
Ser Thr Leu Val Asp Leu Glu Glu Gln Cys Val Ser Lys Ala Trp Val
225                 230                 235                 240
Phe Ala His Ile Gln Leu Thr Pro Ala Glu Ala Ala Tyr Lys Asn
                245                 250                 255
Thr Pro Val Ile Tyr Asp Gly Asp Tyr Gly Phe Phe Ile Glu Pro Asp
            260                 265                 270
Glu Asn Gly Ile Ile Lys Val Cys Asp Glu Phe Pro Gly Phe Thr His
            275                 280                 285
Phe Lys Met His Gln Pro Tyr Gly Ser Pro Val Pro Lys Leu Ile Ser
290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
            340                 345                 350
Ala Asp Ser Asn Leu Leu Val Cys Glu His Pro Arg Trp Lys Gly Phe
            355                 360                 365
Tyr Leu Ala Thr Gly Asp Ser Gly His Ser Phe Lys Leu Leu Pro Asn
            370                 375                 380
Ile Gly Lys His Val Val Glu Leu Leu Glu Gly Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
```

<210> SEQ ID NO 34
<211> LENGTH: 438
<212> TYPE: PRT
<213> ORGANISM: Artificial
<220> FEATURE:
<223> OTHER INFORMATION: FPOX-43

<400> SEQUENCE: 34

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe

```
            355                 360                 365
Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 35
<211> LENGTH: 438
<212> TYPE: PRT
<213> ORGANISM: Artificial
<220> FEATURE:
<223> OTHER INFORMATION: FPOX-44

<400> SEQUENCE: 35

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly His Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
```

```
            275                 280                 285
Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 36
<211> LENGTH: 438
<212> TYPE: PRT
<213> ORGANISM: Artificial
<220> FEATURE:
<223> OTHER INFORMATION: FPOX-45

<400> SEQUENCE: 36

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Val Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
```

```
                    195                 200                 205
Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 37
<211> LENGTH: 438
<212> TYPE: PRT
<213> ORGANISM: Artificial
<220> FEATURE:
<223> OTHER INFORMATION: FPOX-46

<400> SEQUENCE: 37

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
```

```
            115                 120                 125
Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 38
<211> LENGTH: 436
<212> TYPE: PRT
<213> ORGANISM: Artificial
<220> FEATURE:
<223> OTHER INFORMATION: AoFPOX

<400> SEQUENCE: 38

Met Thr Val Thr Lys Ser Ser Ile Leu Ile Ile Gly Ala Gly Thr
1               5                   10                  15

Trp Gly Ala Ser Thr Ala Leu His Leu Gly Arg Arg Gly Tyr Thr Asn
            20                  25                  30

Val Thr Val Leu Asp Pro Tyr Thr Val Pro Ser Ala Ile Ser Ala Gly
```

```
            35                  40                  45
Asn Asp Val Asn Lys Ile Ile Ser Ser Gly Gln Tyr Ser Asn Lys Lys
 50                  55                  60

Asp Glu Ile Glu Val Asn Glu Ile Leu Ala Glu Ala Phe Lys Gly
 65                  70                  75                  80

Trp Thr Thr Asp Pro Leu Phe Lys Pro Tyr Tyr His Asp Thr Gly Val
                 85                  90                  95

Val Met Ser Ala Cys Ser Ser Ala Gly Leu Asp Arg Leu Gly Ile Arg
                100                 105                 110

Val Arg Pro Glu Glu Pro Asp Val Ser Glu Val Thr Lys Pro Glu
                115                 120                 125

His Phe Arg Gln Leu Ala Pro Ala Val Leu Lys Gly Asn Phe Pro Gly
                130                 135                 140

Trp Arg Gly Tyr His Ile Arg Ser Asn Ala Gly Trp Ala His Ala Arg
145                 150                 155                 160

Asn Ala Leu Val Ala Ile Arg Glu Ala Glu Lys Leu Gly Val Lys
                165                 170                 175

Phe Val Thr Gly Thr Gln Gly Arg Val Ile Thr Leu Ile Phe Glu Asn
                180                 185                 190

Asn Asp Val Lys Gly Ala Val Thr Ala Asp Gly Lys Ile Trp Arg Ala
                195                 200                 205

Glu Gln Thr Val Leu Cys Ala Gly Ala Asn Ala Ala Gln Phe Leu Asp
                210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Glu Pro Asp Glu Arg Gly Glu
                260                 265                 270

Ile Lys Ile Cys Asp Glu His Pro Gly Tyr Thr Asn Met Val Lys Ser
                275                 280                 285

Ala Asp Gly His Leu Thr Ser Leu Pro Phe Gly Lys Thr Gln Ile Pro
290                 295                 300

Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
                340                 345                 350

Ser Leu Val Leu Gly Cys Gly Ala Ser Gly Arg Gly Phe Lys Tyr Leu
                355                 360                 365

Pro Ser Ile Gly Asn Leu Ile Val Asp Ala Ile Glu Asp Lys Val Pro
                370                 375                 380

Glu Lys Val His Lys Leu Thr Arg Trp Ser Pro Asp Ile Ala Val Asp
385                 390                 395                 400

Arg Lys Trp Arg Asp Thr Leu Gly Arg Phe Gly Gly Pro Asn Arg Val
                        405                 410                 415

Met Asp Phe His Asp Val Lys Glu Trp Thr Asn Val Gln Asn Lys Asp
                420                 425                 430

Thr Ala Lys Leu
                435

<210> SEQ ID NO 39
```

```
<211> LENGTH: 1317
<212> TYPE: DNA
<213> ORGANISM: Artificial
<220> FEATURE:
<223> OTHER INFORMATION: FPOX-15

<400> SEQUENCE: 39
atggcgcccc gagccaacac caaaatcatc gtcgtcggcg gcggcggcac aatgggctcg      60
tcgacagccc tacacctcct gcgcgccggc tacgccgt ccaacatcac agtgctcgac       120
acgtacccta tcccttccgc acagtctgca ggctacgacc tgaacaaaat cttcggcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaaagcttcg catgagatac cagtctcttc tcgacgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317

<210> SEQ ID NO 40
<211> LENGTH: 1317
<212> TYPE: DNA
<213> ORGANISM: Artificial
<220> FEATURE:
<223> OTHER INFORMATION: FPOX-9

<400> SEQUENCE: 40
atggcgcccc gagccaacac caaaatcatc gtcgtcggcg gcggcggcac aatgggctcg      60
tcgacagccc tacacctcct gcgcgccggc tacgccgt ccaacatcac agtgctcgac       120
acgtacccta tcccttccgc acagtctgca ggctacgacc tgaacaaaat catgagcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaggtcttcg catgagatac cagtctcttc tcgacgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
```

```
tttggcggcg ccggcacgtt caaaaagcca ctcttcgccg atgccgacga aagacgtgc      600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccgaatgaga acggcatcat aaaagtctgc      840
gacgaattcc ctggcttcac gcacttcaag atgcaccagc cgtacggctc accggtgccc      900
aaaccaatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 41
<211> LENGTH: 1317
<212> TYPE: DNA
<213> ORGANISM: Artificial
<220> FEATURE:
<223> OTHER INFORMATION: FPOX-16

<400> SEQUENCE: 41

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaaaat cttcggcatc      180
ggcctgcgca acaagcctga cttacaactc tatcttgagg cgctggacat gtggaaaaat      240
gatcctctat tcaagccgtt tttccacaat gttggacaga tggacgtctc ttcaacagaa      300
gaaggcatca aaaagcttcg catgagatac cagtctcttc tcgacgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
```

```
gcgcctgcga aggacctggc ggatatgccg gggtggagga atgaggcaaa gatgtag       1317
```

<210> SEQ ID NO 42
<211> LENGTH: 1317
<212> TYPE: DNA
<213> ORGANISM: Artificial
<220> FEATURE:
<223> OTHER INFORMATION: FPOX-17

<400> SEQUENCE: 42

```
atggcgcccc gagccaacac caaaatcatc gtcgtcggcg gcggcggcac aatgggctcg        60
tcgacagccc tacacctcct gcgcgccggc tacgccgt ccaacatcac agtgctcgac         120
acgtacccta tcccttccgc acagtctgca ggctacgacc tgaacaaaat cttcggcatc       180
tcactgcgca acaagcctga cttacaactc tatcttgagg cgctggacat gtggaaaaat       240
gatcctctat tcaagccgtt tttccacaat gttggacaga tggacgtctc ttcaacagaa       300
gaaggcatca aaaagcttcg catgagatac cagtctcttc tcgacgcagg cattgggctc       360
gagaagacga atttcctgct ggaaagtgaa gacgagatcc tggctaaagc gccgcatttc       420
acgcgggagc agattaaagg ctggaaaggg ctgttctgtg gcgacggcgg ttggctcgct       480
gcagccaaag ccatcaatgc catcgggcag ttcctcaagg aacagggcgt caagtttgga       540
tttggcgagg ccggcacgtt caaaaagcca ctcttcgccg atgccgacga aagacgtgc        600
atcggcgtcg aaactgtaga cggcacaaaa tactacgccg acaaggtcgt tctagcagct       660
ggtgcctgga gttcgacgtt ggtcgatctg gaggagcagt gcgtttcaaa ggcctgggtc       720
tttgcccaca tccaactgac gcccgctgaa gcagccgcgt acaagaacac tcctgttata       780
tacgacggtg actatgggtt tttcattgag ccggacgaga acggcatcat aaaagtctgc       840
gacgaattcc ctggcttcac gcacttcaag atgcaccagc cgtacggctc accggtgccc       900
aaattgatct ctgtgcctcg ctcccatgcg aagcacccca cagatacata cccgcacgcg       960
tcggaggtca ccatcaaaaa ggctatcaac cggttcctgc cgaggttcaa tgacaaggaa      1020
ctgtttaaca gggccatgtg ctggtgcacc gataccgcgg atgcaaatct gcttgtttgt      1080
gagcatccac gctggaaggg gttttatctt gcaacagggg acagcgggca ttcgttcaag      1140
ttgctgccga atattggaaa gcacgttgtc gagttattgg aggggaggct ggaaagtgtg      1200
tttaaggatg cttggaggtg gaggcctggc agtggggatg cattaaagag tagacgggct      1260
gcgcctgcga aggacctggc ggatatgccg gggtggagga atgaggcaaa gatgtag        1317
```

<210> SEQ ID NO 43
<211> LENGTH: 1317
<212> TYPE: DNA
<213> ORGANISM: Artificial
<220> FEATURE:
<223> OTHER INFORMATION: FPOX-18

<400> SEQUENCE: 43

```
atggcgcccc gagccaacac caaaatcatc gtcgtcggcg gcggcggcac aatgggctcg        60
tcgacagccc tacacctcct gcgcgccggc tacgccgcgt ccaacatcac agtgctcgac        120
acgtacccta tcccttccgc acagtctgca ggctacgacc tgaacaaaat cttcggcatc       180
tcaggcgcga acaagcctga cttacaactc tatcttgagg cgctggacat gtggaaaaat       240
gatcctctat tcaagccgtt tttccacaat gttggacaga tggacgtctc ttcaacagaa       300
gaaggcatca aaaagcttcg catgagatac cagtctcttc tcgacgcagg cattgggctc       360
gagaagacga atttcctgct ggaaagtgaa gacgagatcc tggctaaagc gccgcatttc       420
```

```
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 44
<211> LENGTH: 1317
<212> TYPE: DNA
<213> ORGANISM: Artificial
<220> FEATURE:
<223> OTHER INFORMATION: FPOX-18A

<400> SEQUENCE: 44

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc tgccttgagg cgctggacat gtggaaaaat    240
gatcctctat tcaagccgtt tttccacaat gttggacaga tggacgtctc ttcaacagaa    300
gaaggcatca aaaagcttcg catgagatac cagtctcttc tcgacgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
```

```
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag     1317
```

<210> SEQ ID NO 45
<211> LENGTH: 1317
<212> TYPE: DNA
<213> ORGANISM: Artificial
<220> FEATURE:
<223> OTHER INFORMATION: FPOX-18B
<400> SEQUENCE: 45

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac   120
acgtacccta tcccttccgc acagtctgca ggctacgacc tgaacaagat cttcggcatc   180
tcaggcgcga acaagcctga cttacaactc agccttgagg cgctggacat gtggaaaaat   240
gatcctctat tcaagccgtt tttccacaat gttggacaga tggacgtctc ttcaacagaa   300
gaaggcatca aaaagcttcg catgagatac cagtctcttc tcgacgcagg cattgggctc   360
gagaagacga atttcctgct ggaaagtgaa gacgagatcc tggctaaagc gccgcatttc   420
acgcgggagc agattaaagg ctggaaaggg ctgttctgtg gcgacggcgg ttggctcgct   480
gcagccaaag ccatcaatgc catcgggcag ttcctcaagg aacagggcgt caagtttgga   540
tttggcgagg ccggcacgtt caaaaagcca ctcttcgccg atgccgacga agacgtgcc    600 atcggcgtcg aaactgtaga cggcacaaaa tactacgccg acaaggtcgt tctagcagct   660
ggtgcctgga gttcgacgtt ggtcgatctg gaggagcagt gcgtttcaaa ggcctgggtc   720
tttgcccaca tccaactgac gcccgctgaa gcagccgcgt acaagaacac tcctgttata   780
tacgacggtg actatgggtt tttcattgag ccggacgaga acggcatcat aaaagtctgc   840
gacgaattcc ctggcttcac gcacttcaag atgcaccagc cgtacggctc accggtgccc   900
aaattgatct ctgtgcctcg ctcccatgcg aagcacccca cagatacata cccgcacgcg   960
tcggaggtca ccatcaaaaa ggctatcaac cggttcctgc cgaggttcaa tgacaaggaa  1020
ctgtttaaca gggccatgtg ctggtgcacc gataccgcgg atgcaaatct gcttgtttgt  1080
gagcatccac gctggaaggg gttttatctt gcaacagggg acagcgggca ttcgttcaag  1140
ttgctgccga atattggaaa gcacgttgtc gagttattgg aggggaggct ggaaagtgtg  1200
tttaaggatg cttggaggtg gaggcctggc agtggggatg cattaaagag tagacgggct  1260
gcgcctgcga aggacctggc ggatatgccg gggtggagga atgaggcaaa gatgtag    1317
```

<210> SEQ ID NO 46
<211> LENGTH: 1317
<212> TYPE: DNA
<213> ORGANISM: Artificial
<220> FEATURE:
<223> OTHER INFORMATION: FPOX-18C
<400> SEQUENCE: 46

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac   120
acgtacccta tcccttccgc acagtctgca ggctacgacc tgaacaagat cttcggcatc   180
tcaggcgcga acaagcctga cttacaactc agccttgagg cgctggacat gtggaaaaat   240
gatcctctat tcaagccgtt tttccacaat gttggacaga tggacgtctc ttcaacagaa   300
```

```
gaaggcatca aaaagcttcg catgagatac cagtctcttc tcaacgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga agacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag       1317
```

<210> SEQ ID NO 47
<211> LENGTH: 1317
<212> TYPE: DNA
<213> ORGANISM: Artificial
<220> FEATURE:
<223> OTHER INFORMATION: FPOX-18D

<400> SEQUENCE: 47

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaagat cttcggcatc      180
tcaggcgcga caagcctga cttacaactc agccttgagg cgctggacat gtggaaaaat      240
gatcctctat tcaagccgtt tttccacaat gttggacaga tggacgtctc ttcaacagaa      300
gaaggcatca aaaagcttcg catgagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga agacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
```

| | |
|---|---|
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 48
<211> LENGTH: 1317
<212> TYPE: DNA
<213> ORGANISM: Artificial
<220> FEATURE:
<223> OTHER INFORMATION: FPOX-19

<400> SEQUENCE: 48

| | |
|---|---|
| atggcgcccc gagccaacac caaaatcatc gtcgtcggcg gcggcggcac aatgggctcg | 60 |
| tcgacagccc tacacctcct gcgcgccggc tacgccgt ccaacatcac agtgctcgac | 120 |
| acgtacccta tcccttccgc acagtctgca ggctacgacc tgaacaagat cttcggcatc | 180 |
| tcaggcgcga acaagcctga cttacaactc agccttgagg cgctggacat gtggaaaaat | 240 |
| gatcctctat tcaagccgtt ttttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaagggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga agacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcaccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 49
<211> LENGTH: 1317
<212> TYPE: DNA
<213> ORGANISM: Artificial
<220> FEATURE:
<223> OTHER INFORMATION: FPOX-20

<400> SEQUENCE: 49

| | |
|---|---|
| atggcgcccc gagccaacac caaaatcatc gtcgtcggcg gcggcggcac aatgggctcg | 60 |
| tcgacagccc tacacctcct gcgcgccggc tacgccgt ccaacatcac agtgctcgac | 120 |
| acgtacccta tcccttccgc acagtctgca ggctacgacc tgaacaagat cttcggcatc | 180 |

-continued

```
tcaggcgcga acaagcctga cttacaactc agccttgagg cggccgacat gtggaaaaat      240
gatcctctat tcaagccgtt tttccacaat gttggacaga tggacgtctc ttcaacagaa      300
gaaggcatca aaaagcttcg caaaagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga agacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgc acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 50
<211> LENGTH: 1317
<212> TYPE: DNA
<213> ORGANISM: Artificial
<220> FEATURE:
<223> OTHER INFORMATION: FPOX-21

<400> SEQUENCE: 50

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaagat cttcggcatc      180
tcaggcgcga acaagcctga cttacaactc tcgcttgagg cgttcgacat gtggaaaaat      240
gatcctctat tcaagccgtt tttccacaat gttggacaga tggacgtctc ttcaacagaa      300
gaaggcatca aaaagcttcg caaaagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga agacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
```

| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 51
<211> LENGTH: 1317
<212> TYPE: DNA
<213> ORGANISM: Artificial
<220> FEATURE:
<223> OTHER INFORMATION: FPOX-22

<400> SEQUENCE: 51

| atggcgcccc gagccaacac caaaatcatc gtcgtcggcg gcggcggcac aatgggctcg | 60 |
| tcgacagccc tacacctcct gcgcgccggc tacacgccga ccaacatcac agtgctcgac | 120 |
| acgtacccta tcccttccgc acagtctgca ggctacgacc tgaacaagat cttcggcatc | 180 |
| tcaggcgcga acaagcctga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga agacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 52
<211> LENGTH: 1317
<212> TYPE: DNA
<213> ORGANISM: Artificial
<220> FEATURE:
<223> OTHER INFORMATION: FPOX-23

<400> SEQUENCE: 52

| atggcgcccc gagccaacac caaaatcatc gtcgtcggcg gcggcggcac aatgggctcg | 60 |

-continued

```
tcgacagccc tacacctcct gcgcgccggc tacacgccgt ccaacatcac agtgctcgac    120
acgtacccta tcccttccgc acagtctgca ggccatgacc tgaacaagat cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gtttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 53
<211> LENGTH: 1317
<212> TYPE: DNA
<213> ORGANISM: Artificial
<220> FEATURE:
<223> OTHER INFORMATION: FPOX-24

<400> SEQUENCE: 53

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaaggt cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
```

| | |
|---|---|
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 54
<211> LENGTH: 1317
<212> TYPE: DNA
<213> ORGANISM: Artificial
<220> FEATURE:
<223> OTHER INFORMATION: FPOX-25

<400> SEQUENCE: 54

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga caagcatga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaagggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga agacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 55
<211> LENGTH: 1317
<212> TYPE: DNA
<213> ORGANISM: Artificial
<220> FEATURE:
<223> OTHER INFORMATION: FPOX-26

<400> SEQUENCE: 55

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggaagtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttgcgaggc cggcacgtt caaaaagcca ctcttcgccg atgccgacga aagacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga tgaggcaaa gatgtag        1317
```

<210> SEQ ID NO 56
<211> LENGTH: 1317
<212> TYPE: DNA
<213> ORGANISM: Artificial
<220> FEATURE:
<223> OTHER INFORMATION: FPOX-27

<400> SEQUENCE: 56

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggacgtctc ttcaacagaa     300
gaaggcatca aacgccttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttgcgaggc cggcacgtt caaaaagcca ctcttcgccg atgccgacga aagacgtgc      600
atcggcgtcg aaactgtaga cggcacaaaa tactacgccg acaaggtcgt tctagcagct     660
```

```
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga tgaggcaaa gatgtag       1317
```

<210> SEQ ID NO 57
<211> LENGTH: 1317
<212> TYPE: DNA
<213> ORGANISM: Artificial
<220> FEATURE:
<223> OTHER INFORMATION: FPOX-28

<400> SEQUENCE: 57

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga agacgtgc      600
atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga tgaggcaaa gatgtag       1317
```

<210> SEQ ID NO 58
<211> LENGTH: 1317

```
<212> TYPE: DNA
<213> ORGANISM: Artificial
<220> FEATURE:
<223> OTHER INFORMATION: FPOX-29

<400> SEQUENCE: 58
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggacgtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga tgaggcaaa gatgtag        1317

<210> SEQ ID NO 59
<211> LENGTH: 1317
<212> TYPE: DNA
<213> ORGANISM: Artificial
<220> FEATURE:
<223> OTHER INFORMATION: FPOX-30

<400> SEQUENCE: 59
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
```

```
tttggcgagg ccggcacgtt caaaaagcca ctcttcgccg atgccgacga gaagacgtgc      600
atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 60
<211> LENGTH: 1317
<212> TYPE: DNA
<213> ORGANISM: Artificial
<220> FEATURE:
<223> OTHER INFORMATION: FPOX-31

<400> SEQUENCE: 60

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaagat cttcggcatc      180
tcaggcgcga acaagcatga cttacaactc tcgcttgagg cgttcgacat gtggaaaaat      240
gatcctctat tcaagccgtt tttccacaat gttggacaga tggaagtctc ttcaacagaa      300
gaaggcatca aacgccttcg caaaagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga gaagacgtgc      600
atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 61
<211> LENGTH: 1317
<212> TYPE: DNA
<213> ORGANISM: Artificial
<220> FEATURE:
<223> OTHER INFORMATION: FPOX-32

<400> SEQUENCE: 61

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccgt | ccaacatcac | agtgctcgac | 120 |
| acgtacccta | tcccttccgc | acagtctgca | ggctacgacc | tgaacaagat | cttcggcatc | 180 |
| tcaggcgcga | acaagcatga | cttacaactc | tcgcttgagg | cgttcgacat | gtggaaaaat | 240 |
| gatcctctat | tcaagccgtt | tttccacaat | gttggacaga | tggaagtctc | ttcaacagaa | 300 |
| gaaggcatca | aacgccttcg | ccgcagatac | cagtctcttc | tccgcgcagg | cattgggctc | 360 |
| gagaagacga | atttcctgct | ggaaagtgaa | gacgagatcc | tggctaaagc | gccgcatttc | 420 |
| acgcgggagc | agattaaagg | ctggaaaggg | ctgttctgtg | gcgacggcgg | ttggctcgct | 480 |
| gcagccaaag | ccatcaatgc | catcgggcag | ttcctcaagg | aacagggcgt | caagtttgga | 540 |
| tttggcgagg | ccggcacgtt | caaaaagcca | ctcttcgccg | atgccgacga | aagacgtgc | 600 |
| atcggcgtcg | aaactgtaga | cggcacaaaa | tactacgccg | acaaggtcgt | tctagcagct | 660 |
| ggtgcctgga | gttcgacgtt | ggtcgatctg | gaggagcagt | gcgtttcaaa | ggcctgggtc | 720 |
| tttgcccaca | tccaactgac | gcccgctgaa | gcagccgcgt | acaagaacac | tcctgttata | 780 |
| tacgacggtg | actatgggtt | tttcattgag | ccggacgaga | acggcatcat | aaaagtctgc | 840 |
| gacgaattcc | ctggcttcac | gcacttcaag | atgcaccagc | cgtacggctc | accggtgccc | 900 |
| aaattgatct | ctgtgcctcg | ctcccatgcg | aagcacccca | cagatacata | cccgcacgcg | 960 |
| tcggaggtca | ccatcaaaaa | ggctatcaac | cggttcctgc | cgaggttcaa | tgacaaggaa | 1020 |
| ctgtttaaca | gggccatgtg | ctggtgcacc | gataccgcgg | atgcaaatct | gcttgtttgt | 1080 |
| gagcatccac | gctggaaggg | gttttatctt | gcaacagggg | acagcgggca | ttcgttcaag | 1140 |
| ttgctgccga | atattggaaa | gcacgttgtc | gagttattgg | aggggaggct | ggaaagtgtg | 1200 |
| tttaaggatg | cttggaggtg | gaggcctggc | agtggggatg | cattaaagag | tagacgggct | 1260 |
| gcgcctgcga | aggacctggc | ggatatgccg | gggtggagga | atgaggcaaa | gatgtag | 1317 |

<210> SEQ ID NO 62
<211> LENGTH: 1317
<212> TYPE: DNA
<213> ORGANISM: Artificial
<220> FEATURE:
<223> OTHER INFORMATION: FPOX-33

<400> SEQUENCE: 62

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccga | ccaacatcac | agtgctcgac | 120 |
| acgtacccta | tcccttccgc | acagtctgca | ggctacgacc | tgaacaagat | cttcggcatc | 180 |
| tcaggcgcga | acaagcatga | cttacaactc | tcgcttgagg | cgttcgacat | gtggaaaaat | 240 |
| gatcctctat | tcaagccgtt | tttccacaat | gttggacaga | tggaagtctc | ttcaacagaa | 300 |
| gaaggcatca | aacgccttcg | ccgcagatac | cagtctcttc | tccgcgcagg | cattgggctc | 360 |
| gagaagacga | atttcctgct | ggaaagtgaa | gacgagatcc | tggctaaagc | gccgcatttc | 420 |

| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtgggatg cattaaagag tagacgggct | 1260 |
| gcgcctgcga aggacctggc ggatatgccg gggtggagga atgaggcaaa gatgtag | 1317 |

<210> SEQ ID NO 63
<211> LENGTH: 1317
<212> TYPE: DNA
<213> ORGANISM: Artificial
<220> FEATURE:
<223> OTHER INFORMATION: FPOX-34

<400> SEQUENCE: 63

| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggccatgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggaagtctc ttcaacagaa | 300 |
| gaaggcatca aacgccttcg ccgcagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |

<210> SEQ ID NO 64
<211> LENGTH: 1317
<212> TYPE: DNA
<213> ORGANISM: Artificial
<220> FEATURE:
<223> OTHER INFORMATION: FPOX-35

<400> SEQUENCE: 64

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaggt cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aacgccttcg ccgcagatac cagtctcttc tccgcgcagg cattgggctc     360
gagaagacga atttcctgct ggaaagtgaa gacgagatcc tggctaaagc gccgcatttc     420
acgcgggagc agattaaagg ctggaagggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga agacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatg cattaaagag tagacgggct    1260
gcgcctgcga aggacctggc ggatatgccg gggtggagga atgaggcaaa gatgtag       1317
```

<210> SEQ ID NO 65
<211> LENGTH: 1317
<212> TYPE: DNA
<213> ORGANISM: Artificial
<220> FEATURE:
<223> OTHER INFORMATION: FPOX-36

<400> SEQUENCE: 65

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggacgtctc ttcaacagaa     300
```

| | |
|---|---|
| gaaggcatca aaaagcttcg ccgcagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gtttatcttt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtgggatgc attaaagag tagacgggct | 1260 |
| gcgcctgcga aggacctggc ggatatgccg gggtggagga tgaggcaaa gatgtag | 1317 |

<210> SEQ ID NO 66
<211> LENGTH: 1317
<212> TYPE: DNA
<213> ORGANISM: Artificial
<220> FEATURE:
<223> OTHER INFORMATION: FPOX-37

<400> SEQUENCE: 66

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tccccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt ttttccacaat gttggacaga tggacgtctc ttcaacagaa | 300 |
| gaaggcatca aacgccttcg ccgcagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |

| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 67
<211> LENGTH: 1317
<212> TYPE: DNA
<213> ORGANISM: Artificial
<220> FEATURE:
<223> OTHER INFORMATION: FPOX-38

<400> SEQUENCE: 67

| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atagcaatct gcttgttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 68
<211> LENGTH: 1317
<212> TYPE: DNA
<213> ORGANISM: Artificial
<220> FEATURE:
<223> OTHER INFORMATION: FPOX-39

<400> SEQUENCE: 68

| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |

```
tcaggcgcga acaagcatga cttacaactc tcgcttgagg cgttcgacat gtggaaaaat        240
gatcctctat tcaagccgtt tttccacaat gttggacaga tggaagtctc ttcaacagaa        300
gaaggcatca aaaagcttcg caaaagatac cagtctcttc tccgcgcagg cattgggctc        360
gagaagacga atttcctgct ggaaagtgaa gacgagatcc tggctaaagc gccgcatttc        420
acgcgggagc agattaaagg ctggaaaggg ctgttctgtg gcgacggcgg ttggctcgct        480
gcagccaaag ccatcaatgc catcgggcag ttcctcaagg aacagggcgt caagtttgga        540
tttggcgagg ccggcacgtt caaaaagcca ctcttcgccg atgccgacga aagacgtgc         600 atcggcgtcg aaactgtaga cggcacaaaa tactacgccg acaaggtcgt tctagcagct        660
ggtgcctgga gttcgacgtt ggtcgatctg gaggagcagt gcgtttcaaa ggcctgggtc        720
tttgcccaca tccaactgac gcccgctgaa gcagccgcgt acaagaacac tcctgttata        780
tacgacggtg actatgggtt tttcattgag ccggacgaga acggcatcat aaaagtctgc        840
gacgaattcc ctggcttcac gcacttcaag atgcaccagc cgtacggctc accggtgccc        900
aaattgatct ctgtgcctcg ctcccatgcg aagcacccca cagatacata cccgcacgcg        960
tcggaggtca ccatcaaaaa ggctatcaac cggttcctgc cgaggttcaa tgacaaggaa       1020
ctgtttaaca gggccatgtg ctggtgcacc gataccgcgg atagcaatct gcttgtttgt       1080
gagcatccac gctggaaggg gttttatctt gcaacagggg acagcgggca ttcgttcaag       1140
ttgctgccga atattggaaa gcacgttgtc gagttattgg aggggaggct ggaaagtgtg       1200
tttaaggatg cttggaggtg gaggcctggc agtggggatg cattaaagag tagacgggct       1260
gcgcctgcga aggacctggc ggatatgccg gggtggagga tgaggcaaa gatgtag           1317
```

<210> SEQ ID NO 69
<211> LENGTH: 1317
<212> TYPE: DNA
<213> ORGANISM: Artificial
<220> FEATURE:
<223> OTHER INFORMATION: FPOX-40

<400> SEQUENCE: 69

```
atggcgcccc gagccaacac caaaatcatc gtcgtcggcg gcggcggcac aatgggctcg         60
tcgacagccc tacacctcct gcgcgccggc tacacgccgt ccaacatcac agtgctcgac        120
acgtacccta tcccttccgc acagtctgca ggctacgacc tgaacaagat cttcggcatc        180
tcaggcgcga acaagcatga cttacaactc tcgcttgagg cgttcgacat gtggaaaaat        240
gatcctctat tcaagccgtt tttccacaat gttggacaga tggacgtctc ttcaacagaa        300
gaaggcatca aacgccttcg caaaagatac cagtctcttc tccgcgcagg cattgggctc        360
gagaagacga atttcctgct ggaaagtgaa gacgagatcc tggctaaagc gccgcatttc        420
acgcgggagc agattaaagg ctggaaaggg ctgttctgtg gcgacggcgg ttggctcgct        480
gcagccaaag ccatcaatgc catcgggcag ttcctcaagg aacagggcgt caagtttgga        540
tttggcgagg ccggcacgtt caaaaagcca ctcttcgccg atgccgacga aagacgtgc         600 atcggcgtcg aaactgtaga cggcacaaaa tactacgccg acaaggtcgt tctagcagct        660
ggtgcctgga gttcgacgtt ggtcgatctg gaggagcagt gcgtttcaaa ggcctgggtc        720
tttgcccaca tccaactgac gcccgctgaa gcagccgcgt acaagaacac tcctgttata        780
tacgacggtg actatgggtt tttcattgag ccggacgaga acggcatcat aaaagtctgc        840
gacgaattcc ctggcttcac gcacttcaag atgcaccagc cgtacggctc accggtgccc        900
aaattgatct ctgtgcctcg ctcccatgcg aagcacccca cagatacata cccgcacgcg        960
```

```
tcggaggtca ccatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatg cattaaagag tagacgggct    1260
gcgcctgcga aggacctggc ggatatgccg gggtggagga tgaggcaaa gatgtag      1317
```

<210> SEQ ID NO 70
<211> LENGTH: 1317
<212> TYPE: DNA
<213> ORGANISM: Artificial
<220> FEATURE:
<223> OTHER INFORMATION: FPOX-41

<400> SEQUENCE: 70

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac    120
acgtacccta tccttccgc acagtctgca ggctacgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc    600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatg cattaaagag tagacgggct    1260
gcgcctgcga aggacctggc ggatatgccg gggtggagga tgaggcaaa gatgtag      1317
```

<210> SEQ ID NO 71
<211> LENGTH: 1317
<212> TYPE: DNA
<213> ORGANISM: Artificial
<220> FEATURE:
<223> OTHER INFORMATION: FPOX-42

<400> SEQUENCE: 71

```
atggcgcccc gagccaacac caaaatcatc gtcgtcggcg gcggcggcac aatgggctcg    60
```

```
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggacgtctc ttcaacagaa    300
gaaggcatca aacgccttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atagcaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 72
<211> LENGTH: 1317
<212> TYPE: DNA
<213> ORGANISM: Artificial
<220> FEATURE:
<223> OTHER INFORMATION: FPOX-43

<400> SEQUENCE: 72

```
atggcgcccc gagccaacac caaaatcatc gtcgtcggcg gcggcggcac aatgggctcg     60
tcgacagccc tacacctcct gcgcgccggc tacacgccga ccaacatcac agtgctcgac    120
acgtacccta tcccttccgc acagtctgca ggctacgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggacgtctc ttcaacagaa    300
gaaggcatca aacgccttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
```

```
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atagcaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 73
<211> LENGTH: 1317
<212> TYPE: DNA
<213> ORGANISM: Artificial
<220> FEATURE:
<223> OTHER INFORMATION: FPOX-44

<400> SEQUENCE: 73

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggccatgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggacgtctc ttcaacagaa    300
gaaggcatca aacgccttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga agacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atagcaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 74
<211> LENGTH: 1317
<212> TYPE: DNA
<213> ORGANISM: Artificial
<220> FEATURE:
<223> OTHER INFORMATION: FPOX-45

```
<400> SEQUENCE: 74
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaggt cttcggcatc     180
tcaggcgcga acaagcatga cttacaactc tcgcttgagg cgttcgacat gtggaaaaat     240
gatcctctat tcaagccgtt tttccacaat gttggacaga tggacgtctc ttcaacagaa     300
gaaggcatca aacgccttcg ccgcagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317

<210> SEQ ID NO 75
<211> LENGTH: 1317
<212> TYPE: DNA
<213> ORGANISM: Artificial
<220> FEATURE:
<223> OTHER INFORMATION: FPOX-46

<400> SEQUENCE: 75
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aacgccttcg ccgcagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
```

```
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 76
<211> LENGTH: 1311
<212> TYPE: DNA
<213> ORGANISM: Artificial
<220> FEATURE:
<223> OTHER INFORMATION: AoFPOX

<400> SEQUENCE: 76

```
atgactgtca ccaaatcttc ctcaatcctg atcatcggcg caggcacttg gggcgcttca       60
actgcccttc accttggtcg cagaggatac accaatgtca ccgtcctaga cccttacaca      120
gtgccctcag caatttcagc tggaaatgac gtgaacaaga tcatctcctc ggggcaatac      180
agcaacaaaa aggatgagat tgaagttaac gaaattctcg ccgaggaggc attcaaaggc      240
tggacaaccg acccttttgtt caagccatac taccacgaca ctggcgttgt aatgtctgct      300
tgcagcagcg ccggtctgga tcgcctcgga atccgagtaa ggccggaaga ggaacctgat      360
gtttccgaag tcacgaagcc ggagcacttc cgccaactgg cccccgctgt gctgaaagga      420
aacttcccgg ggtggagagg ctaccacatt cgttcgaacg ctggctgggc gcacgcccga      480
aatgccctcg tggccgctat acgcgaagca gagaaacttg tgttaaaatt cgtaacaggc      540
acccaaggaa gagtcatcac ccttatcttc gagaacaacg acgtcaaggg cgcagtcacc      600
gccgacggaa agatctggcg cgcggagcaa acagttctct gcgctggcgc aaatgctgcg      660
cagttcttgg attttaagga ccagctccgc ccaacggcat ggacactcgc ccatatccgg      720
ctcaaacctg aggaacgcgc gctctacaaa aacttgccgg tgattttcaa cattgagaaa      780 ggattttttct tcgagcctga tgaggagcgc ggggagatca agatctgcga cgaacatccg      840
ggatacacta acatggttaa atctgcggat ggccacttga cgagtttgcc ctttgagaag      900
acccagatcc ccaaggagtc tgaagctaga gtcagagctt tactatcgga gaccatgcct      960
caattagccg atcgcccatt tagcttcgcc cgcgtttgct ggtgtgcgga caccgcaaac     1020
cgtgaattca tcattgaccg ccaccctgaa caccgtctc ttgttttggg atgcggtgct     1080
tccggaaggg gtttcaaata tctccctca atcggcaacc tcattgttga cgccattgaa     1140
gacaaagtcc cagagaaagt tcacaagctt acgaggtgga gtccagacat tgctgttgac     1200
agaaagtgga gggacactct ggggcgcttt ggagggccta accgtgtcat ggacttccat     1260
gatgtcaagg aatggactaa cgtgcagaac aaggatactg cgaagctgta g              1311
```

<210> SEQ ID NO 77
<211> LENGTH: 30
<212> TYPE: DNA

```
<213> ORGANISM: Artificial
<220> FEATURE:
<223> OTHER INFORMATION: An artificially synthesized primer sequence

<400> SEQUENCE: 77
ggctacgacc tgaacaaaat cttcggcatc                                       30

<210> SEQ ID NO 78
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 78
cttgttgcgc agcctgatgc cgaagatttt                                       30

<210> SEQ ID NO 79
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 79
tcaacagaag aaggcatcaa aaagcttcgc                                       30

<210> SEQ ID NO 80
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 80
agactggtat ctcatgcgaa gcttttttgat                                      30

<210> SEQ ID NO 81
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 81
ggcgtcaagt ttggatttgg cgaggccggc                                       30

<210> SEQ ID NO 82
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 82 tggcttttg aacgtgccgg cctcgccaaa                                        30

<210> SEQ ID NO 83
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 83
tatgggtttt tcattgagcc ggacgagaac                                       30
```

```
<210> SEQ ID NO 84
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 84 gactttatg atgccgttct cgtccggctc                                   30

<210> SEQ ID NO 85
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 85
tacggctcac cggtgcccaa attgatctct                                  30

<210> SEQ ID NO 86
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 86
atgggagcga ggcacagaga tcaatttggg                                  30

<210> SEQ ID NO 87
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 87
caattaatca tccggctcgt a                                           21

<210> SEQ ID NO 88
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 88
cttctgagtt cggcatgggg                                             20

<210> SEQ ID NO 89
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 89
tcaagtttgg atttggcga                                              19

<210> SEQ ID NO 90
<211> LENGTH: 31
<212> TYPE: DNA
<213> ORGANISM: Artificial
<220> FEATURE:
```

```
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 90
cctgaacaaa atcttcggca tcnnsctgcg c                              31

<210> SEQ ID NO 91
<211> LENGTH: 31
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (24)..(25)
<223> OTHER INFORMATION: n is a, c, g, or t

<400> SEQUENCE: 91
gtaagtcagg cttgttgcgc agsnngatgc c                              31

<210> SEQ ID NO 92
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (22)..(23)
<223> OTHER INFORMATION: n is a, c, g, or t

<400> SEQUENCE: 92
aaaatcttcg gcatcggcct gnnsaacaag                                30

<210> SEQ ID NO 93
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 93
gagttgtaag tcaggcttgt tsnncaggcc                                30

<210> SEQ ID NO 94
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 94
aaaatcttcg gcatctcact ggcgaacaag                                30

<210> SEQ ID NO 95
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 95
```
gagttgtaag tcaggcttgt tcgccagtga 30

<210> SEQ ID NO 96
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (22)..(23)
<223> OTHER INFORMATION: n is a, c, g, or t

<400> SEQUENCE: 96
aacaaaatct tcggcatctc annsgcgaac 30

<210> SEQ ID NO 97
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 97
ttgtaagtca ggcttgttcg csnntgagat 30

<210> SEQ ID NO 98
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 98
cacaatgttg gagaaatgga cgtctcttca ac 32

<210> SEQ ID NO 99
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 99
gttgaagaga cgtccatttc tccaacattg tg 32

<210> SEQ ID NO 100
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 100
cggtgactat gggtatttca ttgagccgga c 31

<210> SEQ ID NO 101
<211> LENGTH: 31
<212> TYPE: DNA
<213> ORGANISM: Artificial
<220> FEATURE:
<223> OTHER INFORMATION: An artificially synthesized primer sequence

```
<400> SEQUENCE: 101
gtccggctca atgaaatacc catagtcacc g                              31

<210> SEQ ID NO 102
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 102
cagtctgcag gctacgacct gaacaagatc                                30

<210> SEQ ID NO 103
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 103
gatcttgttc aggtcgtagc ctgcagactg                                30

<210> SEQ ID NO 104
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 104
ccagcaggaa attcgtcttc tcgag                                     25

<210> SEQ ID NO 105
<211> LENGTH: 31
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 105
gaacaagcct gacttacaac tcnnscttga g                              31

<210> SEQ ID NO 106
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 106
ccacatgtcc agcgcctcaa gsnngagttg                                30

<210> SEQ ID NO 107
<211> LENGTH: 31
<212> TYPE: DNA
<213> ORGANISM: Artificial
<220> FEATURE:
<223> OTHER INFORMATION: An artificially synthesized primer sequence
```

```
<220> FEATURE:
<221> NAME/KEY: misc_feature
<222> LOCATION: (23)..(24)
<223> OTHER INFORMATION: n is a, c, g, or t

<400> SEQUENCE: 107
catgagatac cagtctcttc tcnnsgcagg c                                      31

<210> SEQ ID NO 108
<211> LENGTH: 32
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (25)..(26)
<223> OTHER INFORMATION: n is a, c, g, or t

<400> SEQUENCE: 108
gtcttctcga gcccaatgcc tgcsnngaga ag                                     32

<210> SEQ ID NO 109
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (22)..(23)
<223> OTHER INFORMATION: n is a, c, g, or t

<400> SEQUENCE: 109
gaaggcatca aaaagcttcg cnnsagatac                                        30

<210> SEQ ID NO 110
<211> LENGTH: 30
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (23)..(24)
<223> OTHER INFORMATION: n is a, c, g, or t

<400> SEQUENCE: 110
gcggagaaga gactggtatc tsnngcgaag                                        30

<210> SEQ ID NO 111
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 111
gaggcggccg acatgtggaa aaatgatcct cta                                    33

<210> SEQ ID NO 112
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 112
```
catgtcggcc gcctcaaggc tgagttgtaa g         31

<210> SEQ ID NO 113
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 113
cttacaactc tcgcttgagg cgttcgacat g         31

<210> SEQ ID NO 114
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 114
gaggatcatt tttccacatg tcgaacgcct c         31

<210> SEQ ID NO 115
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 115
ctgcgcgccg gctacacgcc gaccaacatc         30

<210> SEQ ID NO 116
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 116
cgtgtcgagc actgtgatgt tggtcggcgt         30

<210> SEQ ID NO 117
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 117
ccttccgcac agtctgcagg ccatgacctg         30

<210> SEQ ID NO 118
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 118
gccgaagatc ttgttcaggt catggcctgc         30

<210> SEQ ID NO 119
<211> LENGTH: 30
<212> TYPE: DNA
<213> ORGANISM: Artificial

```
<220> FEATURE:
<223> OTHER INFORMATION: An artificially synthesized primer sequence

<400> SEQUENCE: 119
gcaggctacg acctgaacaa ggtcttcggc                                30

<210> SEQ ID NO 120
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 120
gttcgcgcct gagatgccga agaccttgtt                                30

<210> SEQ ID NO 121
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 121
ggcatctcag gcgcgaacaa gcatgactta                                30

<210> SEQ ID NO 122
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 122
ctcaaggctg agttgtaagt catgcttgtt                                30

<210> SEQ ID NO 123
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 123
ttccacaatg ttggacagat ggaagtctct                                30

<210> SEQ ID NO 124
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 124
gccttcttct gttgaagaga cttccatctg                                30

<210> SEQ ID NO 125
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 125
tcaacagaag aaggcatcaa acgccttcgc                                30
```

```
<210> SEQ ID NO 126
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 126
gagactggta tcttttgcga aggcgtttga t                              31

<210> SEQ ID NO 127
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 127
gagactggta tctgcggcga aggcgtttga t                              31

<210> SEQ ID NO 128
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 128
gaaggcatca aaaagcttcg ccgcagatac                                30

<210> SEQ ID NO 129
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 129
gcggagaaga gactggtatc tgcggcgaag                                30

<210> SEQ ID NO 130
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 130
tggtgcaccg ataccgcgga tagcaatctg                                30

<210> SEQ ID NO 131
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 131
gatgctcaca aacaagcaga ttgctatccg c                              31

<210> SEQ ID NO 132
<211> LENGTH: 43
<212> TYPE: DNA
<213> ORGANISM: Artificial
<220> FEATURE:
<223> OTHER INFORMATION: An artificially synthesized primer sequence
```

```
<400> SEQUENCE: 132
atgccatggg ccaccaccac cacatgactg tcaccaaatc ttc                              43

<210> SEQ ID NO 133
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 133
atgggatccc tacagcttcg cagtatcctt                                             30

<210> SEQ ID NO 134
<211> LENGTH: 6
<212> TYPE: PRT
<213> ORGANISM: Artificial Sequence
<220> FEATURE:
<223> OTHER INFORMATION: Synthetic Construct

<400> SEQUENCE: 134

Val His Leu Thr Pro Glu
1               5

<210> SEQ ID NO 135
<211> LENGTH: 6
<212> TYPE: PRT
<213> ORGANISM: Artificial Sequence
<220> FEATURE:
<223> OTHER INFORMATION: Synthetic Construct

<400> SEQUENCE: 135

Val Leu Ser Pro Ala Asp
1               5
```